US012364771B2

(12) United States Patent
Ashley et al.

(10) Patent No.: US 12,364,771 B2
(45) Date of Patent: Jul. 22, 2025

(54) CONJUGATION LINKERS

(71) Applicant: ProLynx LLC, San Francisco, CA (US)

(72) Inventors: Gary W. Ashley, Alameda, CA (US); Brian Hearn, Moraga, CA (US); Shaun Fontaine, Concord, CA (US); Eric L. Schneider, Oakland, CA (US)

(73) Assignee: PROLYNX LLC, San Francisco, CA (US)

( * ) Notice: Subject to any disclaimer, the term of this patent is extended or adjusted under 35 U.S.C. 154(b) by 260 days.

(21) Appl. No.: 17/601,575

(22) PCT Filed: Apr. 3, 2020

(86) PCT No.: PCT/US2020/026726
§ 371 (c)(1),
(2) Date: Oct. 5, 2021

(87) PCT Pub. No.: WO2020/206358
PCT Pub. Date: Oct. 8, 2020

(65) Prior Publication Data
US 2022/0280654 A1 Sep. 8, 2022

Related U.S. Application Data

(60) Provisional application No. 62/830,280, filed on Apr. 5, 2019.

(51) Int. Cl.
*A61K 38/12* (2006.01)
*A61K 38/26* (2006.01)
*A61K 38/28* (2006.01)
*A61K 47/54* (2017.01)
*A61K 47/60* (2017.01)
*A61K 47/69* (2017.01)

(52) U.S. Cl.
CPC .......... *A61K 47/6903* (2017.08); *A61K 38/12* (2013.01); *A61K 38/26* (2013.01); *A61K 38/28* (2013.01); *A61K 47/542* (2017.08); *A61K 47/60* (2017.08)

(58) Field of Classification Search
None
See application file for complete search history.

(56) References Cited

U.S. PATENT DOCUMENTS

| 6,258,898 B1 | 7/2001 | Rehfuss et al. |
| 8,097,586 B2 | 1/2012 | Lv et al. |
| 8,680,315 B2 | 3/2014 | Santi et al. |
| 8,754,190 B2 | 6/2014 | Ashley et al. |
| 8,946,405 B2 | 2/2015 | Ashley et al. |
| 9,649,385 B2 | 5/2017 | Ashley et al. |
| 9,707,176 B2 | 7/2017 | Brunner-Schwarz et al. |
| 10,398,779 B2 | 9/2019 | Ashley et al. |
| 11,179,470 B2 | 11/2021 | Ashley et al. |
| 11,181,803 B2 | 11/2021 | Ashley et al. |
| 11,454,861 B2 | 9/2022 | Ashley et al. |
| 2004/0013637 A1 | 1/2004 | Bentley et al. |
| 2005/0143484 A1 | 6/2005 | Fang et al. |
| 2005/0171014 A1 | 8/2005 | Tarasova et al. |
| 2006/0194719 A1 | 8/2006 | Ebbehoj et al. |
| 2007/0037750 A1 | 2/2007 | Young et al. |
| 2009/0269406 A1 | 10/2009 | Panitch et al. |
| 2010/0009904 A1 | 1/2010 | Lv et al. |
| 2010/0029554 A1 | 2/2010 | Ghosh et al. |
| 2010/0240586 A1 | 9/2010 | Bao et al. |
| 2010/0267895 A1 | 10/2010 | Harris et al. |
| 2011/0263502 A1 | 10/2011 | Santi et al. |
| 2011/0268807 A1 | 11/2011 | Su et al. |
| 2011/0306549 A1 | 12/2011 | Tatarkiewicz et al. |
| 2013/0116407 A1 | 5/2013 | Ashley et al. |
| 2013/0123487 A1 | 5/2013 | Ashley et al. |
| 2014/0256626 A1 | 9/2014 | Santi et al. |
| 2014/0288190 A1 | 9/2014 | Ashley et al. |
| 2018/0289695 A1 | 10/2018 | Ashley et al. |
| 2020/0164083 A1 | 5/2020 | Schneider et al. |
| 2023/0135347 A1 | 5/2023 | Ashley et al. |

FOREIGN PATENT DOCUMENTS

| JP | S62281867 | 12/1987 |
| WO | WO 1999/043656 | 9/1999 |
| WO | WO 2001/064650 | 9/2001 |
| WO | WO 2004/022004 | 3/2004 |
| WO | WO 2004/052349 | 6/2004 |
| WO | WO 2006/003014 | 1/2006 |
| WO | WO 2008/116294 | 10/2008 |
| WO | WO 2009/158668 | 12/2009 |
| WO | WO 2010/059883 | 5/2010 |
| WO | WO 2011/140376 | 11/2011 |
| WO | WO 2011/140393 | 11/2011 |
| WO | WO 2013/036847 | 3/2013 |
| WO | WO 2013/059323 | 4/2013 |
| WO | WO-2015/187540 | 12/2015 |

(Continued)

OTHER PUBLICATIONS

Ashley et al., "Hydrogel drug delivery system with predictable and tunable drug release and degradation rates," Proc Natl Acad Sci USA (2013) 110(6):2318-2323.
Doxorubicin, The Myeloma Beacon, Published Oct. 15, 2008, Retrieved from the Internet <URL: https://myelomabeacon.org/resources/2008/10/15/doxorubicin/>, 5 pages.
Eng et al., "Isolation and Characterization of Exendin-4, an Exendin-3 Analogue, from Heloderma suspectum Venom," The Journal of Biological Chemistry (1992) 267(11):7402-7405.
Geiger et al., "Deamidation, isomerization, and racemization at asparaginyl and aspartyl residues in peptides. Succinimide-linked reactions that contribute to protein degradation," Biol Chem (1987) 262(2):785-794.

(Continued)

*Primary Examiner* — Thomas S Heard
(74) *Attorney, Agent, or Firm* — MORRISON & FOERSTER LLP

(57) ABSTRACT

Provided are β-eliminative linkers suitable for the conjugation of small molecule, peptide, and protein and compounds comprising the linkers.

11 Claims, 10 Drawing Sheets
Specification includes a Sequence Listing.

(56) References Cited

FOREIGN PATENT DOCUMENTS

| WO | WO 2017/161174 | 9/2017 |
|----|----------------|--------|
| WO | WO 2019/152672 | 8/2019 |
| WO | WO-2021/041964 | 3/2021 |

OTHER PUBLICATIONS

Kim et al., "Peptide Amidation: Production of Peptides Hormones in vivo and in vitro," Biotechnol. Bioprocess Eng. (2001) 6:244-251.

Lyu et al., "Degradability of polymers for implantable biomedical devices," Int J Mol Sci (2009) 10(9):4033-4065.

Manandhar et al., "Glucagon-like peptide-1 (GLP-1) analogs: recent advances, new possibilities, and therapeutic implications," J Med Chem (2015) 58(3):1020-1037.

Rayner et al., "Preparation and reactions of enantiomerically pure α-functionalized Grignard reagents," J Am Chem Soc (2013) 135(21):8071-8077.

Reid et al., "Analytical and Simulation-Based Models for Drug Release and Gel-Degradation in a Tetra-PEG Hydrogel Drug Delivery System," Macromolecules (2015) 48:7359-7369.

Schneider et al., "Hydrogel Drug Delivery System Using Self-Cleaving Covalent Linkers for Once-a-Week Administration of Exenatide," Bioconjug Chem (2016) 27(5):1210-1215.

Schneider et al., "Hydrogel Drug Delivery System Using Self-Cleaving Covalent Linkers for Once-a-Week Administration of Exenatide," Bioconjug Chem (2016) 27(5):1210-1215. Supplementary information, 6 pages.

Kocienski et al., "Synthetic approaches to pederin. A synthesis of (Y)-benzoylpedamide," Journal of the Chemical Society. Chemical Communications (1984) (15):1011-1012.

| pH | Linker | [Gly] (M) | $k_f$ (M$^{-1}$h$^{-1}$) | $k_r$ (h$^{-1}$) | $K_{eq}$ (M$^{-1}$) | $K_{eq\text{-}Std}/K_{eq}$ |
|---|---|---|---|---|---|---|
| 7.4 | Std | 1.0 | 0.0263 | 0.0027 | 9.64 | 1 |
| | β-Me | 1.0 | 0.00113 | 0.0046 | 0.243 | 40 |
| | gem diMe | 1.0 | 0.00015 | 0.0044 | 0.0348 | 277 |
| 8.4 | Std | 1.0 | 0.216 | 0.0053 | 40.7 | 1 |
| | β-Me | 1.0 | 0.0094 | 0.0090 | 1.05 | 39 |
| | gem diMe | 1.0 | 0.00143 | 0.0068 | 0.209 | 195 |
| 9.5 | Std | 0.1 | 1.45 | 0.0051 | 284 | 1 |
| | β-Me | 0.1 | 0.0602 | 0.0078 | 7.73 | 37 |
| | gem diMe | 0.1 | 0.00833 | 0.0057 | 1.45 | 196 |

SEQUENCE LISTING

<160> NUMBER OF SEQ ID NOS: 6

<210> SEQ ID NO 1
<211> LENGTH: 39
<212> TYPE: PRT
<213> ORGANISM: Artificial Sequence
<220> FEATURE:
<223> OTHER INFORMATION: [N28Q]exenatide
<220> FEATURE:
<221> NAME/KEY: AMIDATION
<222> LOCATION: 39
<223> OTHER INFORMATION: NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 2
<211> LENGTH: 21
<212> TYPE: PRT
<213> ORGANISM: Artificial Sequence
<220> FEATURE:
<223> OTHER INFORMATION: A chain of insulin lispro

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Artificial Sequence
<220> FEATURE:
<223> OTHER INFORMATION: B chain of insulin lispro

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 33
<212> TYPE: PRT
<213> ORGANISM: Artificial Sequence
<220> FEATURE:
<223> OTHER INFORMATION: Teduglutide ([Gly2]GLP-2)

```
<400> SEQUENCE: 4

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp

<210> SEQ ID NO 5
<211> LENGTH: 8
<212> TYPE: PRT
<213> ORGANISM: Artificial Sequence
<220> FEATURE:
<223> OTHER INFORMATION: octreotide; Cys2-Cys7 cyclic disulfide

<400> SEQUENCE: 5

Phe Cys Phe Trp Lys Thr Cys Thr
1               5

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
tcgaacgttc gaacgttcga acgttcgaat                                    30
```

CONJUGATION LINKERS

CROSS-REFERENCE TO RELATED APPLICATIONS

This application is a national stage application under 35 U.S.C. § 371 of International Application No. PCT/US2020/026726, filed internationally on Apr. 3, 2020, which claims priority to U.S. Provisional Application No. 62/830,280, filed Apr. 5, 2019, the contents of which are incorporated herein by reference in their entirety.

INCORPORATION BY REFERENCE OF SEQUENCE LISTING

The present application is being filed along with a Sequence Listing in electronic format. The content of the following submission on ASCII text file is incorporated herein by reference in its entirety: a computer readable form (CRF) of the Sequence Listing (file name: 670572002100SEQLIST.TXT, date recorded: Sep. 29, 2021, size: 2,210 bytes).

FIELD

This disclosure generally relates to β-eliminative linkers suitable for the conjugation of small molecules, peptides, oligonucleotides, and proteins and compounds comprising the linkers.

BACKGROUND

Drug molecules are covalently bound to macromolecular carriers in order to enhance pharmaceutical properties, such as half-life, stability, solubility, tolerability, and safety. U.S. Pat. Nos. 8,680,315, 8,754,190, and 9,649,385 disclose drug conjugate systems having β-eliminative linkers, which allow drug release through a rate-controlled, beta-elimination mechanism. However, along with released drug or severed crosslink, the β-elimination process generates a linker residue bound to the macromolecular carrier comprising an alkenyl group that may be activated for nucleophilic addition. As shown in FIG. 1, potential nucleophiles for this addition under physiological conditions include thiols and amines, for example, those that are present in significant quantities on proteins or more probably the amines that are released from severing a crosslink in a hydrogel. While amines are expected to be protonated and thus unreactive at physiological pH, it has been unexpectedly found that such aza-Michael addition occurs at least in an in vitro setting. Previously disclosed linkers (i.e., U.S. Pat. Nos. 8,680,315 and 8,754,190) provide a means of relief from this undesired reaction through addition of an alkyl group on the carbon having the leaving oxygen (equivalent to the group $R^5$ in formula (I) of U.S. Pat. No. 8,680,315), as shown in FIG. 2. There is a need for improved linkers which can suppress the undesired aza-Michael addition more effectively.

BRIEF SUMMARY

In one aspect, provided is a linker of formula (I),

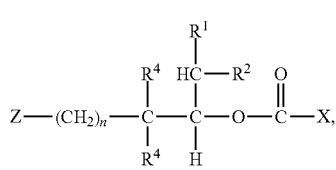

wherein n, $R^1$, $R^2$, $R^4$, X, and Z are as disclosed herein. In some embodiments, the linker is a β-eliminative linker. In some embodiments, the β-eliminative linker is suitable for the conjugation of small molecule, peptide, and protein therapeutics.

In another aspect, provided is a linker-drug of formula (II),

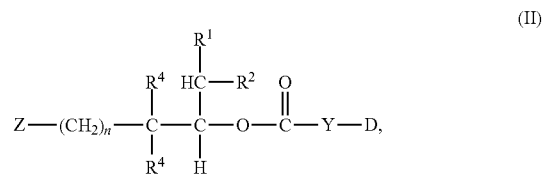

wherein n, $R^1$, $R^2$, $R^4$, Y, Z, and D are as disclosed herein. In some embodiments, the linker-drug of formula (II) is prepared by combining the linker of formula (I) with a drug such as a small molecule, peptide, or protein therapeutic.

In yet another aspect, provided is a conjugate of formula (III),

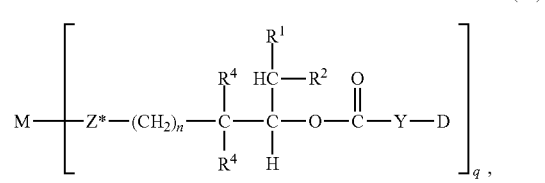

wherein n, q, $R^1$, $R^2$, $R^4$, M, Y, Z*, and D are as disclosed herein. In some embodiments, the conjugate of formula (III) is a conjugate of drug D releasably linked to a macromolecular carrier M through a linker of formula (I).

In yet another aspect, provided is a hydrogel of formula (IV),

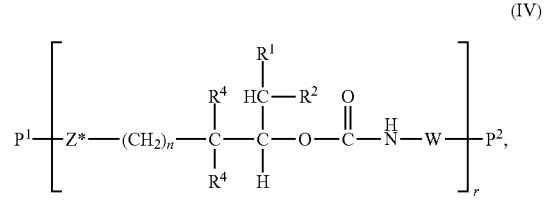

wherein n, r, $R^1$, $R^2$, $R^4$, W, Z*, $P^1$, and $P^2$ are as disclosed herein. In some embodiments, the compound of formula (IV) is a degradable crosslinked hydrogel. In some embodiments, the degradable crosslinked hydrogel comprises the residue of a linker of formula (I).

In yet another aspect, provided are methods for preparing the compounds of formulas (I), (II), (III), and (IV), and methods for their use. In another aspect, provided are pharmaceutical compositions containing a conjugate of formula (III) or a hydrogel of formula (IV).

DETAILED DESCRIPTION

Figure 3:
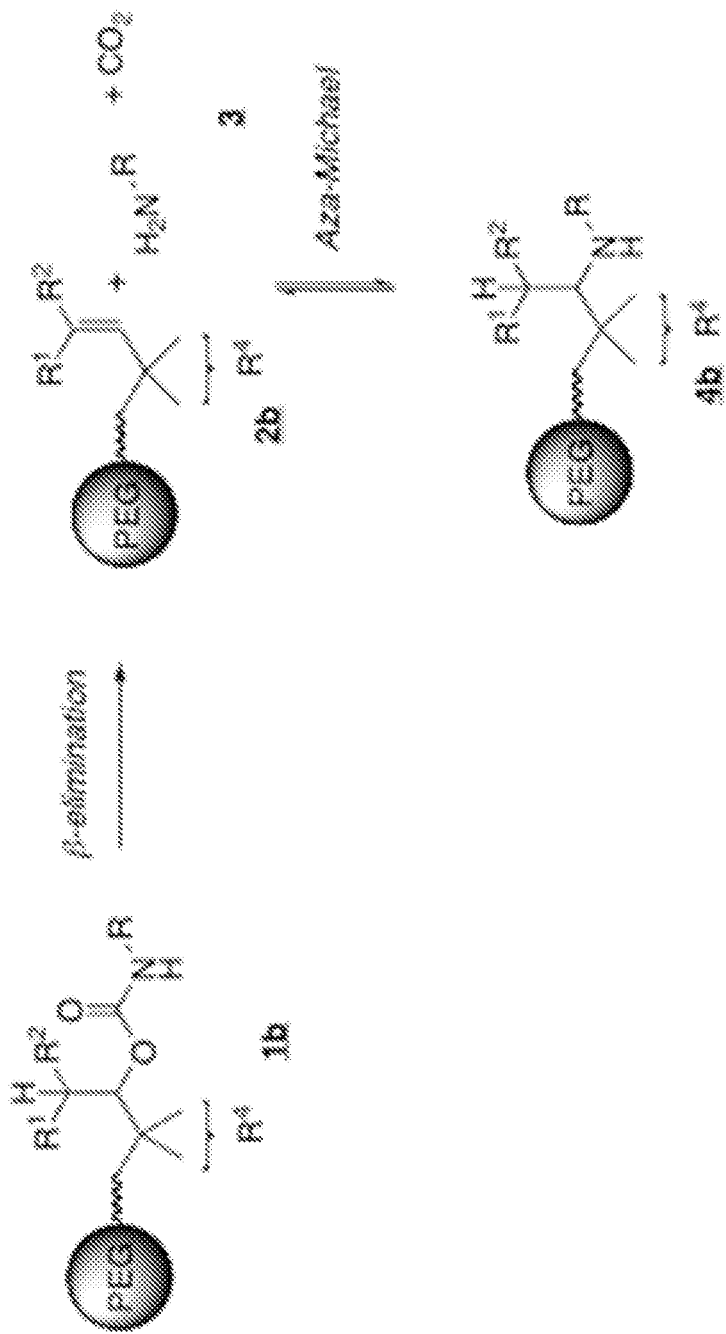
FIG. 3 illustrates the cleavage of a γ-disubstituted carbamate linker disclosed herein in a conjugate.
Figure 4:
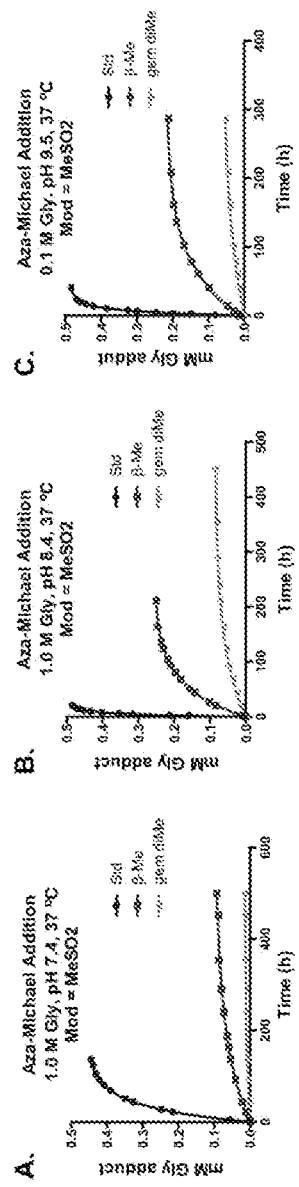
FIG. 4 shows the rate of aza-Michael addition of glycine into linker vinyl sulfones at various pH values. Prism plot of glycine adduct concentration (mM) vs time (h) for the Std, β-Me, and gem diMe linkers: A) pH 7.4, 1.0 M glycine; B) pH 8.4, 1.0 M glycine; C) pH 9.5, 0.1 M glycine. Tabulated data from each experiment including kf, kr, and Keq were calculated as described in the Methods section.
Figure 5:
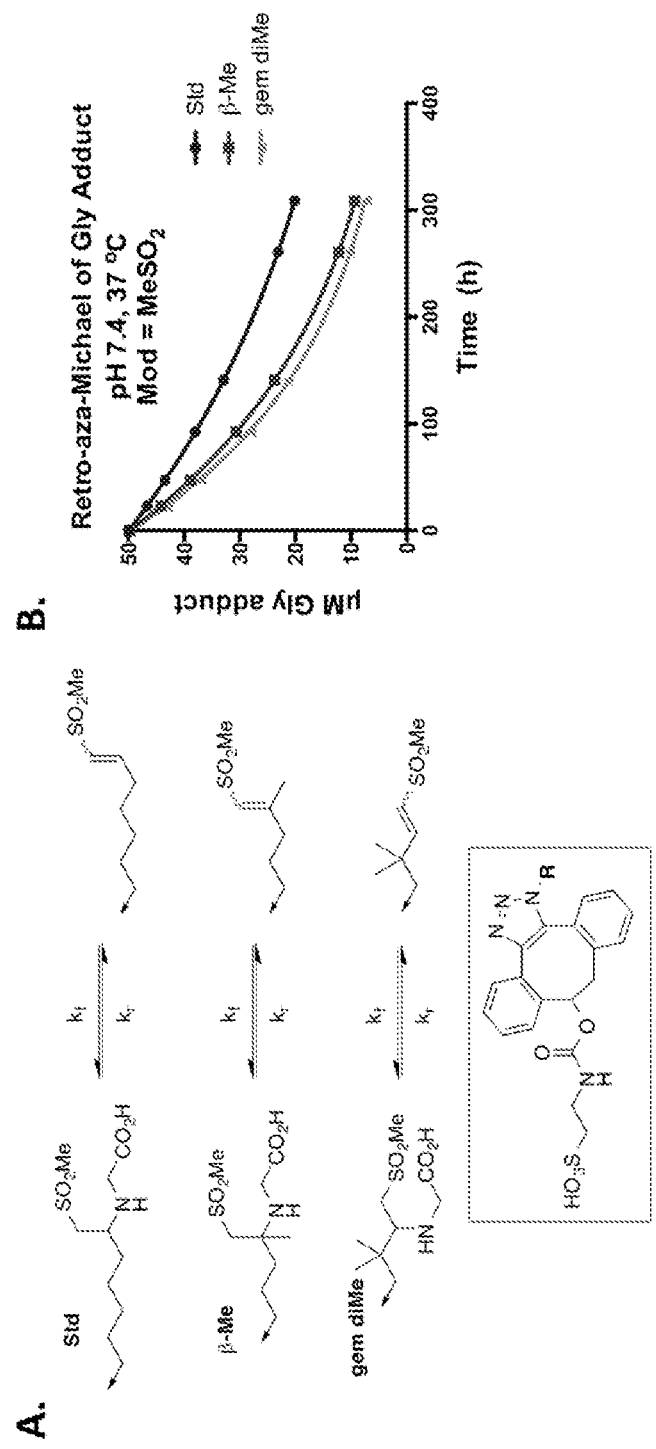
FIG. 5 shows the rate of retro-aza-Michael elimination of glycine from β-N-glycyl methyl sulfones. A) Schematic of the retro-aza-Michael reaction for each linker. B) Prism plot of glycine adduct concentration (μM) vs time (h). Std linker, $k_{obs}$=0.0030 h$^{-1}$; β-Me linker, $k_{obs}$=0.0050 h$^{-1}$; gem diMe linker $k_{obs}$=0.0060 h$^{-1}$. For each linker, the calculated [Gly-adduct]$_{equil}$≤1 μM.

Compared with the previously disclosed β-eliminative linkers, it has been found that the undesired aza-Michael addition can be suppressed far more effectively by the linkers disclosed herein, which incorporate a geminally-substituted carbon adjacent to the carbon having the leaving oxygen, i.e., at the gamma-carbon, as shown in FIG. 3. The resulting linkers of formula (I) disclosed herein provide conjugates wherein the rate of addition of nucleophiles to the linker remnant is greatly suppressed, and the resulting equilibrium constant is correspondingly quite low.

Definitions

For use herein, unless clearly indicated otherwise, use of the terms "a", "an" and the like refers to one or more.

As used herein, and unless otherwise specified, the term "about," when used in connection with a value, contemplates a value within 15%, within 10%, within 5%, within 4%, within 3%, within 2%, within 1%, or within 0.5% of the value.

The term "alkyl" includes linear, branched, or cyclic saturated hydrocarbon groups of 1-20, 1-12, 1-8, 1-6, or 1-4 carbon atoms. In some embodiment, an alkyl is linear or branched. Examples of linear or branched alkyl groups include, without limitation, methyl, ethyl, n-propyl, isopropyl, n-butyl, t-butyl, isobutyl, sec-butyl, n-pentyl, n-hexyl, n-heptyl, n-octyl, n-nonyl, n-decyl, and the like. In some embodiments, an alkyl is cyclic. Examples of cyclic alkyl groups include, without limitation, cyclopropyl, cyclobutyl, cyclopentyl, cyclopentadienyl, cyclohexyl, and the like.

The term "alkoxy" includes alkyl groups bonded to oxygen, including methoxy, ethoxy, isopropoxy, cyclopropoxy, cyclobutoxy, and the like.

The term "alkenyl" includes non-aromatic unsaturated hydrocarbons with carbon-carbon double bonds and 2-20, 2-12, 2-8, 2-6, or 2-4 carbon atoms.

The term "alkynyl" includes non-aromatic unsaturated hydrocarbons with carbon-carbon triple bonds and 2-20, 2-12, 2-8, 2-6, or 2-4 carbon atoms.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and the like.

In some instances, alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" or "halo" includes bromo, fluoro, chloro and iodo.

The term "heterocyclic ring" or "heterocyclyl" refers to a 3-15 membered aromatic or non-aromatic ring comprising at least one N, O, or S atom. Examples include, without limitation, piperidinyl, piperazinyl, tetrahydropyranyl, pyrrolidine, and tetrahydrofuranyl, as well as the exemplary groups provided for the term "heteroaryl" above. In some embodiments, a heterocyclic ring or heterocyclyl is non-aromatic. In some embodiments, a heterocyclic ring or heterocyclyl is aromatic.

The term "macromolecule" refers to a molecule or residue of a molecule having a molecular weight between 5,000 and 1,000,000 Daltons, preferably between 10,000 and 500,000 Daltons, and more preferably between 10,000 and 250,000

Daltons. Examples of macromolecules include, without limitation, proteins including antibodies, antibody fragments, and enzymes; polypeptides including poly(amino acid)s such as poly(lysine) and poly(valine) and mixed-sequence polypeptides; synthetic polymers including poly (ethylene glycol) (PEG), poly(ethylene oxide) (PEO), poly (ethylene imine) (PEI), and co-polymers thereof; and polysaccharides such as dextrans. In some embodiments, the macromolecules comprise at least one functional group suitable for conjugation, either natively or after chemical transformation, such as an amine, carboxylic acid, alcohol, thiol, alkyne, azide, or maleimide group as described above. In certain embodiments of the invention, the macromolecule is a polyethylene glycol. The polyethylene glycol may be linear or branched, with one end terminated with a functional group suitable for conjugation and the other end or ends terminated by a capping group (for example, methyl), or may comprise multiple arms each arm terminating in a functional group suitable for conjugation. In preferred embodiments of the invention, the polyethylene glycol is a linear, branched, or multiple-arm polymer having an average molecular weight between 20,000 and 200,000 Daltons, preferably between 20,000 and 100,000 Daltons, and most preferably approximately 40,000 Daltons. Examples of such polyethylene glycols are known in the art and are commercially available, for example from NOF Corporation (Tokyo, Japan).

The terms "protein" and "peptide" are used interchangeably regardless of chain length, and these terms further include pseudopeptides which comprise linkages other than amide linkages, such as $CH_2NH_2$ linkages as well as peptidomimetics.

The terms "nucleic acid" and "oligonucleotide" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins as well as pseudopeptide bonds and bases not found in nature in the case of nucleic acids as well as backbone variants such as peptide nucleic acids.

The term "small molecule" in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

"Optionally substituted" unless otherwise specified means that a group may be unsubstituted or substituted by one or more (e.g., 1, 2, 3, 4 or 5) of the substituents which may be same or different. Examples of substituents include, without limitation, alkyl, alkenyl, alkynyl, halogen, —CN, —OR$^{aa}$, —SR$^{aa}$, —NR$^{aa}$R$^{bb}$, —NO$_2$, —C=NH(OR$^{aa}$), —C(O)R$^{aa}$, —OC(O)R$^{aa}$, —C(O)OR$^{aa}$, —C(O)NR$^{aa}$R$^{bb}$, —OC(O)NR$^{aa}$R$^{bb}$, —NR$^{aa}$C(O)R$^{bb}$, —NR$^{aa}$C(O)OR$^{bb}$, —S(O)R$^{aa}$, —S(O)$_2$R$^{aa}$, —NR$^{aa}$S(O)R$^{bb}$, —C(O)NR$^{aa}$S(O)R$^{bb}$, —NR$^{aa}$S(O)$_2$R$^{bb}$, —C(O)NR$^{aa}$S(O)$_2$R$^{bb}$, —S(O)NR$^{aa}$R$^{bb}$, —S(O)$_2$NR$^{aa}$R$^{bb}$, —P(O)(OR$^{aa}$) (OR$^{bb}$), heterocyclyl, heteroaryl, or aryl, wherein the alkyl, alkenyl, alkynyl, cycloalkyl, heterocyclyl, heteroaryl, and aryl are each independently optionally substituted by R$^{cc}$, wherein R$^{aa}$ and R$^{bb}$ are each independently H, alkyl, alkenyl, alkynyl, heterocyclyl, heteroaryl, or aryl, or R$^{aa}$ and R$^{bb}$ are taken together with the nitrogen atom to which they attach to form a heterocyclyl, which is optionally substituted by alkyl, alkenyl, alkynyl, halogen, hydroxyl, alkoxy, or —CN, and wherein:

each R$^{cc}$ is independently alkyl, alkenyl, alkynyl, halogen, heterocyclyl, heteroaryl, aryl, —CN, or —NO$_2$.

While typically, the active form of the drug is directly released from the conjugates of the invention, in some cases, it is possible to release the active drug in the form of a prodrug thereof.

Linker

In one aspect, provided herein is a linker of formula (I),

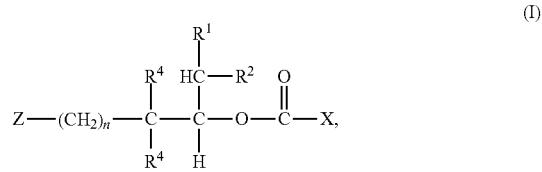

wherein:

n is an integer from 0 to 6;

R$^1$ and R$^2$ are independently an electron-withdrawing group, alkyl, or H, and wherein at least one of R$^1$ and R$^2$ is an electron-withdrawing group;

each R$^4$ is independently C$_1$-C$_3$ alkyl or the two R$^4$ are taken together with the carbon atom to which they attach to form a 3-6 member ring;

X is a leaving group; and

Z is a functional group for connecting the linker to a macromolecular carrier.

In some embodiments of a linker of formula (I), n=1-6, R$^1$ and R$^2$ are independently electron-withdrawing groups, alkyl, or H, and wherein at least one of R$^1$ and R$^2$ is an electron-withdrawing group; each R$^4$ is independently C$_1$-C$_3$ alkyl or taken together may form a 3-6 member ring; X is halogen, active ester such as N-succinimidyloxy, nitrophenoxy, or pentahalophenoxy, or imidazolyl, triazolyl, tetrazolyl, or N(R$^6$)CH$_2$Cl wherein R$^6$ is optionally substituted C$_1$-C$_6$ alkyl, optionally substituted aryl, or optionally substituted heteroaryl; and Z is a functional group for connecting the linker to a macromolecular carrier.

In some embodiments, the electron-withdrawing group of R$^1$ and R$^2$ is

—CN;

—NO$_2$;

optionally substituted aryl;

optionally substituted heteroaryl;

optionally substituted alkenyl;

optionally substituted alkynyl;

—COR$^3$, —SOR$^3$, or —SO$_2$R$^3$, wherein R$^3$ is H, optionally substituted alkyl, optionally substituted aryl, optionally substituted arylalkyl, optionally substituted heteroaryl, optionally substituted heteroarylalkyl, —OR$^8$ or —NR$^8_2$, wherein each R$^8$ is independently H or optionally substituted alkyl, or both R$^8$ groups are taken together with the nitrogen to which they are attached to form a heterocyclic ring; or SR$^9$, wherein R$^9$ is optionally substituted alkyl, optionally substituted aryl, optionally substituted arylalkyl, optionally substituted heteroaryl, or optionally substituted heteroarylalkyl.

In some embodiments, the electron-withdrawing group of R$^1$ and R$^2$ is —CN. In some embodiments, the electron-withdrawing group of $R^1$ and $R^2$ is —$NO_2$. In some embodiments, the electron-withdrawing group of $R^1$ and $R^2$ is optionally substituted aryl containing 6-10 carbons. For instance, in some embodiments, the electron-withdrawing group of $R^1$ and $R^2$ is optionally substituted phenyl, naphthyl, or anthracenyl. In some embodiments, the electron-withdrawing group of $R^1$ and $R^2$ is optionally substituted heteroaryl comprising 3-7 carbons and containing at least one N, O, or S atom. For instance, in some embodiments, the electron-withdrawing group of $R^1$ and $R^2$ is optionally substituted pyrrolyl, pyridyl, pyrimidinyl, imidazolyl, oxazolyl, isoxazolyl, thiazolyl, isothiazolyl, quinolyl, indolyl, or indenyl. In some embodiments, the electron-withdrawing group of $R^1$ and $R^2$ is optionally substituted alkenyl containing 2-20 carbon atoms. In some embodiments, the electron-withdrawing group of $R^1$ and $R^2$ is optionally substituted alkynyl containing 2-20 carbon atoms. In some embodiments, the electron-withdrawing group of $R^1$ and $R^2$ is —$COR^3$, —$SOR^3$, or —$SO_2R^3$, wherein $R^3$ is H, optionally substituted alkyl containing 1-20 carbon atoms, optionally substituted aryl, optionally substituted arylalkyl, optionally substituted heteroaryl, optionally substituted heteroarylalkyl, —$OR^8$ or —$NR^8{}_2$, wherein each $R^8$ is independently H or optionally substituted alkyl containing 1-20 carbon atoms, or both $R^8$ groups are taken together with the nitrogen to which they are attached to form a heterocyclic ring. In some embodiments, the electron-withdrawing group of $R^1$ and $R^2$ is —$SR^9$, wherein $R^9$ is optionally substituted alkyl containing 1-20 carbon atoms, optionally substituted aryl, optionally substituted arylalkyl, optionally substituted heteroaryl, or optionally substituted heteroarylalkyl.

In some embodiments of a linker of formula (I), at least one of $R^1$ and $R^2$ is —CN, —$SOR^3$ or —$SO_2R^3$. In some embodiments, at least one of $R^1$ and $R^2$ is —CN or —$SO_2R^3$. In some embodiments, at least one of $R^1$ and $R^2$ is —CN or —$SO_2R^3$, wherein $R^3$ is optionally substituted alkyl, optionally substituted aryl, or —$NR^8{}_2$. In some embodiments, at least one of $R^1$ and $R^2$ is —CN, —$SO_2N(CH_3)_2$, —$SO_2CH_3$, —$SO_2Ph$, —$SO_2PhCl$, —$SO_2N(CH_2CH_2)_2O$, —$SO_2CH(CH_3)_2$, —$SO_2N(CH_3)(CH_2CH_3)$, or —$SO_2N(CH_2CH_2OCH_3)_2$.

In some embodiments of a linker of formula (I), each $R^4$ is independently $C_1$-$C_3$ alkyl. In some embodiments, both $R^4$ are methyl.

In some embodiments of a linker of formula (I), n is an integer from 1 to 6. In some embodiments, n is an integer from 1 to 3. In some embodiments, n is an integer from 0 to 3. In some embodiments, n is 1. In some embodiments, n is 2. In some embodiments, n is 3.

In some embodiments of a linker of formula (I), X is halogen, active ester (e.g., N-succinimidyloxy, nitrophenoxy, or pentahalophenoxy), optionally substituted heteroaryl (e.g., imidazolyl, triazolyl, or tetrazolyl), or —N($R^6$)$CH_2Cl$ wherein $R^6$ is optionally substituted $C_1$-$C_6$ alkyl, optionally substituted aryl, or optionally substituted heteroaryl. In some embodiments, X is halogen. In some embodiments, X is an active ester such as succinimidyloxy. In some embodiments, X is —N($R^6$)$CH_2Cl$, wherein $R^6$ is optionally substituted aryl.

For a linker of formula (I), Z can be any functional group known in the art for conjugation. Examples of such functional groups include, without limitation, amine, aminooxy, ketone, aldehyde, maleimidyl, thiol, alcohol, azide, 1,2,4,5-tetrazinyl, trans-cyclooctenyl, bicyclononynyl, cyclooctynyl, and protected variants thereof. In some embodiments, Z is protected amine, protected aminooxy, ketone or protected ketone, aldehyde or protected aldehyde, maleimidyl, protected thiol, protected alcohol, azide, 1,2,4,5-tetrazinyl, trans-cyclooctenyl, bicyclononynyl, or cyclooctynyl. In some embodiments, Z is azide, ketone, or protected ketone.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to n of formula (I) may be combined with every description, variation, embodiment or aspect of $R^1$, $R^2$, $R^4$, X, and Z, the same as if each and every combination were specifically and individually listed. It is also understood that all descriptions, variations, embodiments or aspects of any formulae such formula (I), (II), (III), (IV), or (V), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as formula (II), (III), (IV), and (V), and are equally described, the same as if each and every description, variation, embodiment or aspect were separately and individually listed for all formulae.

Linker-Drug

In another aspect, provided is a compound of formula (II),

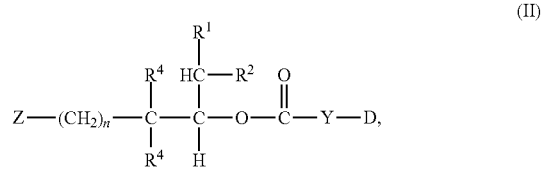

(II)

wherein n, $R^1$, $R^2$, $R^4$, X, and Z are as disclosed herein for formula (I); D is a drug; Y is absent when D is a drug connected through an amine, or Y is —N($R^6$)$CH_2$— when D is a drug connected through a phenol, alcohol, thiol, thiophenol, imidazole, or non-basic amine; wherein $R^6$ is optionally substituted $C_1$-$C_6$ alkyl, optionally substituted aryl, or optionally substituted heteroaryl. In some embodiments, the compound of formula (II) is a linker-drug prepared by combining the linker of formula (I) with a drug such as a small molecule, peptide, or protein therapeutic.

In some embodiments of compound of formula (II), Y is absent. In some embodiments, Y is —N($R^6$)$CH_2$—.

In some embodiments of compound of formula (II), suitable drugs include, without limitation, small-molecules, peptides, proteins, and nucleic acids. Examples of suitable drugs include, without limitation, antidiabetic drugs, growth promoters, antibacterials including aminoglycosides, penicillins, cephalosporins, macrolides and peptides, trimethoprim, piromidic acid, and sulfamethazine; analgesic and anti-inflammatory drugs, antiallergic and antiasthmatic drugs, antihypercholesterolemic drugs, beta-adrenergic blockers and antihypertensive drugs, antineoplastic drugs, and antiviral drugs.

Further examples of such drugs include alcohols such as paclitaxel and analogues, epothilones and analogues, camptothecin and analogues such as irinotecan, and nucleosides such as 5-fluorouracil and capecitabine. In another embodiment, the drug is a peptide comprising a serine residue. In another embodiment, the drug is a small molecule comprising an aryloyl group; examples of such drugs include SN-38, etilefrine, prenalterol, and estradiol. In another embodiment, the drug is a peptide comprising a tyrosine residue. If coupling is through S, the drug may be a small molecule comprising a thiol group. Examples of such drugs include penicillamine, captopril, and enalapril. The drug may be a small molecule comprising a thioaryl or thioheteroaryl group; examples of such drugs include 6-mercaptopurine. If coupling is through a non-basic N, the drug may be a small molecule or peptide comprising a primary or secondary amide (such as a pyroglutamate residue or other amide) or sulfonamide, or a heteroaryl group such as an indole (e.g., tryptophan) or purine. Examples include thyrotropin-releasing hormone, bombesin, luteinizing hormone-releasing hormone, follicle-stimulating releasing hormone, octreotide, 5-fluorouracil and allopurinol.

Examples of nucleic acid-based drugs include the sense strand and antisense strand of any gene from an animal, and particularly from a mammal. Such genes can be those that are already the subjects of antisense DNAs or RNAs, or small interfering RNAs that have been provided with the purpose of treating various diseases, for example genes for protein kinase C-alpha, BCL-2, ICAM-1, tumor necrosis factor alpha and the like. Also included are CpG oligonucleotide agonists of toll-like receptors. Nucleic acids may be coupled directly to the linkers or through a modified group on the nucleic acid, for example an oligonucleotide comprising a 5'- or 3'-amine modification or comprising an amine-containing base.

In some embodiments of a compound of formula (II), D is a peptide. Examples of suitable peptides include, without limitation, octreotide (SEQ ID NO:5), exenatide and variants including [N28Q]exenatide (SEQ ID NO: 1), insulin lispro (A chain: SEQ ID NO:2; B chain: SEQ ID NO:3; disulfide bridges: A6-A11, A7-B7, A20-B19), or Teduglutide ([Gly²]GLP-2) (SEQ ID NO:4), and sequence variants thereof. For example, for any of the sequences disclosed herein, both the amidated form and the non-amidated form are contemplated. As another example, for any of the amino acids, both the L-form and the D-form are contemplated. In some embodiments, the octreotide is D-Phe-Cys-Phe-D-Trp-Lys-Thr-Cys-Thr-ol (Cys2-Cys7 cyclic disulfide) (SEQ ID NO:5).

```
([N28Q]exenatide)
                                    SEQ ID NO: 1
HGEGTFTSDLSKQMEEEAVRLFIEWLKQGGPSSGAPPPS-NH₂

(A chain of insulin lispro)
                                    SEQ ID NO: 2
GIVEQCCTSICSLYQLENYCN (B chain of insulin lispro)
                                    SEQ ID NO: 3
FVNQHLCGSHLVEALYLVCGERGFFYTKPT (Teduglutide([Gly²]GLP-2))
                                    SEQ ID NO: 4
HGDGSFSDEMNTILDNLAARDFINVVLIQTKITD (octreotide; Cys2-Cys7 cyclic disulfide)
                                    SEQ ID NO: 5
FCFWKTCT
```

Conjugate

In another aspect, provided is a conjugate of formula (III),

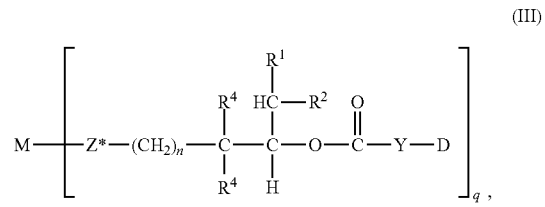

(III)

wherein n, $R^1$, $R^2$, $R^4$, D, and Y are as disclosed herein for formula (I) or (II); M is a macromolecular carrier; q is an integer from 1 to 10 when M is a soluble macromolecule, or q is a multiplicity when M is an insoluble matrix; Z* indicates coupling to M. In some embodiments, the compound of formula (III) is a conjugate of drug D releasably linked to the macromolecular carrier M through a linker of formula (I). It is understood that, when M is an insoluble matrix, a multiplicity of linker-drugs can be attached to M. For example, in some embodiments, when M is a hydrogel of formula (IV) wherein both $P^1$ and $P^2$ are 4-armed polymers, 1, 2, 3, or 4 linker-drugs can be attached to each $P^1$-$P^2$ unit. Thus, the desired multiplicity can be achieved by reacting the linker-drug with M in a suitable ratio. As such, suitable drug concentration in the volume of the matrix can be achieved.

In some embodiments of a conjugate of formula (III), molecular carrier M is a soluble macromolecule and q is an integer from 1 to 10. In some embodiments, M is an insoluble matrix and q is a multiplicity. In some embodiments, when M is an insoluble matrix, q is a multiplicity such that suitable drug concentration in the volume of the matrix can be achieved. Examples of soluble macromolecules include, without limitation, polyethylene glycol or other synthetic polymer, dextran, antibody, antibody fragment, albumin or other protein, of sufficient molecular size to inhibit efficient renal filtration as is understood in the art. For polyethylene glycols, M can be single-chain, multiple-chain, or multiple-arm of average molecular weight between 1,000 and 100,000 daltons, preferably between 1,000 and 40,000 daltons. Examples of insoluble matrices include, without limitation, hydrogel, implant, or surgical device, either in bulk or as microparticles or nanoparticles. In some embodiments, M is a soluble macromolecule. In some embodiments, M is an insoluble matrix. In some embodiments, M is a hydrogel of formula (IV) as disclosed herein.

In some embodiments of a conjugate of formula (III), the molecular carrier M comprises at least one functional group Z' cognate to Z that allows for conjugation. For example, when Z is amine, Z' is carboxylic acid, active ester, or active carbonate to yield a conjugate of formula (III) wherein Z* is amide or carbamate. As another example, when Z is azide, Z' is alkynyl, bicyclononynyl, or cyclooctynyl to yield a conjugate of formula (III) wherein Z* is 1,2,3-triazole. As another example, when Z is $NH_2O$, Z' is ketone or aldehyde to yield a conjugate of formula (III) wherein Z* is oxime. As another example, when Z is SH, Z' is maleimide or halocarbonyl to yield a conjugate of formula (III) wherein Z* is thiosuccinimidyl or thioether. Similarly, these roles of Z and Z' can be reversed to yield Z* of opposing orientation. In some embodiments, Z* comprises an amide, oxime, 1,2,3-triazole, thioether, thiosuccinimide, or ether.

Hydrogel

In another aspect, provided is a hydrogel of formula (IV),

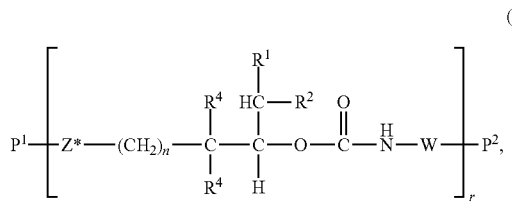

wherein n, $R^1$, $R^2$, $R^4$, and $Z^*$ are as disclosed herein for formula (I), (II), or (III);
W is absent or is

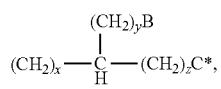

wherein each of x, y, and z is independently an integer from 0 to 6, B is —$NH_2$, —$ONH_2$, ketone, aldehyde, —SH, —OH, —$CO_2H$, carboxamide group, or a group comprising a cyclooctyne or bicyclononyne, and C* is carboxamide, thioether, thiosuccinimidyl, triazole, or oxime; and $P^1$ and $P^2$ are independently r-armed polymers of 1-40 kDa molecular weight, wherein r is an integer from 2 to 8. It is understood that $(CH_2)x$ connects to NH and C* connects to $P^2$. In some embodiments, the hydrogel of formula (IV) is degradable.

Figure 6:
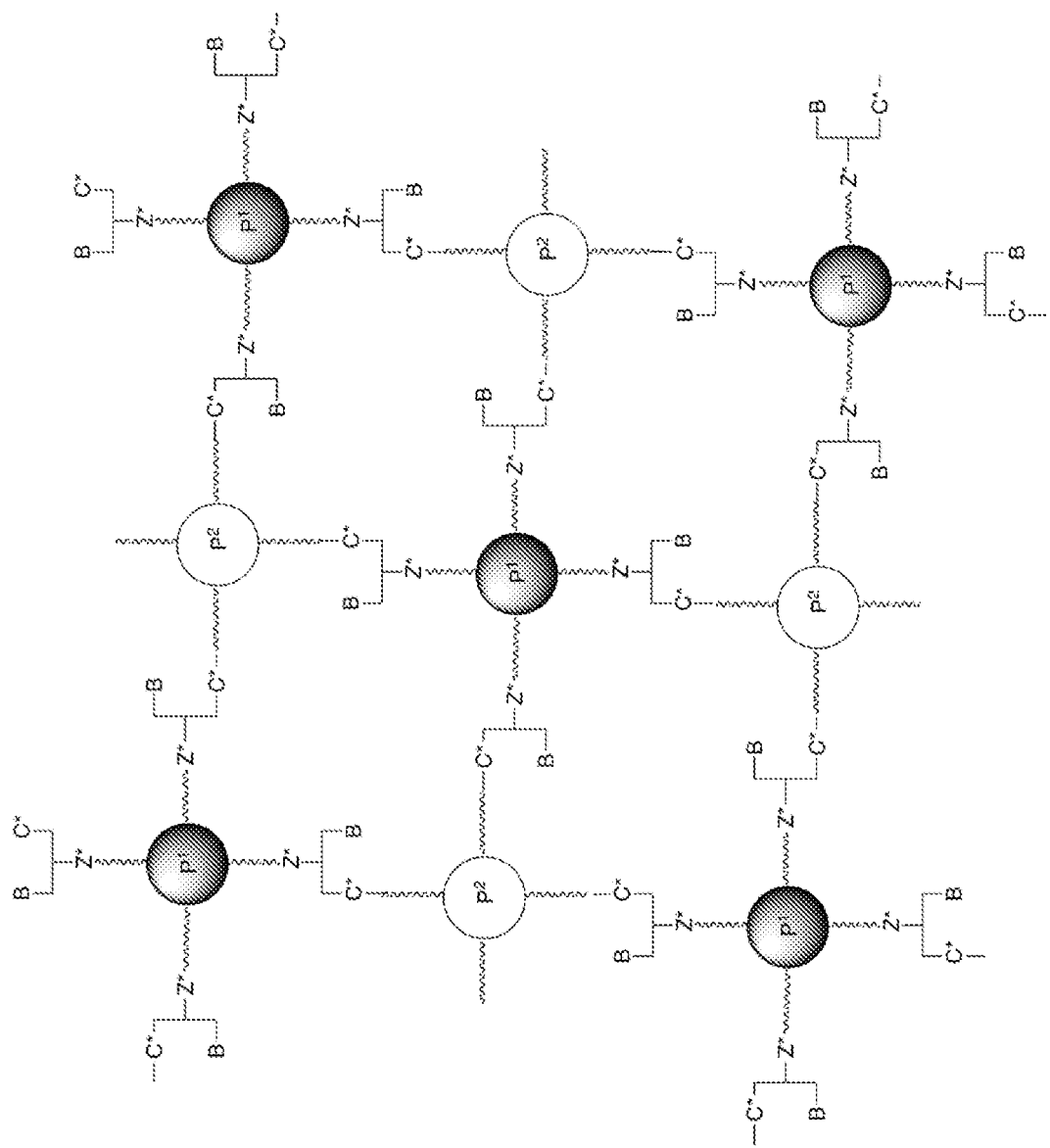
FIG. 6 shows an illustrative structure of a hydrogel comprising crosslinks of formula (IV).

In some embodiments of a hydrogel of formula (IV), $P^1$ and $P^2$ are synthetic polymers such as polyethylene glycols, dextrans, hyaluronic acids, and the like. An illustrative structure of such a hydrogel is given in FIG. 6. In these hydrogels, the linkers of formula (I) are used to crosslink polymer chains to form an insoluble 3-dimensional matrix. The crosslinks slowly cleave by non-hydrolytic beta-elimination at rates governed by groups $R^1$ and $R^2$ to give ultimately soluble polymer fragments. These hydrogels allow for attachment of the linker-drugs in several ways. When W is present, functional group B is introduced at each crosslink. As illustrated in FIG. 6, the hydrogel can be formed such that a multiplicity of B is present. Group B can then be either used directly for attachment of linker drug if B is equivalent to cognate group Z' discussed above, or B can be derivatized to introduce cognate group Z' for subsequent attachment of linker-drug to the preformed hydrogel. This is advantageous when the hydrogel needs to be made ex vivo, for example by fabrication into desired forms such as microspheres or sheets of fixed dimension. Alternatively, group B can comprise a linker-drug of formula (II) at the time the hydrogel is prepared; this is advantageous when in situ gelation is desired by injection of a liquid mixture of components prior to gel formation.

Pharmaceutical Compositions

In another aspect, provided herein are pharmaceutical compositions comprising the macromolecular carrier-drug conjugates or pharmaceutically acceptable salts thereof together with a pharmaceutically acceptable buffer and/or excipient. Buffers are chosen such that the stability of the linker is maintained during storage and upon reconstitution if required, and typically have a pH between 2 and 7, preferably between 2 and 6, and more preferably between 2 and 5. Acceptable buffers include acetic acid, citric acid, phosphoric acid, histidine, gluconic acid, aspartic acid, glutamic acid, lactic acid, tartaric acid, succinic acid, malic acid, fumaric acid, alpha-ketoglutaric acid, and the like. Excipients may include tonicity and osmolality agents such as sodium chloride; preservatives such as citric acid or a citrate salt, and parabens; antibacterials such as phenol and cresol; antioxidants such as butylated hydroxytoluene, vitamin A, C, or E, cysteine, and methionine; density modifiers such as sucrose, polyols, hyaluronic acid, and carboxymethylcellulose. These formulations can be prepared by conventional methods known to those skilled in the art, for example as described in "Remington's Pharmaceutical Science," A. R. Gennaro, ed., $17^{th}$ edition, 1985, Mack Publishing Company, Easton, PA, USA. The pharmaceutical compositions may be supplied in liquid solution or suspension, or may be provided as a solid, for example by lyophilization of a liquid composition. Such lyophils may further comprise bulking agents to ensure rapid and efficient reconstitution prior to use.

Methods of Use

In another aspect, the presently described macromolecular carrier-drug conjugates and pharmaceutical compositions comprising them may be used to treat or prevent a disease or condition in an individual. In some embodiments, provided are methods of treating a disease or condition comprising administering to the individual in need thereof a macromolecular carrier-drug conjugate described herein or a pharmaceutical compositions comprising a macromolecular carrier-drug conjugate described herein. The "individual" may be a human, or may be an animal, such as a cat, dog, cow, rat, mouse, horse, rabbit, or other domesticated animal.

Also provided are compositions containing a macromolecular carrier-drug conjugate described herein, for use in the treatment of a disease or condition. Also provided herein is the use of a macromolecular carrier-drug conjugate described herein in the manufacture of a medicament for treatment of a disease or condition.

The applicable disease or condition requiring treatment will be known by one of skill in the art from the nature of the conjugate drug. For example, exenatides and insulin may be used in the treatment of diabetes, octreotide in the treatment of acromegaly and various cancers, teduglutide in the treatment of short bowel syndrome, and SN-38 and TLR9 agonists in the treatment of cancers. Any suitable route of administration to humans and animals is envisaged by the invention, for example via intravenous, intrathecal, intraocular, subcutaneous, intraarticular, intraperitoneal, or other localized injection, or by oral administration.

Preparation of Linkers

The linkers of formula (I) may be prepared by any of several routes as illustrated in the working examples that follow. In one method, a geminal-dialkyl carbonyl compound (A) is condensed with $R^1R^2CH_2$ through the action of a base.

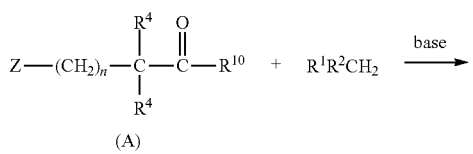

(A)

-continued

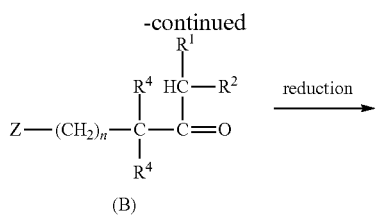

(B)

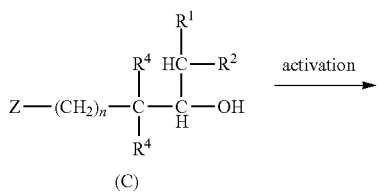

(C)

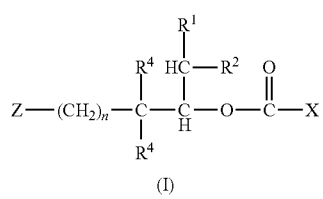

(I)

Suitable bases are those capable of deprotonating $R^1R^2CH_2$, such as potassium tert-butoxide or tert-pentoxide, butyllithium, lithium diisopropylamide, NaH, and silazide bases such as LiHMDS, NaHMDS, or KHMDS. $R^{10}$ may be H, $C_1$-$C_6$ alkoxy, or N(Me)OMe. When $R^{10}$ is H, the alcohol (C) is produced directly. When $R^{10}$ is other than H, ketone (B) is produced, which is subsequently reduced to alcohol (C). Suitable reducing agents include borohydrides such as $LiBH_4$ and $NaBH_4$, although other reducing agents well known in the art may be used depending on the nature of group Z. The alcohol (C) is then activated to produce the linker of formula (I). Typical activation conditions include conversion to the chloroformate (X=Cl) through the action of phosgene or a phosgene equivalent such as diphosgene or triphosgene; conversion to the succinimidyl carbonate (X=OSu) using N,N'-disuccinimidyl carbonate and 4-(dimethylamino)pyridine or by treatment of the chloroformate with N-hydroxysuccinimide and pyridine; and conversion to an active carbonate, for example by reaction with nitrophenyl chloroformate in the presence of a weak base such as pyridine.

Linkers of formula (I) wherein X is —N(R⁶)CH₂Cl may be prepared as disclosed in U.S. Pat. No. 8,754,190.

Z can be any functional group known in the art for conjugation, such as amine, aminooxy, ketone, aldehyde, maleimidyl, thiol, alcohol, azide, 1,2,4,5-tetrazinyl, trans-cyclooctenyl, bicyclononynyl, cyclooctynyl, and protected variants thereof. In some embodiments, Z is protected amine, protected aminooxy, ketone or protected ketone, aldehyde or protected aldehyde, maleimidyl, protected thiol, protected alcohol, azide, 1,2,4,5-tetrazinyl, trans-cyclooctenyl, bicyclononynyl, or cyclooctynyl. In some embodiments, Z is azide, ketone, or protected ketone.

Preparation of Linker-Drugs

The linker of formula (I) may be reacted with a drug D to produce the linker-drug of formula (II),

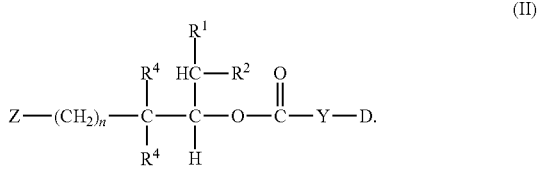

Drugs suitable for use in the invention include small-molecules, peptides, proteins, and nucleic acids. For drugs comprising basic amine groups, linkers of formula (I) wherein X is halide or active ester are reacted with the drugs, in the presence of a base in organic solvent or in buffered aqueous solution, to produce the linker-drug of formula (II). Such basic amines may be part of a small molecule drug, or may be the N-terminal amines or lysine e-amines of peptides and proteins. In the case of drugs with multiple basic amines, for example peptide and proteins, more than one linker may be attached. For synthetic peptides, the linker can be attached at specific locations during synthesis, for example either at the N-terminus by using the linker in the final coupling step, or through the use of a temporary blocking group on an internal amino acid residue that can be selectively removed; acylated with the linker is then followed by global deprotection and purification of the linker-peptide. Bases suitable to facilitate the attachment of the linker to the drug include tertiary amines, such as triethylamine or N,N-diisopropylethylamine, and guanidines, such as N,N-dimethylguanidine and 7-methyl-1,5,7-triazabicyclo[4.4.0]dec-5-ene, and others known in the art. When performed in aqueous solution, the reaction is typically performed at pH values between 7 and 10.

The linkers of formula (I) wherein X=N(R⁶)CH₂Cl may be used to link to drugs through alcohols, phenols, thiols, thiophenols, imidazoles, and non-basic nitrogen atoms, similarly to methods disclosed in U.S. Pat. No. 8,754,190.

Once the linker-drugs are prepared, any protecting groups for Z or the drug may be removed prior to conjugation using procedures well known in the art.

Preparation of Conjugates

The linker-drug of formula (II) may be used to prepare the conjugate of formula (III) by reaction of the deprotected functional group Z with a cognate reactive group bound to the macromolecular carrier M,

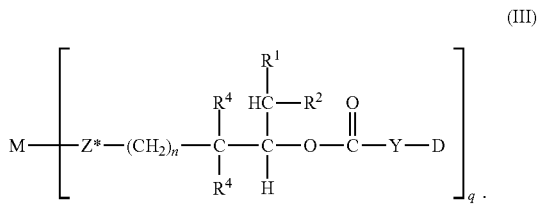

Z can be any functional group known in the art for conjugation, including amine, aminooxy, ketone, aldehyde, maleimidyl, thiol, alcohol, azide, 1,2,4,5-tetrazinyl, trans-cyclooctenyl, bicyclononynyl, or cyclooctynyl. The choice of connecting functionality will depend upon the presence of other functional groups in the drug D, but will be clear to one of skill in the art. M can be a water-soluble polymer, for example a polyethylene glycol or other synthetic polymer, dextran, antibody, antibody fragment, albumin or other protein, of sufficient molecular size to inhibit efficient renal filtration as is understood in the art. For polyethylene glycols, M can be single-chain, multiple-chain, or multiple-arm of average molecular weight between 1,000 and 100,000 daltons, preferably between 1,000 and 40,000 daltons. The polyethylene glycol comprises at least one functional group Z' cognate to Z that allows for conjugation. For example, when Z is amine, Z' is carboxylic acid, active ester, or active carbonate to yield a conjugate of formula (III) wherein Z* is amide or carbamate. As another example, when Z is azide, Z' is alkynyl, bicyclononynyl, or cyclooctynyl to yield a conjugate of formula (III) wherein Z* is 1,2,3-triazole. As another example, when Z is $NH_2O$, Z' is ketone or aldehyde to yield a conjugate of formula (III) wherein Z* is oxime. As another example, when Z is SH, Z' is maleimide or halocarbonyl to yield a conjugate of formula (III) wherein Z* is thiosuccinimidyl or thioether. Similarly, these roles of Z and Z' can be reversed to yield Z* of opposing orientation. These conjugation reactions may be performed under conditions known in the art, for example when Z=azide and Z'=cyclooctyne the conjugation occurs in any solvent wherein both components show adequate solubility, although it is known that aqueous solutions show more favorable reaction rates Similarly, M can be a water-insoluble matrix, for example a hydrogel, implant, or surgical device, either in bulk or as microparticles or nanoparticles. In this case, M comprises a multiplicity of groups Z as described above, allowing for attachment of a multiplicity of linker-drugs. While the matrix is insoluble reaction with a solution comprising the drug-linker is sufficient for conjugation to occur. For example, when the insoluble matrix is a hydrogel, either in bulk form or fabricated as microspheres or other particulate forms, a solution of the linker-drug is mixed with a suspension of the hydrogel for sufficient time to allow for the linker-drug to penetrate the porous hydrogel matrix and the conjugation reaction to occur.

Preparation of Hydrogels

In some embodiments, M is a biodegradable hydrogel of formula (IV), wherein $P^1$, $P^2$, $Z^*$, n, r, $R^1$, $R^2$, $R^4$, and W are as disclosed herein,

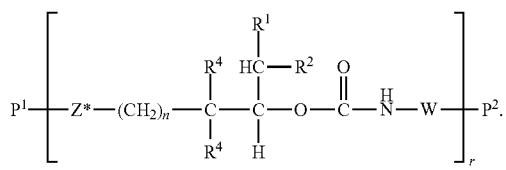

An illustrative structure of such a hydrogel comprising crosslinks of formula (IV) is given in FIG. 6. In these hydrogels, the linkers of formula (I) are used to crosslink polymer chains to form an insoluble 3-dimensional matrix. The crosslinks slowly cleave by non-hydrolytic beta-elimination at rates governed by groups $R^1$ and $R^2$ to give ultimately soluble polymer fragments. These hydrogels allow for attachment of the linker-drugs in several ways. When W is present, functional group B is introduced at each crosslink. As illustrated in FIG. 6, the hydrogel can be formed first to provide a hydrogel polymer in which a multiplicity of B is present to provide a degradable polymer that does not further comprise a linker-drug of formula (II). Group B can then be either used directly for attachment of linker-drug if B is equivalent to cognate group Z' discussed above, or B can be derivatized to introduce cognate group Z' for subsequent attachment of linker-drug to the preformed hydrogel. This is advantageous when the hydrogel needs to be made ex vivo, for example by fabrication into desired forms such as microspheres or sheets of fixed dimension. Alternatively, group B can comprise a linker-drug of formula (II) at the time the hydrogel is prepared; this is advantageous when in situ gelation is desired by injection of a liquid mixture of components prior to gel formation.

These hydrogels may be formed by mixing two multi-armed prepolymers, one having arms terminating in a group comprising the residue of a linker of formula (I) with reactive end group Z, and other having arms terminating in a group comprising cognate reactive end group Z'. In one embodiment, one prepolymer has the formula (V)

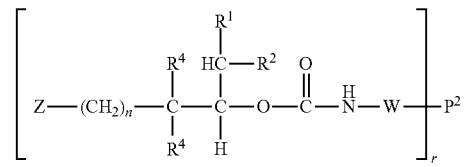

wherein the groups are as defined above, and the other prepolymer has the formula $P^1$—$(Z')_r$. When mixed in an appropriate solvent, typically an aqueous buffer at a pH of 2-7 when Z and Z' are azide/cyclooocytne, or at a pH of 6-9 when Z and Z' are an activated ester and an amine, the Z and Z' groups react to form an insoluble hydrogel matrix comprising crosslinks of formula (IV). This process may be carried out in bulk phase, or under conditions of emulsification in a mixed organic/aqueous system so as to form microparticle suspensions such as microspheres that are suitable for injection.

Certain representative embodiments are provided below:

Embodiment 1. A linker of formula (I)

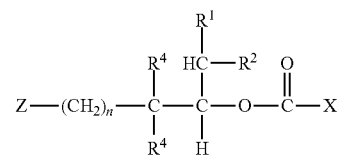

wherein n=1-6, either both $R^1$ and $R^2$ are independently electron-withdrawing groups, or one of $R^1$ and $R^2$ is an electron-withdrawing group and the other is alkyl, or H;

each $R^4$ is independently $C_1$-$C_3$, alkyl or taken together may form a 3-6 member ring;

Z is a group for attachment of the linker to a conjugation carrier; and X is a leaving group.

Embodiment 2. The linker of embodiment I wherein X is halogen, N-succinimidyloxy, nitrophenoxy, pentahalophenoxy, imidazolyl, triazolyl, or tetrazolyl.

Embodiment 3. The linker of embodiment I wherein Z is protected amine, protected aminooxy, ketone or protected ketone, aldehyde or protected aldehyde, maleimidyl, protected thiol, protected alcohol, azide, 1,2,4,5-tetrazinyl, trans-cyclooctenyl, bicyclononynyl, or cyclooctynyl.

Embodiment 4. A linker-drug of formula (II)

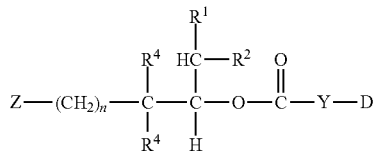

wherein Y is absent when D is a drug connected through an amine, or Y is N(R$^6$)CH$_2$ when D is a drug connected through a phenol, alcohol, thiol, thiophenol, imidazole, or non-basic amine wherein R$^6$ is optionally substituted C$_1$-C$_6$ alkyl or optionally substituted aryl or heteroaryl.

Embodiment 5. A conjugate of formula (III)

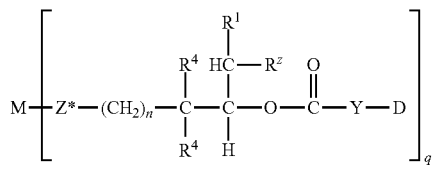

wherein M is a macromolecular carrier, Z* comprises a carboxylic amide, oxime, 1,2,3-triazole, thioether, thiosuccinimide, or ether, and q=1-multiplicity.

Embodiment 6. A hydrogel of formula (IV),

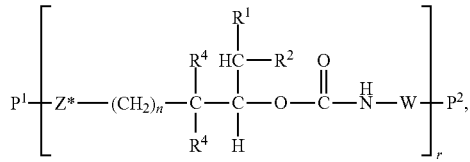

wherein P$^1$ and P$^2$ are independently r-armed polymers wherein r=2-8, and W is absent or is

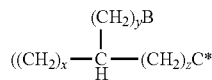

wherein x, y, and z are each independently 0-6; B is NH$_2$, ONH$_2$, ketone, aldehyde, SH, OH, CO$_2$H, or carboxamide group, and C* is carboxamide, thioether, thiosuccinimidyl, triazole, or oxime.

The following examples are offered to illustrate but not to limit the disclosure.

Example 1

Preparation of Linkers of Formula (I) Wherein Z=Azide

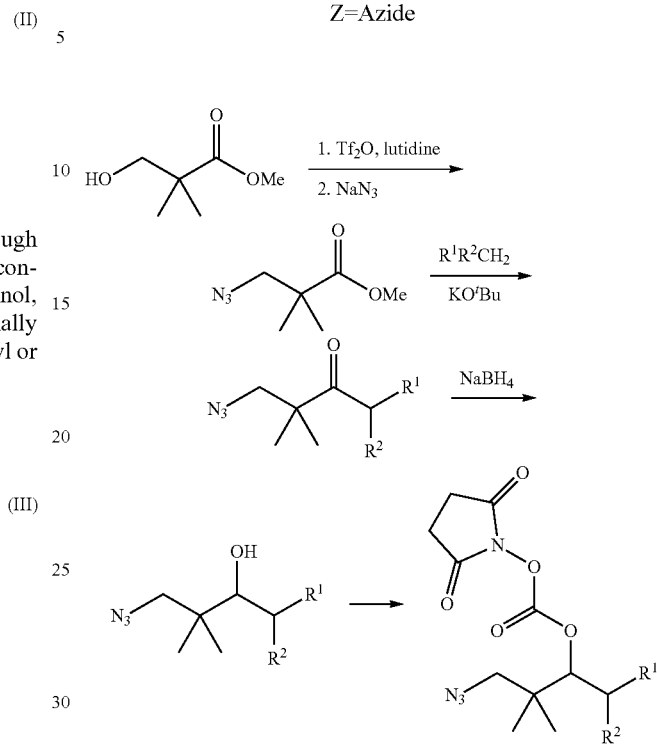

(1) 4-Azido-1-cyano-3,3-dimethyl-2-butyl succinimidyl carbonate (Formula (I) wherein n=1, R$^1$=CN, R$^2$=H, R$^4$=CH$_3$, Z=N$_3$, and X=succinimidyloxy)

A 1 M solution of potassium tert-butoxide in THF (3.5 mL, 3.5 mmol) was added to a solution of methyl 3-azido-2,2-dimethylpropionate (prepared according to Kim, Synthetic Communications; 300 mg, 1.9 mmol) and acetonitrile (0.365 mL, 7.0 mmol) in 7 mL of THF at −30° C. The mixture was stirred for 30 min at −30° C., then allowed to warm to ambient temperature over 1 h and stirred for an additional 30 min. The mixture was cooled on ice and quenched by addition of 6 N HCl (0.62 mL, 3.7 mmol), then partitioned between EtOAc and water. The aqueous phase was extract 2× with EtOAc, and the combined organics were washed with brine, dried over MgSO$_4$, filtered, and concentrated to provide the crude ketone.

Sodium borohydride (33 mg, 0.88 mmol) was added to a solution of the crude ketone (300 mg, ca. 1.75 mmol) in 7 mL of methanol. The mixture was stirred for 15 min then and quenched by addition of 6 N HCl (0.7 mL), and partitioned between EtOAc and water. The aqueous phase was extract 2× with EtOAc, and the combined organics were washed with brine, dried over MgSO$_4$, filtered, and concentrated to provide the crude alcohol. Purification on SiO$_2$ (20-40% EtOAc/hexane) provided 4-azido-1-cyano-3,3-dimethyl-2-butanol (142 mg, 0.85 mmol). $^1$H-NMR (CDCl$_3$, 300 MHz) δ 3.83-3.92 (m, 1H), 3.43 (d, J=12.1 Hz, 1H), 3.21 (d, J=12.1 Hz, 1H), 2.41-2.62 (m, 3H), 0.97 (s, 3H), and 0.96 (s, 3H).

Pyridine (136 µL, 1.7 mmol) was added dropwise to a solution of 4-azido-1-cyano-3,3-dimethyl-2-butanol (142 mg, 0.85 mmol) and triphosgene (425 mg, 1.44 mmol) in 8 mL of THF cooled on ice. The resulting suspension was allowed to warm to ambient temperature and stirred for 15 min, then filtered and concentrated to provide the crude chloroformate. This was dissolved in 8 mL of THF, cooled on ice, and treated with N-hydroxysuccinimide (291 mg, 2.5 mmol) and pyridine (204 µL, 2.53 mmol). The resulting suspension was allowed to warm to ambient temperature and stirred for 15 min, then partitioned between EtOAc and 5% KHSO$_4$. The aqueous phase was extract 2× with EtOAc, and the combined organics were washed with brine, dried over MgSO$_4$, filtered, and concentrated to provide the crude succinimidyl carbonate. Purification on SiO$_2$ (20-40% EtOAc/hexane) provided 4-azido-1-cyano-3,3-dimethyl-2-butyl succinimidyl carbonate (174 mg, 0.56 mmol). $^1$H-NMR (CDCl$_3$, 300 MHz) δ 5.03 (dd, J=7.0, 5.1, 1H), 3.27-3.41 (m, 6H), 3.43 (d, J=12.1 Hz, 1H), 3.21 (d, J=12.1 Hz, 1H), 2.41-2.62 (m, 3H), 0.97 (s, 3H), and 0.96 (s, 3H).

(2) 4-Azido-1-((N,N-dimethylamino)sulfonyl)-3,3-dimethyl-2-butyl succinimidyl carbonate (Formula (I) wherein n=1, R$^1$ =SO$_2$N(CH$_3$)$_2$, R$^2$=H, R$^4$=CH$_3$, Z=N$_3$, and X=succinimidyloxy)

A 1.43 M solution of n-butyllithium in hexane (70 mL, 100 mmol) was added to a stirred solution of N,N-dimethyl methanesulfonamide (12.33 g, 100 mmol) in 200 mL of anhydrous THF kept at −50° C. under inert atmosphere. The mixture was allowed to warm to −20° C. over 1 h, then recooled to −50° C. before adding methyl 3-azido-2,2,-dimethylpropionate (prepared according to Kim, Synthetic Communications; 7.70 g, 50 mmol). The mixture was allowed to warm to +10° C. over 2 h, then quenched with 20 mL of 6 N HCl. The mixture was diluted with methyl t-butyl ether (MTBE, 200 mL), washed 2×100 mL of water and 1×100 mL of brine, dried over MgSO$_4$, filtered, and concentrated to yield 14.05 g of crude ketone product. Chromatography on SiO$_2$ (220 g) using a step gradient of 0, 20, 30, 40, and 50% EtOAc/hexane yielded purified 4-azido-1-((N,N-dimethylamino)sulfonyl)-3,3-dimethyl-2-butanone (10.65 g, 86%) as a crystalline solid.

The above ketone was dissolved in 200 mL of methanol, cooled on ice, and treated with sodium borohydride (0.96 g, 25 mmol) for 15 min before quenching with 4 mL of 6 N HCl and concentrating. The resulting slurry was diluted with methyl t-butyl ether (MTBE, 200 mL), washed 1×100 mL of water and 1×100 mL of brine, dried over MgSO$_4$, filtered, and concentrated to yield 10.0 g of crystalline 4-azido-1-((N,N-dimethylamino)sulfonyl)-3,3-dimethyl-2-butanol.

Pyridine (10.6 mL, 132 mmol) was added over 10 min to a stirred mixture of N-hydroxysuccinimide (6.90 g, 60 mmol) and triphosgene (5.93 g, 20 mmol) in 250 mL of dichloromethane cooled on ice. The mixture was stirred for 15 min on ice, then allowed to warm to ambient temperature over 30 min. A solution of 4-azido-1-((N,N-dimethylamino)sulfonyl)-3,3-dimethyl-2-butanol (10.0 g, 40 mmol) in 20 mL of dichloromethane was added and the mixture was stirred an additional 1 h at ambient temperature. After cooling on ice, the mixture was treated with 100 mL of water and the phases were separated. The organic phase was washed 2× water, 1×5% KHSO$_4$, and 1× brine, dried over MgSO$_4$, filtered, and concentrated. The crude product was crystallized from 100 mL of 30% EtOAc/hexane, providing 4-azido-1-((N,N-dimethylamino)sulfonyl)-3,3-dimethyl-2-butyl succinimidyl carbonate (11.1 g, 71%) as a white crystalline solid.

(3) Additional Compounds of Formula (I) Prepared According to these Procedures Include 4-Azido-1-(methylsulfonyl)-3,3-dimethyl-2-butyl succinimidyl carbonate (Formula I wherein n=1, R$^1$ =SO$_2$CH$_3$, R$^2$=H, R$^4$=CH$_3$, Z=N$_3$, and X=succinimidyloxy).

4-Azido-1-((4-methylpiperidinyl)sulfonyl)-3,3-dimethyl-2-butyl succinimidyl carbonate (Formula I wherein n=1, R$^1$ =SO$_2$N(CH$_2$CH$_2$)$_2$CHCH$_3$, R$^2$=H, R$^4$=CH$_3$, Z=N$_3$, and X= succinimidyloxy). LC/MS shows [M+H]+=446.15.

4-Azido-1-(phenylsulfonyl)-3,3-dimethyl-2-butyl succinimidyl carbonate (Formula I wherein n=1, R$^1$ =SO$_2$Ph, R$^2$=H, R$^4$=CH$_3$, Z=N$_3$, and X=succinimidyloxy).

4-Azido-1-(4-chlorophenylsulfonyl)-3,3-dimethyl-2-butyl succinimidyl carbonate (Formula I wherein n=1, R$^1$ =SO$_2$PhCl, R$^2$=H, R$^4$=CH$_3$, Z=N$_3$, and X=succinimidyloxy).

4-Azido-1-(4-morpholinosulfonyl)-3,3-dimethyl-2-butyl succinimidyl carbonate (Formula I wherein n=1, R$^1$=SO$_2$N(CH$_2$CH$_2$)$_2$O, R$^2$=H, R$^4$=CH$_3$, Z=N$_3$, and X=succinimidyloxy).

4-Azido-1-(isopropylsulfonyl)-3,3-dimethyl-2-butyl succinimidyl carbonate (Formula I wherein n=1, R$^1$ =SO$_2$CH(CH$_3$)$_2$, R$^2$=H, R$^4$=CH$_3$, Z=N$_3$, and X=succinimidyloxy).

4-Azido-1-((N-ethyl-N-methylamino)sulfonyl)-3,3-dimethyl-2-butyl succinimidyl carbonate (Formula I wherein n=1, R$^1$ =SO$_2$N(CH$_3$)(CH$_2$CH$_3$), R$^2$=H, R$^4$=CH$_3$, Z=N$_3$, and X=succinimidyloxy).

4-Azido-1-((N,N-bis(2-methoxyethyl)aminosulfonyl)-3,3-dimethyl-2-butyl succinimidyl carbonate (Formula I wherein n=1, R$^1$=SO$_2$N(CH$_2$CH$_2$OCH$_3$)$_2$, R$^2$=H, R$^4$=CH$_3$, Z=N$_3$, and X=succinimidyloxy).

4-Azido-1-(4-methylphenylsulfonyl)-3,3-dimethyl-2-butyl succinimidyl carbonate (Formula I wherein n=1, R$^1$=SO$_2$PhCH$_3$, R$^2$=H, R$^4$=CH$_3$, Z=N$_3$, and X=succinimidyloxy).

Example 2

Preparation of Linkers of Formula (I)

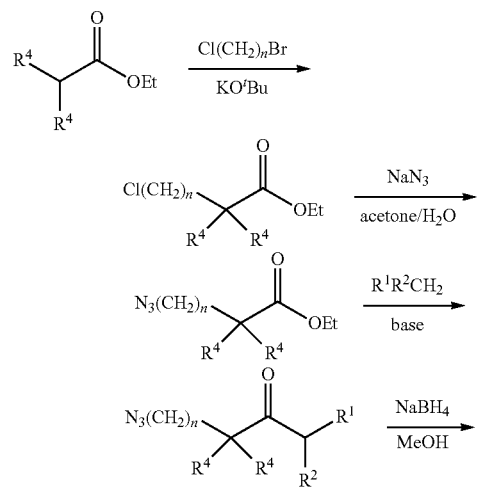

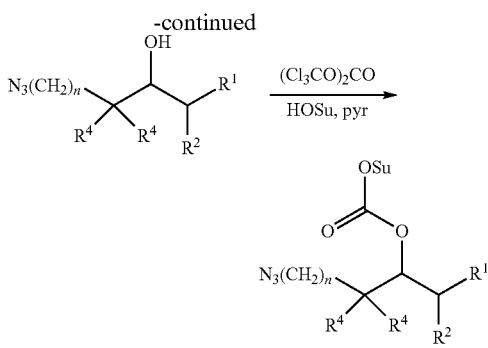

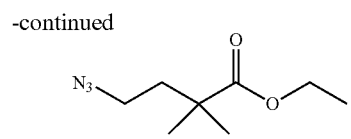

Another general method for preparation of compounds of formula (I) is illustrated for the cases wherein n=2 or 3, $R^1$=CN, $R^2$=H, both $R^4$=CH$_3$, Z=N$_3$, and X=N-succinimidyloxy.

(1) 5-Azido-1-cyano-3,3-dimethyl-2-pentyl succinimidyl carbonate (Formula I wherein n=2, $R^1$=CN, $R^2$=H, $R^4$=CH$_3$, Z=N$_3$, and X=succinimidyloxy)

(a) Ethyl 4-chloro-2,2-dimethylbutanoate

A heat-gun dried, 500-mL, round-bottom flask equipped with a stir bar, rubber septum, nitrogen inlet, and thermocouple probe was charged with iPr$_2$NH (5.30 mL, 37.4 mmol, 1.1 equiv, 0.27 M final concentration) and THF (100 mL). The reaction mixture was cooled at 0° C. while a solution of nBuLi (1.28 M in hexanes, 27.8 mL, 35.7 mmol, 1.05 equiv, 0.26 M final concentration) was added dropwise via syringe at a rate such that the internal temperature did not exceed +10° C. (~10 min). The reaction mixture was stirred at 0° C. for 15 min, cooled to −78° C. and a solution of ethyl isobutyrate (4.6 mL, 4.0 g, 34 mmol, 1.0 equiv, 0.24 M final concentration) in THF (5 mL) was added dropwise via syringe at a rate such that the internal temperature did not exceed −65° C. (~5 min). The reaction mixture was stirred at −78° C. for 45 min then a solution 1-bromo-2-chloro ethane (2.8 mL, 34 mmol, 1.0 equiv, 0.24 M final concentration) in THF (5 mL) was added at a rate such that the internal temperature did not exceed −68° C. The reaction mixture was stirred at −78° C. for 15 min, allowed to warm to 0° C., and stirred at 0° C. for 15 min. The reaction mixture was diluted with EtOAc (100 mL) and 5% KHSO$_4$ (100 mL). The aqueous phase was separated and extracted with EtOAc (3×50 mL). The aqueous phase was separated and extracted with EtOAc (3×50 mL). The combined organic phases were washed with brine, dried over MgSO$_4$, filtered, and concentrated from toluene (10 mL×2) to afford 4.85 g (27 mmol, 79%) of desired chloride as a pale yellow oil:

$^1$H NMR (CDCl3, 300 MHz) δ 4.14 (q, J=7.2 Hz, 2H), 3.43-3.57 (m, 2H), 1.94-2.19 (m, 2H), 1.27 (t, J=7.1 Hz, 3H), 1.22 (s, 6H)

(b) Ethyl 4-azido-2,2-dimethylbutanoate

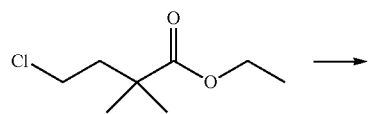

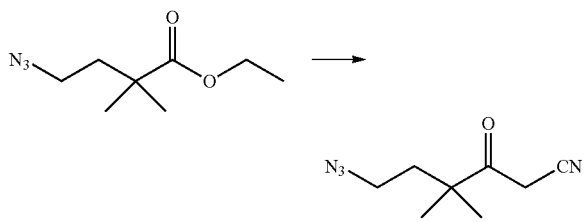

A 100-mL, round-bottomed flask equipped stir bar, rubber septum, and nitrogen inlet was charged with ethyl 4-chloro-2,2-dimethylbutanoate (2-1) (4.85 g, 27 mmol, 1.0 equiv, 0.54 M final concentration), DMSO (50 mL), and sodium azide (2.28 g, 35 mmol, 1.3 equiv, 0.70 M). The reaction mixture was stirred behind a blast shield at 70° C. for 18 h. The reaction mixture was cooled to ambient temperature and was diluted with EtOAc (200 mL) and H$_2$O (100 mL). The organic phase was separated, washed with H$_2$O (3×100 mL) and brine (100 mL), dried over MgSO$_4$, filtered, and concentrated. Purification via column chromatography (40 g silica gel cartridge; stepwise gradient elution: 0%, 5%, 10%, 20% EtOAc/hexanes) afforded 4.33 g (23.3 mmol, 87%) the desired azide as a pale yellow oil.

$^1$H NMR (CDCl3, 300 MHz) δ 4.15 (q, J=7.1 Hz, 2H), 3.22-3.35 (m, 2H), 1.81-1.96 (m, 2H), 1.27 (t, J=7.2 Hz, 3H), 1.15-1.24 (m, 6H)

(c) 5-azido-1-cyano-3,3-dimethyl-2-pentanone

A heat-gun dried, 100-mL, round-bottomed flask equipped with a stir bar, rubber septum, nitrogen inlet, and thermocouple probe was charged with THF (20 mL) and iPr$_2$NH (1.59 mL, 11.3 mmol, 2.1 equiv, 0.36 M final concentration). The solution was cooled at 0° C. while a solution of nBuLi (1.28 M in hexanes, 8.64 mL, 10.8 mmol, 2.0 equiv, 0.34 M final concentration) was added dropwise at a rate such that the internal temperature did not exceed +10° C. (~5 min), stirred at 0° C. for 10 min, and cooled at −78° C. Acetonitrile (0.59 mL, 11.3 mmol, 2.1 equiv, 0.36 M final concentration) was added dropwise via syringe at a rate such that the internal temperature did not exceed (−65° C.). The reaction mixture was stirred at −78° C. for 15 min and then a solution of ethyl 4-azido-2,2-dimethylbutanoate (1.0 g, 5.4 mmol, 1.0 equiv, 0.17 M final concentration) in THF (5 mL) was added via syringe such that the internal temperature did not exceed −65° C. (~3 min). The reaction mixture was stirred at −78° C. for 10 min, allowed to warm to 0° C., and stirred at 0° C. for 15 min. The reaction mixture was diluted with EtOAc (50 mL) and 5% KHSO$_4$ (50 mL). The aqueous layer was separated and extracted with EtOAc (3×50 mL). The combined organic phases were washed with brine (50 mL), dried over MgSO$_4$, filtered, and concentrated. Purification via column chromatography (40 g silica gel cartridge; step-wise gradient elution: 20%, 30%, 50% EtOAc/hexanes) afforded 537 mg (2.98 mmol, 55%) of desired ketone as a pale yellow oil.

$^1$H NMR (CDCl3, 300 MHz) δ 3.66 (s, 2H), 3.37 (t, J=6.7 Hz, 2H), 1.86 (t, J=6.8 Hz, 2H), 1.16-1.27 (m, 6H)

(d) 5-azido-1-cyano-3,3-dimethyl-2-pentanol

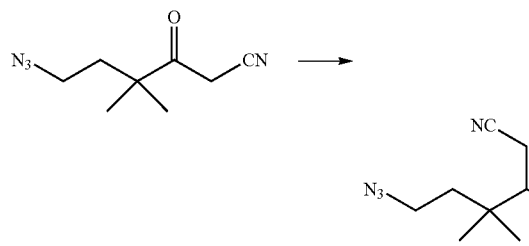

A 25-mL, round-bottomed flask equipped with a stir bar, rubber septum, and nitrogen inlet was charged with 5-azido-1-cyano-3,3-dimethyl-2-pentanone (537 mg, 2.98 mmol, 1.0 equiv, 0.25 M final concentration) and MeOH (12 mL) and cooled at 0° C. NaBH$_4$ 56 mg, 1.49 mmol, 0.5 equiv, 0.13 M final concentration) was added as a solid in a single portion. The reaction mixture was stirred at 0° C. for 30 min. The reaction mixture was diluted with EtOAc (50 mL) and 5% aq KHSO$_4$ (50 mL). The aqueous phase was separated and extracted with EtOAc (3×50 mL). The combined organic phases were washed with brine (40 mL), dried over MgSO$_4$, filtered, and concentrated. Purification via column chromatography (40 g silica gel cartridge; stepwise gradient elution: 20%, 30%, 40%, 50% EtOAc/hexanes) afforded 482 mg (2.64 mmol, 89%) of desired alcohol as a pale yellow oil.

$^1$H NMR (CDCl3, 300 MHz) δ 3.76 (ddd, J=9.1, 5.4, 3.4 Hz, 1H), 3.34-3.50 (m, 2H), 2.38-2.64 (m, 3H), 1.68-1.82 (m, 1H), 1.50 (ddd, J=14.1, 7.4, 6.6 Hz, 1H), 0.96 (s, 3H), 0.94 (s, 3H)

(e) 5-azido-1-cyano-3,3-dimethyl-2-pentyl succinimidyl carbonate

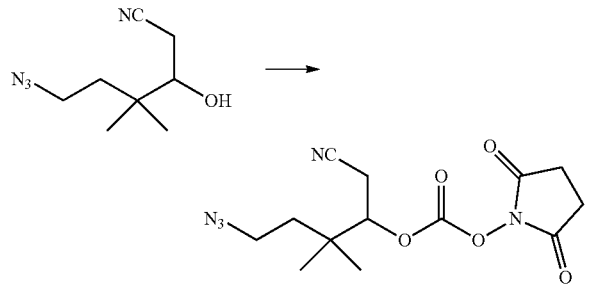

A heat-gun dried, 50-mL, round-bottomed flask equipped with stir bar, rubber septum, and nitrogen inlet was charged with NHS (455 mg, 3.96 mmol, 1.5 equiv, 211 mM final concentration), DCM (17 mL), and triphosgene (392 mg, 1.32 mmol, 0.5 equiv, 70.4 mM final concentration) and the cooled at 0° C. The reaction mixture was cooled at 0° C. while pyridine (0.774 mL, 8.71 mmol, 3.3 equiv, 464 mM final concentration) was added dropwise via syringe. The reaction mixture was allowed to warm to ambient temperature and stir at ambient temperature for 30 min. A solution of 5-azido-1-cyano-3,3-dimethyl-2-pentanol (482 mg, 2.64 mmol, 1.0 equiv, 150 mM final concentration) in THF (1 mL) was added dropwise via syringe. The reaction mixture was stirred at ambient temperature for 1 h, cooled at 0° C., and quenched with the by the addition of H$_2$O (10 mL). The reaction mixture was further diluted with EtOAc (50 mL) and H$_2$O (50 mL). The organic phase was separated and washed with water (50 mL), 5% aq KHSO$_4$, brine (50 mL), dried over MgSO$_4$, filtered, and concentrated. Purification via column chromatography (40 g silica gel cartridge; stepwise gradient elution: 25%, 30%, 35%, 40% acetone/hexanes) afforded 636 mg (1.96 mmol, 75% yield) of desired activated linker as a white solid.

$^1$H NMR (CDCl3, 300 MHz) δ 4.90-4.99 (m, 1H), 3.32-3.50 (m, 2H), 2.84-2.88 (m, 4H), 2.66-2.82 (m, 2H), 1.58-1.80 (m, 2H), 1.08 (s, 6H).

(2) 6-Azido-1-cyano-3,3-dimethyl-2-hexyl succinimidyl carbonate (Formula I wherein n=3, $R^1$=CN, $R^2$=H, $R^4$=CH$_3$, Z=N$_3$, and X=succinimidyloxy)

(a) ethyl 5-chloro-2,2-dimethylpentanoate

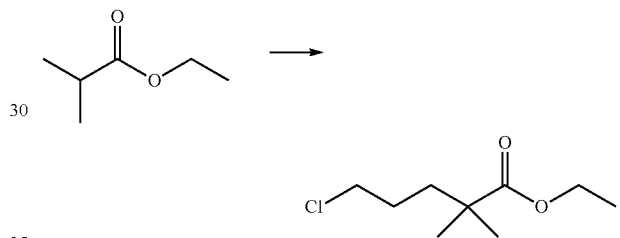

A heat-gun dried, 500-mL, round-bottom flask equipped with a stir bar, rubber septum, nitrogen inlet, and thermocouple probe was charged with iPr$_2$NH (5.30 mL, 37.4 mmol, 1.1 equiv, 266 mM final concentration) and THF (100 mL). The reaction mixture was cooled at 0° C. while a solution of nBuLi (1.28 M in hexanes, 27.8 mL, 35.7 mmol, 1.05 equiv, 254 mM final concentration) was added dropwise via syringe at a rate such that the internal temperature did not exceed +10° C. (~10 min). The reaction mixture was stirred at 0° C. for 15 min, cooled to −78° C. and a solution of ethyl isobutyrate (4.60 mL, 4.0 g, 34.0 mmol, 1.0 equiv, 242 mM final concentration) in THF (5 mL) was added dropwise via syringe at a rate such that the internal temperature did not exceed −65° C. (~5 min). The reaction mixture was stirred at −78° C. for 45 min then a solution 1-bromo-3-chloro propane (3.37 mL, 34.0 mmol, 1.0 equiv, 242 mM final concentration) in THF (5 mL) was added at a rate such that the internal temperature did not exceed −68° C. The reaction mixture was stirred at −78° C. for 15 min, allowed to warm to 0° C., and stirred at 0° C. for 15 min. The reaction mixture was diluted with EtOAc (100 mL) and 5% KHSO$_4$ (100 mL). The aqueous phase was separated and extracted with EtOAc (3×50 mL). The combined organic phases were washed with brine, dried over MgSO$_4$, filtered, and concentrated from toluene (10 mL×2). afforded 6.17 g (32.0 mmol, 90%) of desired chloride as a pale yellow oil:

$^1$H NMR (CDCl3, 300 MHz) δ 4.13 (q, J=7.2 Hz, 2H), 3.49-3.56 (m, 2H), 1.62-1.83 (m, 4H), 1.26 (t, J=7.1 Hz, 3H), 1.17-1.22 (m, 6H)

(b) ethyl 5-azido-2,2-dimethylpentanoate

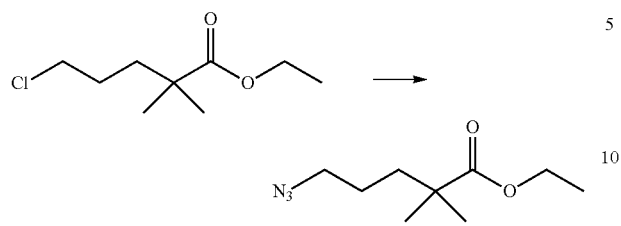

A 100-mL, round-bottomed flask equipped stir bar, rubber septum, and nitrogen inlet was charged with ethyl 5-chloro-2,2-dimethylpentanoate (6.17 g, 32.0 mmol, 1.0 equiv, 533 mM final concentration), DMSO (60 mL), and sodium azide (2.7 g, 42 mmol, 1.3 equiv, 690 mM). The reaction mixture was stirred behind a blast shield at 70° C. for 18 h. The reaction mixture was cooled to ambient temperature and was diluted with EtOAc (200 mL) and H$_2$O (100 mL). The organic phase was separated, washed with H$_2$O (3×100 mL) and brine (100 mL), dried over MgSO$_4$, filtered, and concentrated. Purification via column chromatography (40 g silica gel cartridge; stepwise gradient elution: 0%, 5%, 10%, 20% EtOAc/hexanes) afforded 5.40 g (27.1 mmol, 85%) of desired azide as a pale yellow oil.

$^1$H NMR (CDCl3, 300 MHz) δ 4.13 (q, J=7.0 Hz, 2H), 3.26 (t, J=5.9 Hz, 2H), 1.46-1.65 (m, 4H), 1.26 (t, J=7.2 Hz, 3H), 1.19 (s, 6H).

(c) 6-azido-J-cyano-3,3-dimethyl-2-hexanone

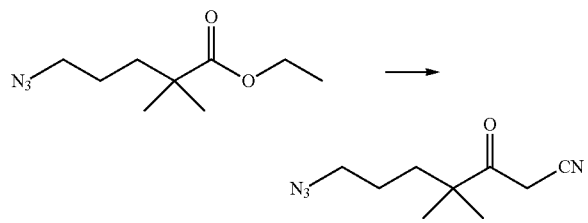

A heat-gun dried, 100-mL, round-bottomed flask equipped with a stir bar, rubber septum, nitrogen inlet, and thermocouple probe was charged with THF (40 mL), iPr$_2$NH (3.0 mL, 21 mmol, 2.1 equiv, 320 mM final concentration). The solution was cooled at 0° C. while a solution of nBuLi (1.28 M in hexanes, 15.4 mL, 20.0 mmol, 2.0 equiv, 305 mM final concentration) was added dropwise at a rate such that the internal temperature did not exceed +10° C. (~5 min), stirred at 0° C. for 10 min, and cooled at −78° C. Acetonitrile (1.10 mL, 21.0 mmol, 2.1 equiv, 322 mM final concentration) was added dropwise via syringe at a rate such that the internal temperature did not exceed (−65° C.). The reaction mixture was stirred at −78° C. for 15 min and then a solution of ethyl 5-azido-2,2-dimethylpentanoate (2.04 g, 10.0 mmol, 1.0 equiv, 153 mM final concentration) in THF (4 mL) was added via syringe such that the internal temperature did not exceed −65° C. (~3 min). The reaction mixture was stirred at −78° C. for 10 min, allowed to warm to 0° C., and stirred at 0° C. for 15 min. The reaction mixture was diluted with EtOAc (50 mL) and 5% KHSO$_4$ (50 mL). The aqueous layer was separated and extracted with EtOAc (3×50 mL). The combined organic phases were washed with brine (50 mL), dried over MgSO$_4$, filtered, and concentrated. Purification via column chromatography (40 g silica gel cartridge; step-wise gradient elution: 15%, 20%, 30%, 40% EtOAc/hexanes) afforded 1.18 g (6.07 mmol, 59%) of desired ketone as a pale yellow oil.

$^1$H NMR (CDCl3, 300 MHz) δ 3.61 (d, J=0.4 Hz, 2H), 3.32 (t, J=6.3 Hz, 2H), 1.42-1.68 (m, 5H), 1.17-1.24 (m, 6H).

(d) 6-azido-1-cyano-3,3-dimethyl-2-hexanol

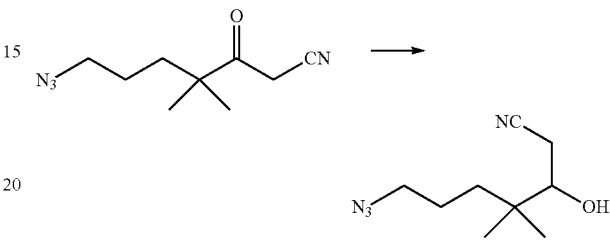

A 25-mL, round-bottomed flask equipped with a stir bar, rubber septum, and nitrogen inlet was charged with 6-azido-1-cyano-3,3-dimethyl-2-hexanone (1.18 g, 6.08 mmol, 1.0 equiv, 243 mM final concentration) and MeOH (25 mL) and cooled at 0° C. NaBH$_4$ (114 mg, 3.04 mmol, 0.5 equiv, 122 mM final concentration) was added as a solid in a single portion. The reaction mixture was stirred at 0° C. for 30 min. The reaction mixture was diluted with EtOAc (50 mL) and 5% aq KHSO$_4$ (50 mL). The aqueous phase was separated and extracted with EtOAc (3×50 mL). The combined organic phases were washed with brine (40 mL), dried over MgSO$_4$, filtered, and concentrated. Purification via column chromatography (40 g silica gel cartridge; stepwise gradient elution: 20%, 30%, 40%, 50% EtOAc/hexanes) afforded 1.1 g (5.61 mmol, 97%) of desired linker alcohol as a pale yellow oil.

$^1$H NMR (CDCl3, 300 MHz) δ 3.68-3.79 (m, 1H), 3.30 (t, J=6.6 Hz, 2H), 2.39-2.60 (m, 2H), 2.23-2.29 (m, 1H), 1.20-1.68 (m, 4H), 0.93 (s, 3H), 0.92 (s, 3H)

(e) 6-azido-1-cyano-3,3-dimethyl-2-hexyl succinimidyl carbonate

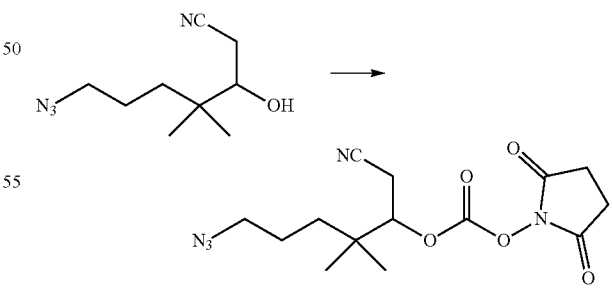

A heat-gun dried, 50-mL, round-bottomed flask equipped with stir bar, rubber septum, and nitrogen inlet was charged with NHS (440 mg, 3.83 mmol, 1.5 equiv, 217 mM final concentration), DCM (17 mL), and triphosgene (378 mg, 1.28 mmol, 0.5 equiv, 72 mM final concentration) and the cooled at 0° C. The reaction mixture was cooled at 0° C. while pyridine (0.68 mL, 8.4 mmol, 3.3 equiv, 48 mM final concentration) was added dropwise via syringe. The reaction mixture was allowed to warm to ambient temperature and stir at ambient temperature for 30 min. A solution of 6-azido-1-cyano-3,3-dimethyl-2-hexanol (500 mg, 2.55 mmol, 1.0 equiv, 144 mM final concentration) in THF (1 mL) was added dropwise via syringe. The reaction mixture was stirred at ambient temperature for 1 h, cooled at 0° C., and quenched with the by the addition of $H_2O$ (10 mL). The reaction mixture was further diluted with EtOAc (50 mL) and $H_2O$ (50 mL). The organic phase was separated and washed with water (50 mL), 5% aq $KHSO_4$, brine (50 mL), dried over $MgSO_4$, filtered, and concentrated. Purification via column chromatography (40 g silica gel cartridge; stepwise gradient elution: 25%, 30%, 35%, 40% acetone/hexanes) afforded 638 mg (1.89 mmol, 74% yield) of desired activated linker as a white solid.

$^1H$ NMR (CDCl3, 300 MHz) δ 4.93 (dd, J=7.1, 5.3 Hz, 1H), 3.32 (s, 2H), 2.86 (s, 4H), 2.71-2.79 (m, 2H), 1.29-1.72 (m, 4H), 1.05 (s, 3H), 1.04 (s, 3H).

Example 3

Preparation of Linkers of Formula (I) Wherein Z=Protected Ketone

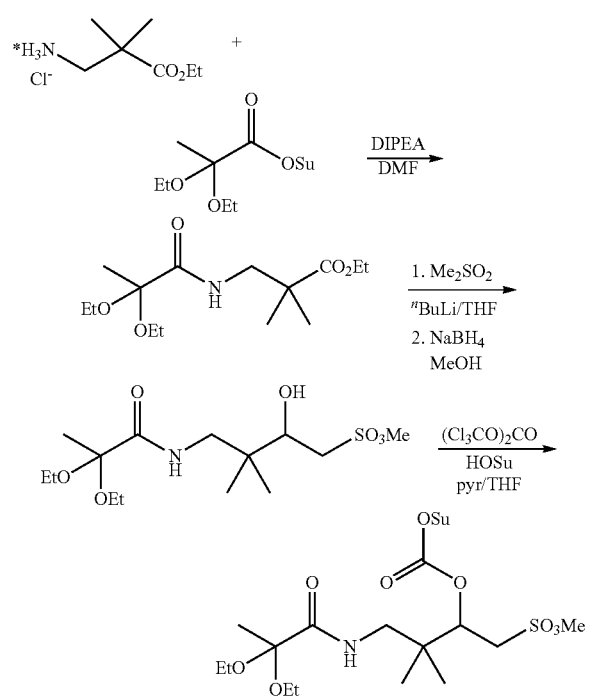

Succinimidyl 2,2-diethoxypropanoate: Concentrated $H_2SO_4$ (0.5 mL) was added to an ice-cold mixture of pyruvic acid (8.8 g, 100 mmol) and triethyl orthoformate (40 mL, 240 mmol. The mixture was stirred for 30 min on ice, then diluted with $CH_2Cl_2$ and washed twice with cold water followed by brine, dried over $MgSO_4$, filtered, and concentrated to yield crude 2,2-diethoxypropanoic acid (11.16 g, 69 mmol). This was dissolved in 250 mL of $CH_2Cl_2$ and treated with N-hydroxysuccinimide (8.7 g, 76 mmol) followed by dicyclohexylcarbodiimide (15.6 g, 76 mmol) for 2 h. The thick white slurry was filtered to remove dicyclohexylurea, then passed through a pad of silica gel to remove most yellow color. The silica gel was rinsed with 1:1 EtOAc/hexane, and the combined eluates were concentrated. The residue was crystallized from hot 20% EtOAc/hexane to provide a first crop of the succinimidyl ester (11.73 g, 45 mmol) as white crystals. Chromatography of the mother liquors on $SiO_2$ (0-60% EtOAc/hexane) followed by crystallization provided an additional crop of product, giving a total of 13.0 g of product (50% overall from pyruvic acid).

Ethyl 3-[(2,2-diethoxypropanoyl)amino]-2,2-dimethylpropanoate:A solution of ethyl 3-amino-2,2-dimethylpropanoate (CombiBlocks; 1.82 g, 10 mmol) and succinimidyl 2,2-diethoxypropanoate (2.6 g, 10 mmol) in 10 mL of DMF was treated with N,N-diisopropylethylamine (3.5 mL, 20 mmol) for 1 h at ambient temperature. The mixture was diluted with EtOAc and washed successively with water, 5% $KHSO_4$, sat. aq. $NaHCO_3$, and brine, then dried over $MgSO_4$, filtered, and concentrated. Chromatography on $SiO_2$ (0-70% MTBE/hexane) provided the product ester (2.48 g, 86%) as a colorless oil.

Conversion to the succinimidyl carbonate followed the procedures outlined for other linkers above.

Example 4

Preparation of Linkers of Formula (I) Wherein $X=N(R^6)CH_2Cl$

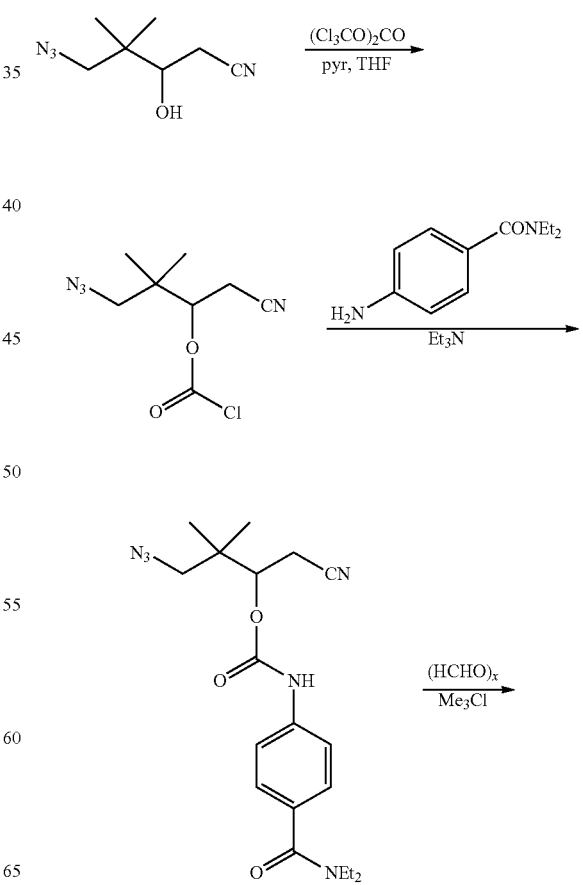

-continued

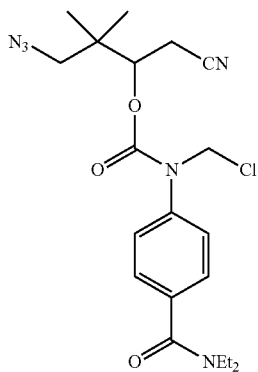

Step 1. 4-azido-1-cyano-3,3-dimethyl-2-butyl 4-(N,N-diethylcarboxamido)phenylcarbamate. Pyridine was added to a solution of 4-azido-1-cyano-3,3-dimethyl-2-butanol and triphosgene in THF. After 15 min, the mixture was filtered and concentrated. The residue was dissolved in $CH_2Cl_2$ and treated with N,N-diethyl 4-aminobenzamide and triethylamine. After 1 h, the mixture was diluted with $CH_2Cl_2$ and washed with 5% $KHSO_4$, water, and brine, then dried over $MgSO_4$, filtered, and evaporated. The product was crystallized.

Step 2. N-chloromethyl 4-azido-1-cyano-3,3-dimethyl-2-butyl 4-(N,N-diethylcarboxamido)-phenylcarbamate. A mixture of the carbamate of Step 1 (1 mmol), paraformaldehyde (120 mg), chlorotrimethylsilane (0.5 mL), and 1,2-dichloroethane (4 mL) was sealed in a screw-cap vial and heated at 50° C. for 12 h. After cooling, the mixture was concentrated and the residue was redissolved in 10 mL of MTBE, filtered, and reconcentrated to yield the N-chloromethyl carbamate as a colorless oil.

Example 5

Preparation of Compounds of Formula (II) Wherein Z=Azide

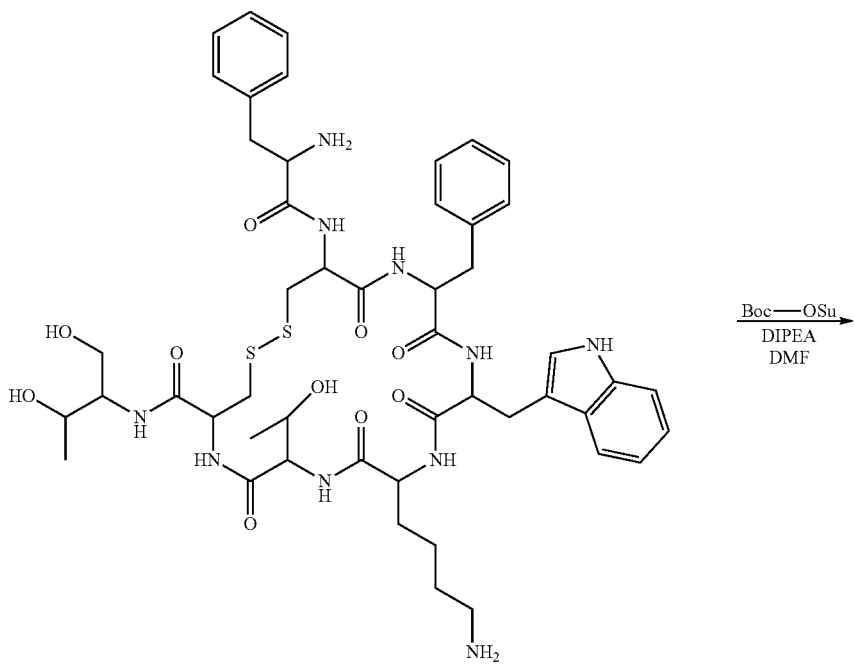

31
-continued
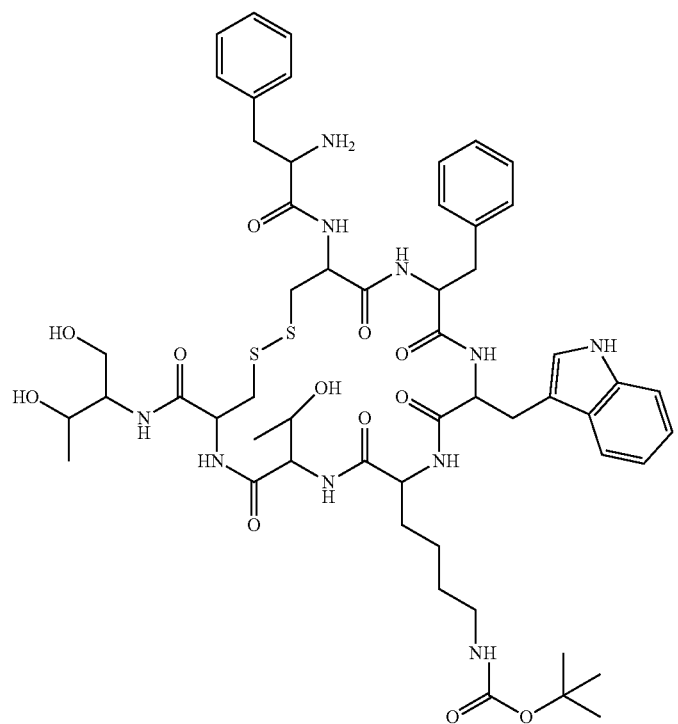 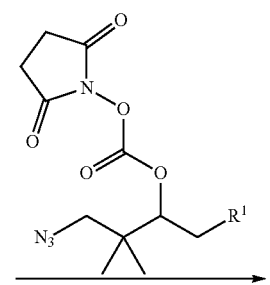
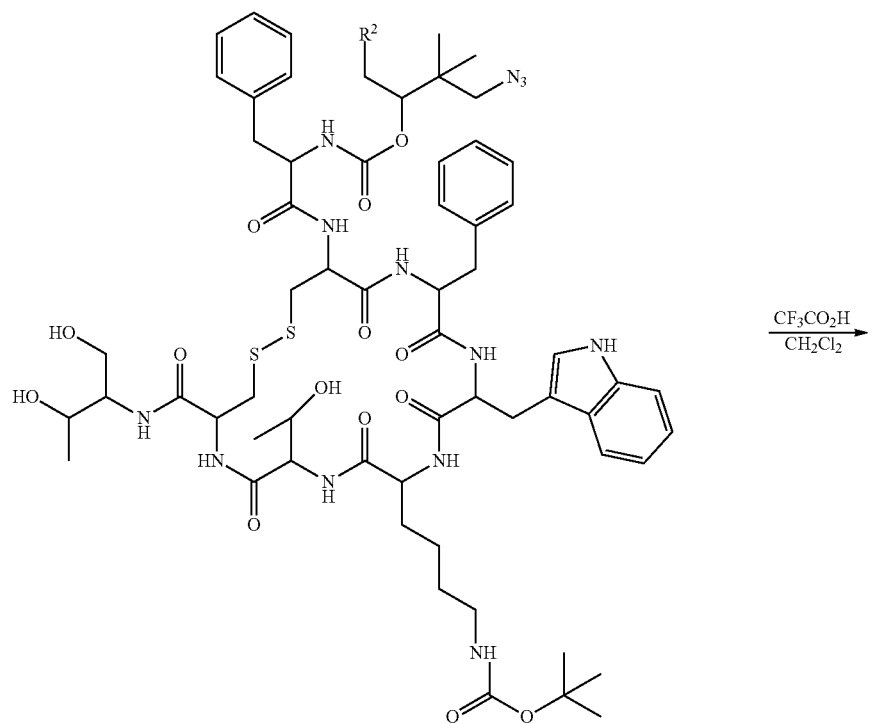

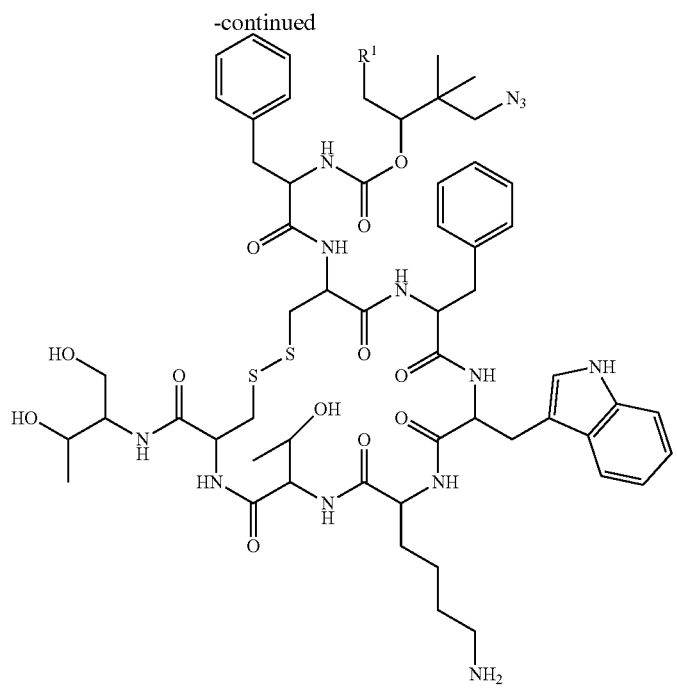

A method for preparation of compounds of formula (II) is illustrated wherein n=1, $R^4$=$CH_3$, Z=$N_3$, and D is octreotide connected through the alpha-amino group of $Phe^1$.

Boc-octreotide. A 58.4 mg/mL solution of t-butyl succinimidyl carbonate (385 µL) was added to a mixture of octreotide acetate (128 mg) and N,N-diisopropylethylamine (0.2 mL) in 2 mL of amine-free N,N-dimethylformamide. After 4 h, HPLC analysis indicated the presence of 91.6% mono-Boc-octreotide, 3.0% di-Boc-octreotide, and 5.4% octreotide. UV spectrophotometric analysis indicated a total octreotide concentration of 43.5 mM. This solution was used without purification.

General procedure. Compounds of Formula (I) were dissolved in amine-free DMF at 40 mM. An aliquot of Boc-octreotide from above (500 µL, 21.8 µmol total octreotide) was mixed with the solution of the compound of Formula (I) (540 µL, 21.6 µmol) and kept for 16 h at ambient temperature. The reaction was diluted into 5 mL of ice-cold 0.1 M acetic acid, and the precipitated linker-peptide was collected by centrifugation. The pelleted material was dissolved in 4 mL of methanol and purified by preparative HPLC ($C_{18}$, 20-80% MeCN/$H_2O$/0.1% TFA). After drying, the purified material was dissolved in 1 mL of ice-cold 95:5 trifluoroacetic acid/water to remove the Boc group, kept 10 min, then precipitated by addition of 10 mL of cold ether and dried.

Compounds of Formula (II) prepared according to this method include:

Nα-[(4-azido-1-((N,N-dimethylamino)sulfonyl)-3,3-dimethyl-2-butoxy)carbonyl]octreotide (n=1, $R^1$=$SO_2N(CH_3)_2$, $R^2$=H, $R^4$=$CH_3$, Z=$N_3$, D=octreotide connected through the a-amino group). Yield 23.6 mg (84%), LC-MS shows $[M+H]^+$=1295.75 (expect 1295.6).

Nα-[(4-azido-1-((N-ethyl-N-methylamino)sulfonyl)-3,3-dimethyl-2-butoxy)carbonyl]octreotide (n=1, $R^1$=$SO_2N(CH_3)(CH_2CH_3)$, $R^2$=H, $R^4$=$CH_3$, Z=$N_3$, D=octreotide connected through the a-amino group). Yield 21.6 mg, LC-MS shows $[M+H]^+$=1309.75 (expect 1309.6).

Nα-[(4-azido-1-((morpholinosulfonyl)-3,3-dimethyl-2-butoxy)carbonyl]octreotide (n=1, $R^1$=$SO_2N(CH_2CH_2)_2O$, $R^2$=H, $R^4$=$CH_3$, Z=$N_3$, D=octreotide connected through the a-amino group). Yield 19.9 mg (84%), LC-MS shows $[M+H]^+$=1337.7 (expect 1337.6).

Nα-[(4-azido-1-((N,N-bis(2-methoxyethyl)aminosulfonyl)-3,3-dimethyl-2-butoxy)carbonyl]octreotide (n=1, $R^1$=$SO_2N(CH_2CH_2OCH_3)_2$, $R^2$=H, $R^4$=$CH_3$, Z=$N_3$, D=octreotide connected through the a-amino group). Yield 35.4 mg, LC-MS shows $[M+H]^+$=1383.8 (expect 1383.7).

Nα-[(4-azido-1-((isopropylsulfonyl)-3,3-dimethyl-2-butoxy)carbonyl]octreotide (n=1, $R^1$=$SO_2CH(CH_3)_2$, $R^2$=H, $R^4$=$CH_3$, Z=$N_3$, D=octreotide connected through the a-amino group). Yield 16.8 mg, LC-MS shows $[M+H]^+$=1294.7" (expect 1294.6).

Nα-[(4-azido-1-(1-cyano-3,3-dimethyl-2-butoxy)carbonyl]octreotide (n=1, $R^1$=CN, $R^2$=H, $R^4$=$CH_3$, Z=$N_3$, D=octreotide connected through the a-amino group).

Nα-[(4-azido-1-(1-(methylsulfonyl)-3,3-dimethyl-2-butoxy)carbonyl]octreotide (n=1, Rt=$SO_2CH_3$, $R^2$=H, $R^4$=$CH_3$, Z=$N_3$, D=octreotide connected through the a-amino group).

N$^\alpha$-linker-[Gln$^{28}$]-exenatide

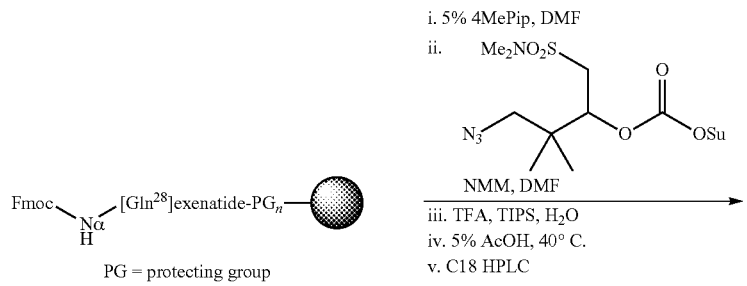

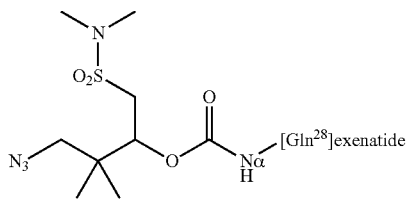

N$^\alpha$-{4-Azido-3,3-dimethyl-1-[(N,N-dimethyl)aminosulfonyl]-2-butyloxycarbonyl}-[Gln$^{28}$]exenatide. In a 25 mL fritted SPE column, protected [Gln$^{28}$]exenatide (Fmoc α-amine) on Rink amide resin (0.63 meq/g substitution, 0.12 mmol peptide/g peptide-resin, 1.00 g peptide-resin, 0.12 mmol peptide) was swollen in 10 mL of DMF for 30 min at ambient temperature. DMF was removed by syringe filtration using a F/F Luer adapter and a 12 mL syringe, and the swollen resin was treated with 5% 4-methylpiperidine in DMF (2×10 mL, 5 min each; then 2×10 mL, 20 min each). The Fmoc-deprotected resin was then washed with DMF (10×10 mL), and supernatants were removed by syringe filtration. The washed resin was suspended in 8.4 mL DMF and treated with 3.6 mL of O-{4-azido-3,3-dimethyl-1-[(N,N-dimethyl)aminosulfonyl]-2-butyl}-O'-succinimidyl carbonate (0.10 M in DMF, 0.36 mmol, 30 mM final concentration) and 4-methylmorpholine (40 μL, 0.36 mmol, 30 mM final concentration). The reaction mixture was agitated using an orbital shaker. After 20 h, the supernatant was removed by syringe filtration, and the resin was washed with successively DMF (5×15 mL) and CH$_2$Cl$_2$ (5×15 mL). Kaiser test was negative for free amines in the intermediate linker-modified resin. The resin was then treated with 10 mL of precooled (0° C.) 90:5:5 TFA:TIPS:H$_2$O while gently agitating on an orbital shaker. After 2 h, the resin was vacuum filtered and washed with TFA (2×1.5 mL). The filtrate was concentrated by rotary evaporation to ~6 mL. The crude linker-peptide was precipitated by dropwise addition of the TFA concentrate to 40 mL of −20° C. MTBE in a tared 50 mL Falcon tube. After incubating at −20° C. for 10 min, the crude linker-peptide suspension was pelleted by centrifugation (3000×g, 2 min, 4° C.), and the supernatant was decanted. The resulting pellet was suspended in 40 mL of −20° C. MTBE, vortexed to mix, centrifuged, and decanted as above. After drying under high vacuum, the pellet was isolated as an off-white solid (575 mg) that was then dissolved in 8 mL of 5% AcOH (~70 mg/mL). After heating in a 50° C. water bath for 45 min, the solution was purified by Preparative C18 HPLC to provide 13 mL of the title compound (3.33 mM, 43 μmol by A$_{280}$) as an aqueous solution. Lyophilization provided 235 mg of a white solid.

C18 HPLC purity determined at 280 nm: 90.0% (RV=11.47 mL)

M$_{av}$: 4476.9 calc; 4476 obsd

Example 6
Preparation of Compounds of Formula (II) Wherein Z=Ketone
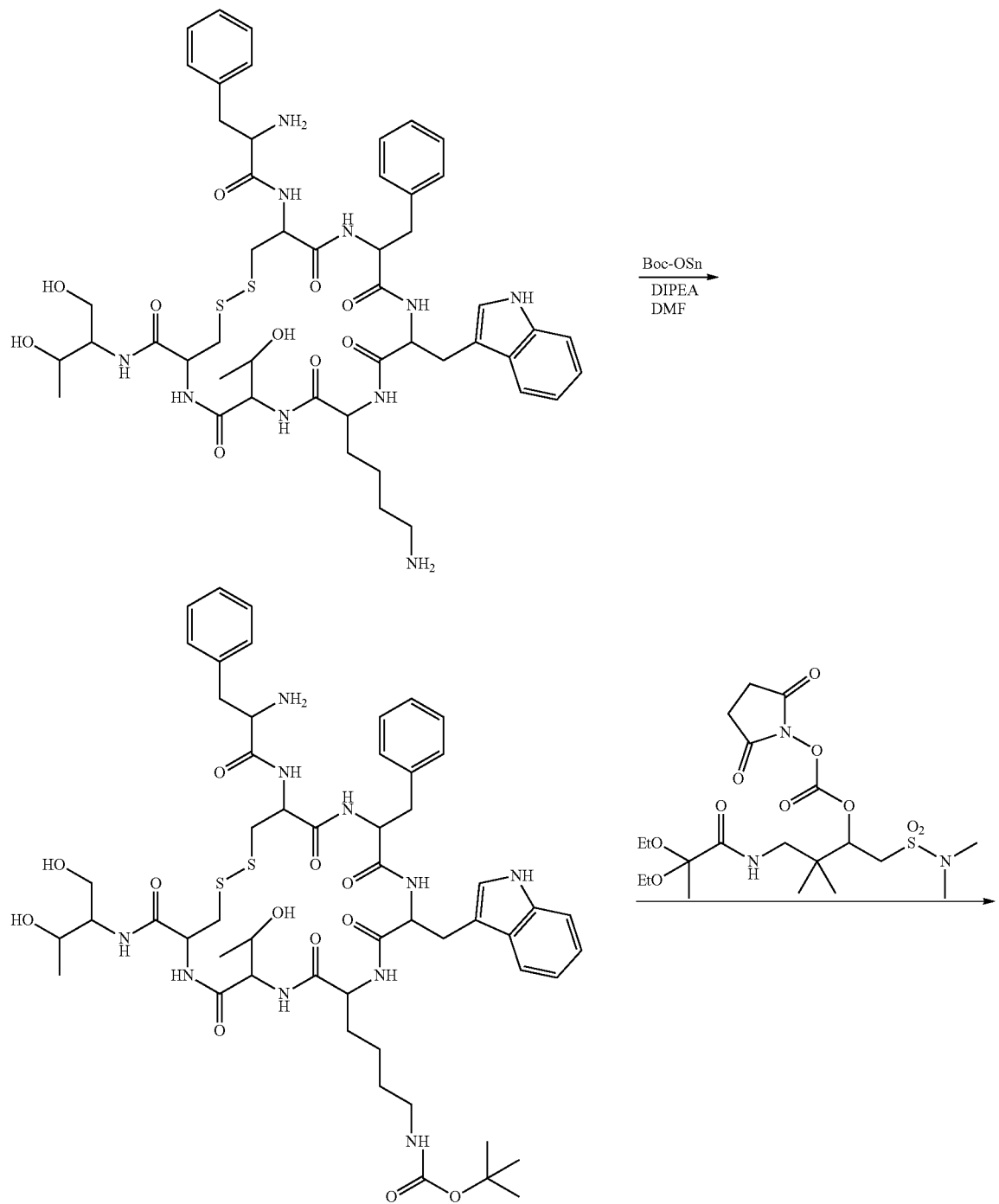

-continued

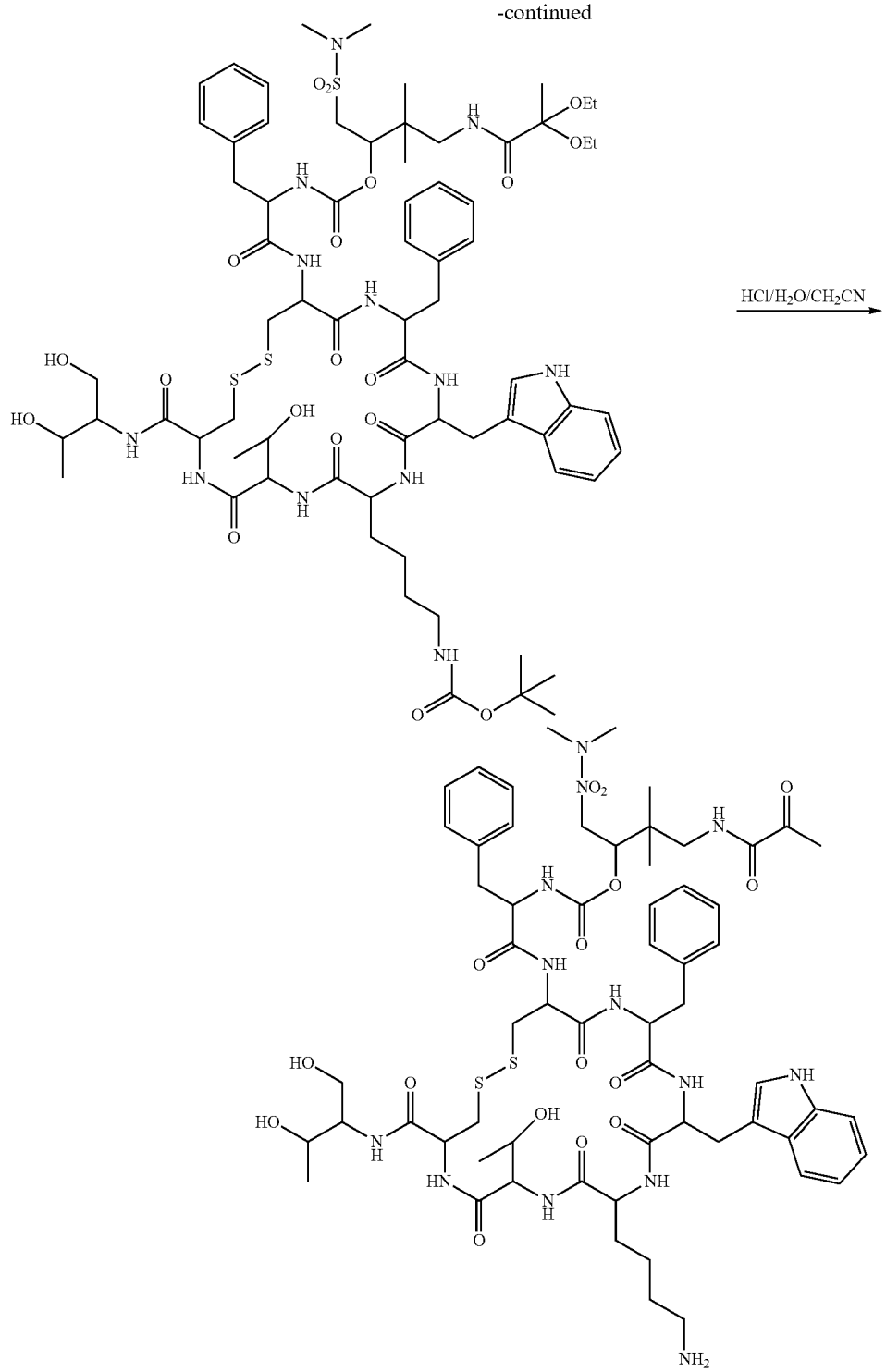

The preparation of compounds of Formula (II) wherein Z=ketone is illustrated by an example wherein n=1, $R^1$=SO$_2$N(CH$_3$)$_2$, $R^2$=H, each $R^4$=CH$_3$, Z=NH-pyruvoyl, and D=Nα-linked octreotide.

A 250 mM solution of t-butyl succinimidyl carbonate in DMF (440 L) was added to a mixture of octreotide acetate (128 mg) and N,N-diisopropylethylamine (0.2 mL) in 2 mL of amine-free DMF. After 1 h, HPLC analysis indicated the presence of 90% mono-Boc-octreotide, 2.5% di-Boc-octreotide, and 7% octreotide. A solution of 4-(2-diethoxypropionamido)-1-((N,N-dimethylamino)sulfonyl)-3,3-dimethyl-2-butyl succinimidyl carbonate (Example 3; 54 mg) in 100 μL of DMF was added. The mixture was kept at ambient temperature for 16 h, then diluted with EtOAc and washed with 5% KHSO$_4$ followed by brine. After drying over Na$_2$SO, the mixture was filtered and concentrated to yield the fully-protected intermediate as a foam. This was dissolved in 1 mL of CH$_3$CN and treated with 1 mL of 2 N HCl at 50° C. for 30 min. The solution was cooled to ambient temperature, diluted with 2 mL of water and added carefully to 5 mL of 1 M NaHCO$_3$. The precipitated product was collected by centrifugation, washed with water and dichloromethane, and dissolved in 5 mL of methanol.

Example 7

Preparation of Linker-Drug of Formula (II) Wherein Y=N(R$^6$)CH$_2$ romethyl)carbamate linker (Example 4, 1 mmol) in 1 mL of THF was added. The orange color gradually paled and the suspension cleared. The mixture was quenched with 10% aqueous citric acid, then extracted with ethyl acetate. The organic extract was washed with water and brine, then dried over MgSO$_4$, filtered, and evaporated. Purification by chromatography on SiO$_2$ using a gradient of 0-100% acetone in hexane provided the linker-drug of formula (II) wherein n=1, R$^1$=CN, R$^2$=H, each R$^4$=Me, D=SN-38, Y=N(R$^6$)CH$_2$ (R$^6$=4-(N,N-diethylcarboxamidophenyl)), and Z=azide.

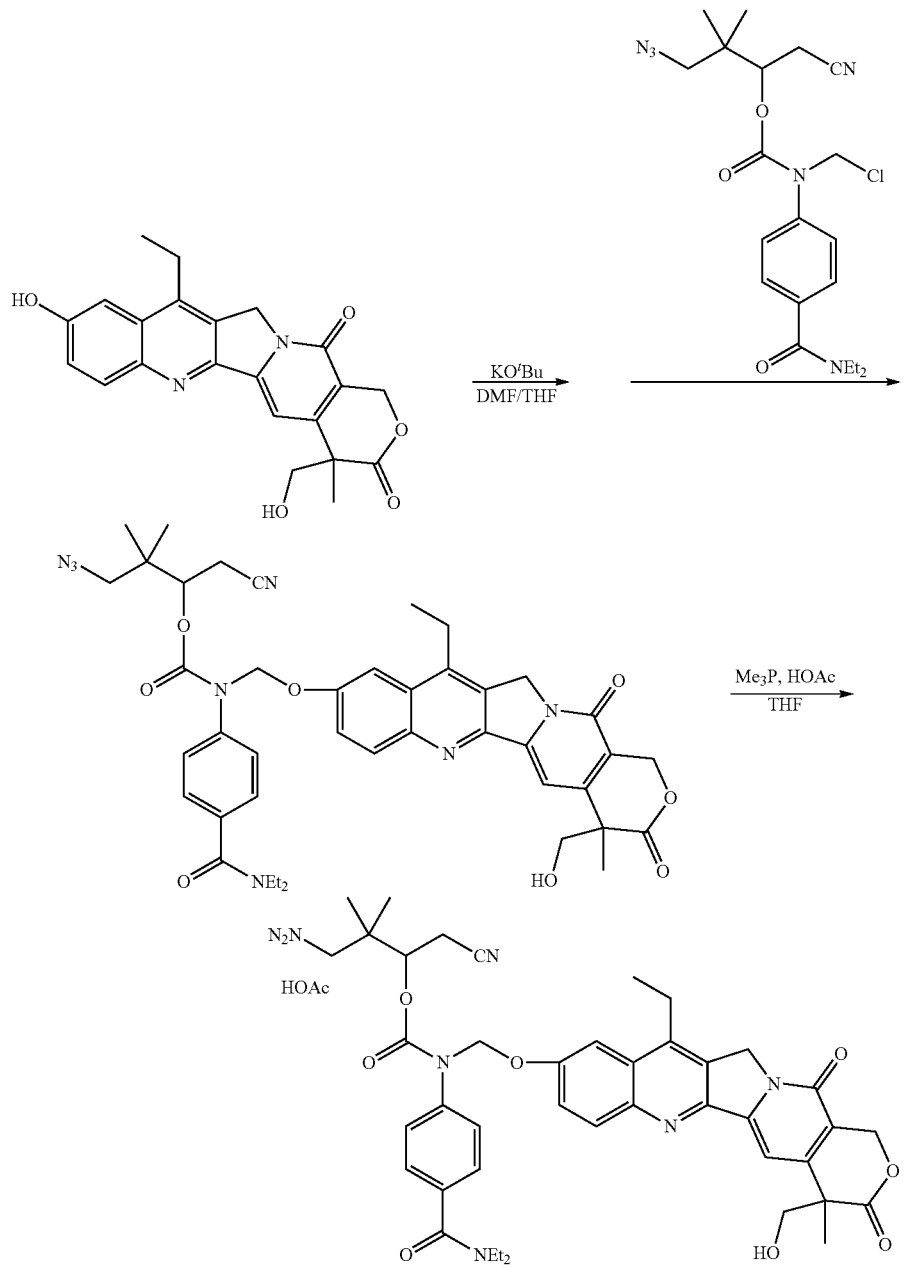

A solution of SN-38 (100 mg) in 10 mL of 1:1 DMF/THF was cooled on ice and treated dropwise with 1 M potassium tert-butoxide (0.26 mL, 1 Eq). The resulting orange suspension was stirred for 30 min, then a solution of the N-(chlo- The corresponding compound wherein Z=amine was prepared as follows. A solution of the compound wherein Z=azide in THF was added to a mixture of 1 M trimethylphosphine in THF and acetic acid. After gas evolution had ceased, water was added and the mixture was stirred for 1 h before concentrating to dryness. The residue was partitioned between water and ethyl acetate, and the aqueous phase was collected and dried. Final purification by preparative HPLC used a gradient of 0-100% acetonitrile/water/0.1% TFA.

Example 8

Formation of Conjugates of Formula (III) Wherein M is Soluble PEG and Z*=1,2,3-triazole A mixture of 20-kDa 4-armed PEG-tetra(cyclooctyne) (prepared according to Example 14 below, Prepolymer B) and the linker-drug wherein Z=azide of Example 5 in acetonitrile was kept at 50° C. for 16 h. Dialysis (12-kDa SpectraPor 2) against water followed by methanol provided the purified conjugate of formula (III) wherein M is soluble 4-armed PEG and Z* is 1,2,3-triazole.

Example 9

Formation of Conjugates of Formula (III) Wherein M is Soluble PEG and Z*=Oxime 20-kDa 4-armed PEG-tetra(aminooxyacetamide) was prepared by reacting 20-kDa 4-armed PEG-tetraamine (100 mg, NOF America) with excess (Boc-aminooxy)acetic acid in the presence of HATU and N,N-diisopropylethylamine in DMF. After 1 h, the PEG was precipitated by slow addition to stirred MTBE, collected by centrifugation, and dried under vacuum. This was dissolved in 2 mL of 1:1 $CH_2Cl_2$/$CF_3CO_2H$, kept 1 h, and evaporated to dryness. The residue was dissolved in 2 mL of THF and the product was precipitated by slow addition to stirred MTBE, collected by centrifugation, and dried under vacuum.

A mixture of 20-kDa 4-armed PEG-tetra(aminooxyacetamide) and the linker-drug wherein Z=ketone of Example 6 in 1:1 DMSO/0.1 M acetic acid was kept at 50° C. for 16 h. Dialysis (12-kDa SpectraPor 2) against water followed by methanol provided the purified conjugate of formula (III) wherein M is soluble 4-armed PEG and Z* is oxime.

Example 10

Formation of Conjugates of Formula (III) Wherein M is Soluble PEG and Z*=Carboxamide A mixture of 20-kDa 4-armed PEG-tetra(succinimidyl ester) (JenKem), N,N-diisopropylethylamine, and the linker-drug wherein Z=amine of Example 7 in THF was stirred for 1 h. Dialysis (12-kDa SpectraPor 2) against water followed by methanol provided the purified conjugate of formula (III) wherein M is soluble 4-armed PEG and Z* is carboxamide.

Example 11

Formation of Conjugates of Formula (III) Wherein M is Insoluble Degradable PEG Microspheres A suspension of PEG microspheres (100 mL) of formula (IV) wherein $P^1$ and $P^2$ are both 10-kDa 4-armed PEG, Z*=1,2,3-triazole, n=1, each $R^4$=$CH_3$, $R^1$=$SO_2N(CH_3)_2$, $R^2$=H, and W=$CH((CH_2)_4NH_2)C(=O)NH$ (i.e., x=0, y=4, z=0, B=$NH_2$, and C*=carboxamide) (prepared according to Example 14 below) was activated by reaction with 4-cyclooctynyl succinimidyl carbonate and N,N-diisopropylethylamine in acetonitrile. The resulting hydrogel comprising a multiplicity of reactive groups Z'=cyclooctynyl was then suspended in 50 mM acetate buffer, pH 5, and reacted with a solution of linker-drug of formula (II) wherein Z=azide, n=1, each $R^4$=$CH_3$, $R^1$=$SO_2N(CH_3)_2$, $R^2$=H, and D=-HGEGTFTSDL-SKQMEEEAVRLFIEWLKQGGPSSGAPPPS-$NH_2$ (exenatide-[N28Q](Example 5) (SEQ ID NO: 1). After 48 h at 50° C., the microspheres were washed extensively with acetate buffer to remove unconjugated peptide. Analysis indicated the packed microsphere slurry contained 2.1 μmol linked peptide/mL slurry.

Example 12

Release Kinetics

Conjugates were dissolved in 100 mM buffer at 0.25-2 mM and kept at 37° C. in a thermostated HPLC autosampler. Samples (5-10 μL) were removed periodically and injected onto the HPLC (Phenomenex Jupiter 5 μm 4.6×150 mm $C_{18}$ reversed-phase) and eluted with a linear gradient from 0 to 100% MeCN/$H_2O$/0.1% TFA at 1 mL/min. Peaks were detected at 280 nm (peptides) or 350 nm (dinitrophenyl-Lys) and integrated to provide peak areas for the conjugates and released peptides. Extents of drug release were calculated as (area of released drug)/[(area of released drug)±(area of conjugate)]. Octreotides linked at the α-amine as described in Example 5 above were conjugated to 20-kDa MeO-PEG-cyclooctyne as described in Example 8. Half-lives for release at pH 7.4 were calculated from the results obtained at a given pH using the equation $$t_{1/2}(pH\ 7.4) = \ln(2) \cdot 10^{(X-7.4)}/k_{obs}$$

TABLE 1

Kinetics of α-linked octreotide release from soluble PEG conjugates in borate buffer at various pH values and temperatures.

| $R^1$ | pH | Temp (° C.) | $k_{obs}$ ($h^{-1}$) | Calc $t_{1/2}$ (h) for pH 7.4, 37° C. |
|---|---|---|---|---|
| CN | 9.29 | 37 | 0.1283 | 419 |
| CN | 9.29 | 38 | 0.1616 | 380 [a] |
| $SO_2Me$ | 9.29 | 38 | 0.4798 | 128 [a] |
| $SO_2iPr$ | 9.29 | 38 | 0.3985 | 154 [a] |
| $SO_2NMe_2$ | 9.29 | 37 | 0.08548 | 629 |
| $SO_2NMe_2$ | 9.40 | 37 | 0.09602 | 722 |
| $SO_2N(Et)Me$ | 9.29 | 37 | 0.043 | 1251 |
| $SO_2$(morpholino) | 9.29 | 38 | 0.3148 | 195 [a] |
| $SO_2$(4-methylpiperidinyl) | 9.29 | 37 | 0.04896 | 1099 |
| $SO_2$(4-methylpiperidinyl) | 9.29 | 38 | 0.06448 | 954 [a] |
| $SO_2$(4-methylpiperidinyl) | 9.40 | 37 | 0.05947 | 1166 |

[a] $t_{1/2,\ 37°\ C.} = (t_{1/2,\ 38°\ C.})*1.143$ (See Arrhenius equation in Santi PNAS 2012, SI).
In all cases, n = 1, $R^2$ = H, each $R^4$ = Me, Z = $N_3$, Y is absent, and D = Nα-linked octreotide.

Example 13

Kinetics of Aza-Michael Reactions

Kinetics of forward reaction: In each of three 1.5 mL glass HPLC vial, a 5 mM solution of either standard, β-methyl, or gem dimethyl vinyl sulfone (0.1 mL, 0.5 μmol, 0.5 mM final concentration) in DMSO was added to 0.9 mL of pre-warmed glycine cleavage buffer A, B, or C. The vials were kept in a heated (37° C.) HPLC autosampler, and the aza-Michael reactions were periodically monitored by C18 HPLC.

Cleavage buffer A: 1.1 M glycine (1.0 M final concentration), 0.11 M HEPES, pH 7.4 @37° C.
Cleavage buffer B: 1.1 M glycine (1.0 M final concentration), 0.11 M Bicine, pH 8.4 @37° C.
Cleavage buffer C: 0.11 M glycine (0.10 M final concentration), pH 9.5 @37° C. $K_{eq}$ was calculated using the following equations:

$$K_{eq} = K_{eq\ app}/[\text{Gly}]$$

$$K_{eq\ app} = [\text{GA}]_{eq}/[\text{VS}]_{eq} = \text{plateau}/(0.5\ \text{mM}-\text{plateau})$$

[Gly]=glycine concentration in M
[GA]=glycine adduct concentration in mM
[VS]=vinyl sulfone concentration in mM
Plateau (mM) determined in Prism.

The two unknowns, kf (association) and kr (dissociation), are calculated from the two equations below with $k_{obs}$ determined by Prism fit and $K_{eq\ app}$ defined above:

$$k_{obs} = k_f[\text{Gly}] + k_r$$

$$k_f[\text{Gly}]/k_r = K_{eq\ app}.$$

Figure 1:
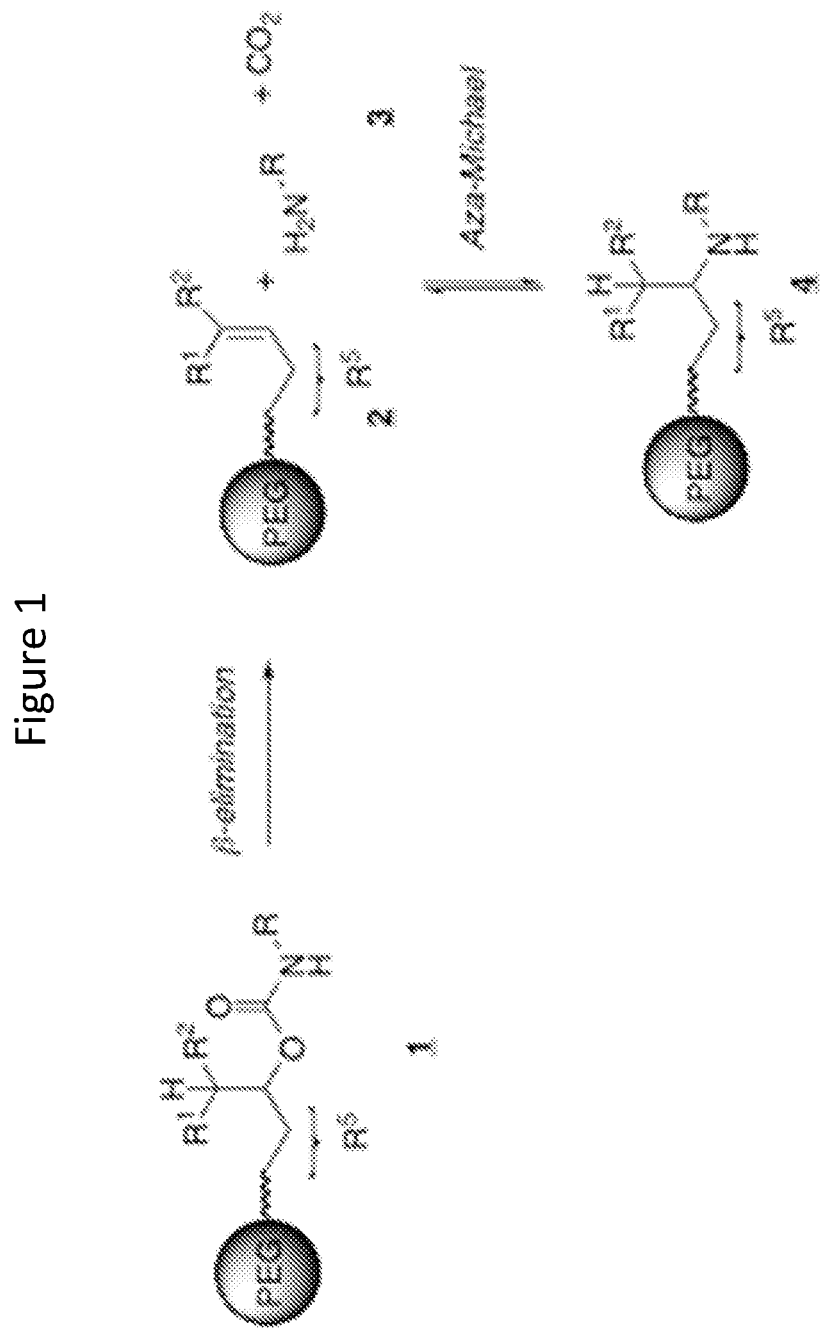
FIG. 1 illustrates the cleavage of a carbamate linker disclosed in U.S. Pat. No. 9,649,385 in a conjugate. The intact conjugate 1 undergoes a pH-dependent beta-elimination reaction leading to cleavage of the linker and formation of linker remnant 2 together with free amine 3. These products may undergo a subsequent reversible aza-Michael reaction to form a relatively stable readdition adduct 4. When R is an amine-containing drug or prodrug, the linker is a drug-releasing linker. When R is a second PEG prepolymer, the linker is part of a crosslinker in a PEG hydrogel.
Figure 2:
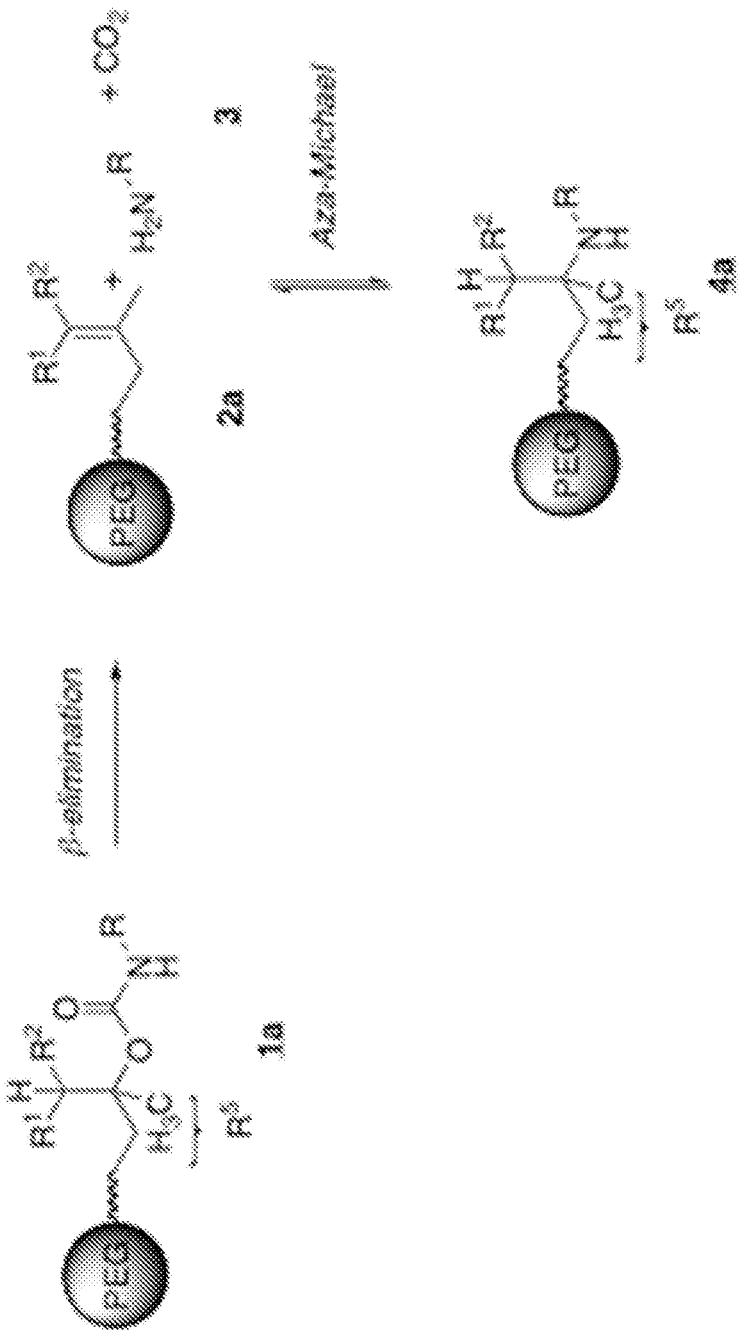
FIG. 2 illustrates the cleavage of a carbamate linker disclosed in U.S. Pat. No. 9,649,385 in a conjugate, wherein both $R^5$ groups are alkyl. Steric hindrance by the alkyl groups at $R^5$ is expected to slow the readdition process.

Kinetics of reverse reaction: The rate of the dissociative retro-aza-Michael reaction (FIG. 2.3A) was measured directly from isolated glycine adducts. Each purified glycine adduct was diluted into pH 7.4 HEPES buffer at 37° C. in the absence of added glycine. The concentration of the starting glycine adduct was plotted against time, and each curve was fitted to a first-order decay in Prism (FIG. 2.3B). For each reaction, the calculated infinity value was <1 µM, indicating that the reactions proceed to completion, thus kr is essentially equivalent to $k_{obs}$. To each of three 0.3 mL plastic conical HPLC vials, a 0.7-3.8 mM solution of either standard, β-methyl, or gem dimethyl sulfo-DIBO glycine adduct (11 nmol, 50 µM final concentration) in DMSO was added to 0.2 mL of prewarmed 0.1 M HEPES, pH 7.0 containing enough water to adjust the final volume to 0.22 mL. The reaction vials were kept in a heated (37° C.) HPLC autosampler, and the retro aza-Michael reactions were periodically monitored by C18 HPLC. Concentration of the starting glycine adduct [GA] in µM was calculated using the equation below and plotted against time using Prism:

[GA]=ga/(ga+vs)*50 µM

[GA]=glycine adduct concentration in µM
ga=glycine adduct integrated HPLC peak area (254 nm)
vs=vinyl sulfone integrated HPLC peak area (254 nm)
50 M=[GA] i and maximum possible [VS]
$k_r$ (dissociation) determined by fitting the data to a first-order decay in Prism.

Example 14

Preparation of Degradable PEG-Hydrogels

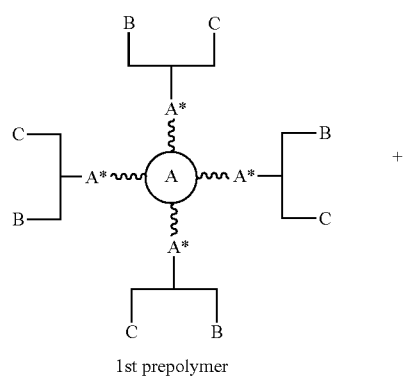

1st prepolymer

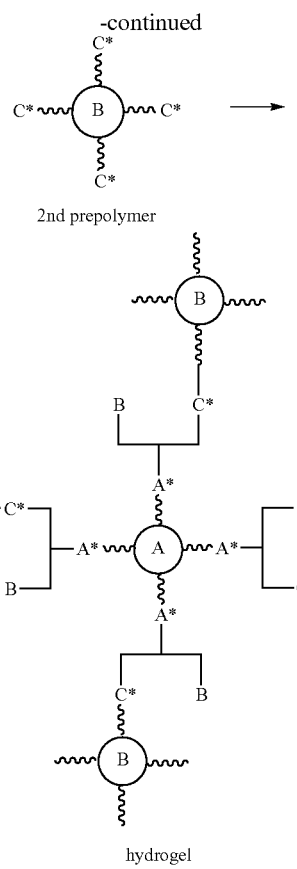

hydrogel

Hydrogels of the invention are prepared by polymerization of two prepolymers comprising groups C and C' that react to form a connecting functional group, C*. The prepolymer connection to one of C or C' further comprises a cleavable linker introduced by reaction with a molecule of Formula (I), so as to introduce the cleavable linker into each crosslink of the hydrogel.

In one embodiment, a first prepolymer comprises a 4-armed PEG wherein each arm is terminated with an adapter unit having two mutually-unreactive ("orthogonal") functional groups B and C. B and C may be initially present in protected form to allow selective chemistry in subsequent steps. In certain embodiments, the adapter unit is a derivative of an amino acid, particularly lysine, cysteine, aspartate, or glutamate, including derivatives wherein the alpha-amine group has been converted to an azide, for example monoesters of 2-azidoglutaric acid. The adapter unit is connected to each first prepolymer arm through a connecting functional group A*, formed by condensation of a functional group A on each prepolymer arm with cognate functional group A' on the adapter unit. A second prepolymer comprises a 4-armed PEG wherein each arm is terminated with a functional group C' having complimentary reactivity with group C of the first prepolymer, such that crosslinking between the two prepolymers occurs when C and C' react to form C*.

As an illustrative example, a first prepolymer was prepared as follows. H-Lys(Boc)-OH was acylated with a linker of Formula (I) wherein Z=azide to give an adapter unit where A=COOH, B=Boc-protected $NH_2$, and C=azide. This was coupled to 20-kDa 4-armed PEG-tetraamine, and the Boc group was removed to provide a first prepolymer wherein A*=amide, B=$NH_2$, and C=azide and wherein a cleavable linker of formula (I) is incorporated into the linkage between each arm and group C of the first prepolymer. The corresponding second prepolymer was prepared by acylation of 20-kDa 4-armed PEG-tetraamine with 5-cyclooctynyl succinimidyl carbonate to give a second prepolymer wherein C'=cyclooctyne. Upon mixing of the first and second prepolymers, reaction of the C=azide and C'=cyclooctyne groups form corresponding triazole groups and thereby crosslink the two prepolymers into a 3-dimensional network, with each crosslink comprising a cleavage linker resulting from incorporation of the compound of Formula (I), and wherein each node resulting from incorporation of a first prepolymer comprises a remaining functional group B=NH$_2$ which can be derivatized for attachment of further linkers, drugs, fluorophores, metal chelators, and the like.

Prepolymer A Wherein A*=Amide, B=Amine, and C=Azide

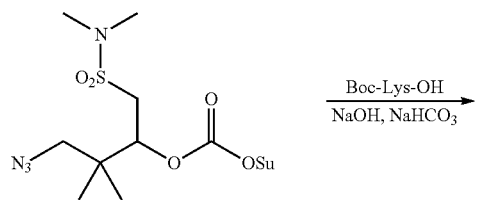

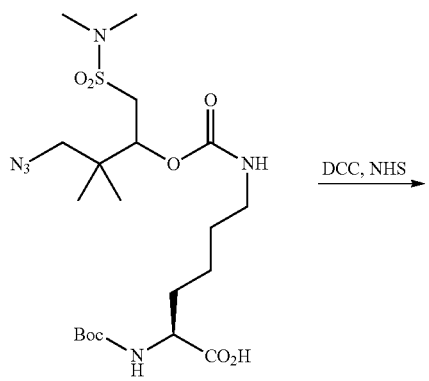

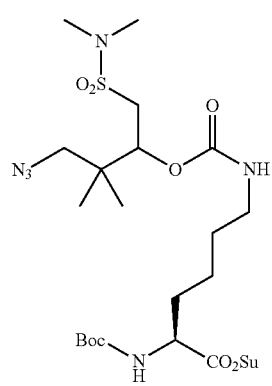

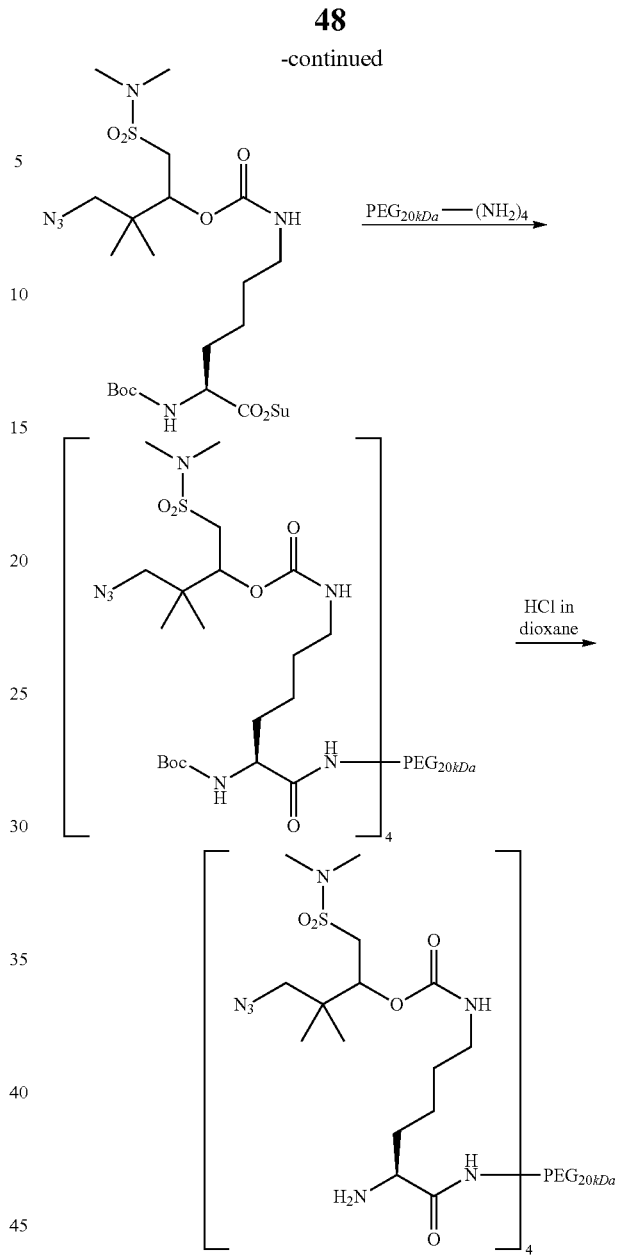

(1) N$^\alpha$-Boc-N$^\varepsilon$-{4-Azido-3,3-dimethyl-1-[(N,N-dimethyl)aminosulfonyl]-2-butyloxycarbonyl}-Lys-OH A solution of Boc-Lys-OH (2.96 g, 12.0 mmol) in 28 mL of H$_2$O was successively treated with 1 M aq NaOH (12.0 mL, 12.0 mmol), 1 M aq NaHCO$_3$ (10.0 mL, 10.0 mmol), and a solution of O-{4-azido-3,3-dimethyl-1-[(N,N-dimethyl)aminosulfonyl]-2-butyl}-O'-succinimidyl carbonate (3.91 g, 10.0 mmol, 0.1 M final concentration) in 50 mL of MeCN. After stirring for 2 h at ambient temperature, the reaction was judged to be complete by C18 HPLC (ELSD). The reaction was quenched with 30 mL of 1 M KHSO$_4$ (aq). The mixture was partitioned between 500 mL of 1:1 EtOAc:H$_2$O. The aqueous phase was extracted with 100 mL of EtOAc. The combined organic phase was washed with H$_2$O and brine (100 mL each) then dried over MgSO$_4$, filtered, and concentrated by rotary evaporation to provide the crude title compound (5.22 g, 9.99 mmol, 99.9% crude yield) as a white foam.

C18 HPLC, purity was determined by ELSD: 99.1% (RV=9.29 mL).

LC-MS (m/z): calc, 521.2; obsd, 521.3 [M−H]⁻.

(2) $N^\alpha$-Boc-$N^\epsilon$-{4-Azido-3,3-dimethyl-1-[(N,N-dimethyl)aminosulfonyl]-2-butyloxycarbonyl}-Lys-OSu Dicyclohexylcarbodiimide (60% in xylenes, 2.6 M, 4.90 mL, 12.7 mmol) was added to a solution of $N^\alpha$-Boc-$N^\epsilon$-{4-azido-3,3-dimethyl-1-[(N,N-dimethyl)aminosulfonyl]-2-butyloxycarbonyl}-Lys-OH (5.11 g, 9.79 mmol, 0.1 M final concentration) and N-hydroxysuccinimide (1.46 g, 12.7 mmol) in 98 mL of $CH_2Cl_2$. The reaction suspension was stirred at ambient temperature and monitored by C18 HPLC (ELSD). After 2.5 h, the reaction mixture was filtered, and the filtrate was loaded onto a SiliaSep 120 g column. Product was eluted with a step-wise gradient of acetone in hexane (0%, 20%, 30%, 40%, 50%, 60%, 240 mL each). Clean product-containing fractions were combined and concentrated to provide the title compound (4.95 g, 7.99 mmol, 81.6% yield) as a white foam.

C18 HPLC, purity was determined by ELSD: 99.7% (RV=10.23 mL).

LC-MS (m/z): calc, 520.2; obsd, 520.2 [M+H-Boc]⁺.

(3) ($N^\alpha$-Boc-$N^\epsilon$-{4-Azido-3,3-dimethyl-J-[(N,N-dimethyl)aminosulfonyl]-2-butyloxycarbonyl}-Lys)$_4$-$PEG_{20kDa}$ $PEG_{20kDa}$-$(NH_2)_4$ (20.08 g, 0.9996 mmol, 3.998 mmol $NH_2$, 0.02 M $NH_2$ final concentration) was dissolved in 145 mL of MeCN. A solution of $N^\alpha$-Boc-$N^\epsilon$-{4-azido-3,3-dimethyl-1-[(N,N-dimethyl)aminosulfonyl]-2-butyloxycarbonyl}-Lys-OSu (2.976 g, 4.798 mmol) in 50 mL of MeCN was added. The reaction was stirred at ambient temperature and analyzed by C18 HPLC (ELSD). The starting material was converted to a single product peak via three slower eluting intermediate peaks. After 1 h, $Ac_2O$ (0.37 mL, 4.0 mmol) was added. The reaction mixture was stirred 30 min more then concentrated to ~50 mL by rotary evaporation. The reaction concentrate was added to 400 mL of stirred MTBE. The mixture was stirred at ambient temperature for 30 min then decanted. MTBE (400 mL) was added to the wet solid, and the suspension was stirred for 5 min and decanted. The solid was transferred to a vacuum filter, and washed/triturated with 3×100 mL of MTBE. After drying on the filter for 10 min, the solid was transferred to a tared 250 mL HDPE packaging bottle. Residual volatiles were removed under high vacuum until the weight stabilized to provide the title compound (21.23 g, 0.9602 mmol, 96.1% yield) as a white solid.

C18 HPLC, purity was determined by ELSD: 89.1% (RV=10.38 mL) with a 10.6% impurity (RV=10.08).

(4) ($N^\epsilon$-{4-Azido-3,3-dimethyl-1-[(N,N-dimethyl)aminosulfonyl]-2-butyloxycarbonyl}-Lys)$_4$-$PEG_{20kDa}$ ($N^\epsilon${4-Azido-3,3-dimethyl-1-[(N,N-dimethyl)aminosulfonyl]-2-butyloxycarbonyl}-Lys)$_4$-$PEG_{20kDa}$ (19.00 g, 0.8594 mmol, 3.438 mmol Boc, 0.02 M Boc final concentration) was dissolved in 86 mL of 1,4-dioxane. After stirring for 5 min to fully dissolve the PEG, 4 M HCl in dioxane (86 mL, 344 mmol HCl) was added. The reaction was stirred at ambient temperature and analyzed by C18 HPLC (ELSD). The starting material was converted to a single product peak via three faster eluting intermediate peaks. After 2 h, the reaction mixture was concentrated to ~40 mL. THF (10 mL) was added to the concentrate, and the solution was again concentrated to ~40 mL. The viscous oil was poured into 400 mL of stirred $Et_2O$. After stirring at ambient temperature for 20 min, the supernatant was decanted from the precipitate. The wet solid was transferred to a vacuum filter with the aid of 200 mL $Et_2O$ and washed with $Et_2O$ (3×75 mL). The solid was dried on the filter for 10 min then transferred to a tared 250 mL HDPE packaging bottle. Residual volatiles were removed under high vacuum overnight to provide the title compound (17.52 g, 0.8019 mmol, 93.3% yield @4 HCl) as a white solid.

C18 HPLC, purity was determined by ELSD: 99.2% (RV=9.34 mL).

Prepolymer B Wherein C'=Cyclooctynyl

A 4-mL, screw top vial was charged with $PEG_{20kDa}$-$[NH_2]_4$ (SunBright PTE-200PA; 150 mg, 7.6 µmol PEG, 30.2 µmol $NH_2$, 1.0 equiv, 20 mM final amine concentration), MeCN (1.5 mL), and $iPr_2NEt$ (7 µL, 40 µmol, 1.3 equiv, 27 mM final concentration). A solution of the activated ester clyclooctyne (39 µmol, 1.3 equiv, 27 mM final concentration) was added and the reaction mixture was stirred at ambient temperature. Reactions were monitored by C18 HPLC (20-80% B over 11 min) by ELSD. When complete, $Ac_2O$ (3 µL, 30 µmol, 1 equiv per starting $NH_2$) was added to the reaction mixture and the mixture was stirred for 30 min. The reaction mixture was then concentrated to a thick oil and suspended in MTBE (20 mL). The resulting suspension as vigorously stirred for 10 min. The resulting solids were triturated three times with MTBE (20 mL) by vigorously mixing, pelleting in a centrifuge (2800 rpm, 4° C., 10 min), and removal of the supernatant by pipette. The resulting solids were dried under vacuum at ambient temperature for no more than 30 min. Stock solutions were prepared in 20 mM NaOAc (pH 5) with a target amine concentration of 20 mM. Cyclooctyne concentration was then verified by treatment with $PEG_7$-$N_3$ (2 equiv) and back-titration of the unreacted $PEG_7$-$N_3$ with DBCO-$CO_2H$.

Macromonomers prepared using this procedure include those wherein the cyclooctyne group is MFCO, 5-hydroxycyclooctyne, 3-hydroxycyclooctyne, BCN, DIBO, 3-(carboxymethoxy)cyclooctyne, and 3-(2-hydroxyethoxy)cyclooctyne, prepared using MFCO pentafluorophenyl ester, 5-((4-nitrophenoxy-carbonyl)oxy)cyclooctyne, 3-(4-nitrophenoxycarbonyl)oxycyclooctyne, BCN hydroxysuccinimidyl carbonate, DIBO 4-nitrophenyl carbonate, 3-(carboxymethoxy)cyclooctyne succinimidyl ester, and 3-(hydroxyethoxy)cyclooctyne 4-nitrophenyl carbonate, respectively.

Hydrogel Microsphere preparation. Hydrogel microspheres were prepared and activated as described in Schneider et al. (2016) Bioconjugate Chemistry 27: 1210-15.

Example 15

Compound of Formula (II) Wherein Z=$N_3$, n=1, $R^1$=(4-methylphenyl)$SO_2$, $R^2$=H, Each $R^4$=Me, Y=Absent, and D=Insulin Lispro Attached Via $Lys^{B28}$ As an alternative to preparation of compounds of Formula (II) by solid-phase peptide synthesis (see Example 5), compounds of Formula (II) wherein D is a peptide may be formed by reaction of the preformed peptide with an activated linker of Formula (I) under conditions where at least one amine group on the peptide is free for reaction. When the peptide comprises both an N-terminal alpha-amine and one or more lysine epsilon-amines, preferential attachment of the linker to a lysine epsilon-amine can be obtained by performing the reaction at high pH or in organic solvent in the presence of excess tertiary amine.

One 10-mL vial of Humalog (100 U/mL) was adjusted to pH 5.4 using 0.1 N HCl, and the resulting precipitate was collected by centrifugation and the pellet was washed 2×15 mL of ethanol, 1×15 mL of methyl t-butyl ether (MTBE), and dried under vacuum. The dried insulin lispro (35 mg, 6 µmol) was dissolved in 3 mL of dimethyl formamide (DMF) and 30 µL (170 µmol) of N,N-diisopropylethylamine (DIPEA). A solution of 100 mM 4-azido-3,3-dimethyl-1-(4-methylphenylsulfonyl)-2-butyl succinimidyl carbonate in DMF (84 µL, 8.4 µmol) was added and the mixture was stirred at ambient temperature for 1 h. The mixture was evaporated to dryness under vacuum, and the residue was dissolved in 10 mL of 3:1 water/acetonitrile/0.1% trifluoroacetic acid. Purification by preparative HPLC using a 21.2× 150 mm Jupiter 5 um 300A $C_{18}$ reversed-phase column using a gradient from 30-50% acetonitrile/water/0.1% TFA over 20 min at 15 mL/min provided pure azido-linker-lispro where the linker is attached via the □-amine of B-chain Lys$^{28}$ (Compound of formula (II) wherein Z=N$_3$, n=1, $R^1$=(4-methylphenyl)SO$_2$, $R^2$=H, each $R^3$=Me, Y=absent, and D=insulin lispro attached via Lys$^{B28}$).

Similar linker-peptides of Formula (II) were prepared using the peptide teduglutide, [Gly$^2$]GLP-2.

Example 16

PEG Conjugate Releasing Insulin Lispro

Compound of Formula (III) Wherein M=20-kDa MeO-PEG, Z*=triazole, n=1, $R^1$=(4-methylphenyl)SO$_2$, $R^2$=H, each $R^4$=Me, Y=absent, D=insulin lispro attached via Lys$^{B28}$, and q=1

A solution of 20-kDa methoxy-PEG-amine (BroadPharm, 100 mg, 5 µmol), DIPEA (3 µL, 17 µmol), and (1R,8S,9s)-bicyclo[6.1.0]non-4-yn-9-ylmethyl succinimidyl carbonate (BCN-OSu, Sigma, 2 mg, 7 µmol) in 1 mL of acetonitrile was stirred at ambient temperature for 1 h, then evaporated to dryness. The residue was dissolved in 1 mL of THF and the solution added to 10 mL of MTBE with stirring. The precipitated PEG-cyclooctyne was collected, washed with MTBE, and dried under vacuum.

A mixture of the azido-linker-insulin lispro from Example 15 (1.1 µmol) and PEG-cyclooctyne (20 mg, 1 µmol) in 1 mL of 1:1 isopropanol:citrate buffer, pH 4, was kept at ambient temperature for 4 h, then dialyzed against water followed by methanol using a 12-14 kDa cutoff membrane. The dialzed product was evaporated to dryness to provide the compound of Formula (III) wherein M=20-kDa MeO-PEG, Z*=triazole, n=1, $R^1$=(4-methylphenyl)SO$_2$, $R^2$=H, Y=absent, D=insulin lispro attached via Lys$^{B28}$, and q=1.

When dissolved in 0.1 M borate buffer, pH 9.4, 37° C., this conjugate released free insulin lispro with $t_{1/2}$=2.08 h. This extrapolates to $t_{1/2}$=208 h at pH 7.4, 37° C.

The cognate conjugate wherein $R^1$=phenyl-SO$_2$ was prepared similarly, and released free insulin lispro with $t_{1/2}$=0.8 h when dissolved in 0.1 M borate buffer, pH 9.4, 37° C. This extrapolates to $t_{1/2}$=80 h at pH 7.4, 37° C.

Example 17

Hydrogel Comprising Releasable Insulin Lispro

The azide-linker-insulin lispro of Example 15 was attached to the degradable PEG-hydrogel of Example 14 to provide a slow-release depot of insulin lispro. For the PEG-hydrogel, Prepolymer A was (Nα-Boc-Nε-{4-Azido-3,3-dimethyl-1-[(N,N-dimethyl)aminosulfonyl]-2-butyloxycarbonyl}-Lys)4-PEG10 kDa, and Prepolymer B was ((4-cyclooctynyloxy-carbonyl)amino)$_4$-PEG$_{10kDa}$, which provided a PEG-hydrogel of formula (IV) wherein $P^1$ and $P^2$ were both 10-kDa 4-armed poly(ethylene glycol)s, Z*=triazole, n=1, $R^1$=(N,N-dimethylamino)SO$_2$, $R^2$=H, each $R^4$=CH$_3$, and W=(CH$_2$)$_x$—CH[(CH$_2$)$_y$B]—(CH$_2$)$_z$C wherein x=4, y=0, z=0, B=NH$_2$, and C*=carboxamide. This PEG-hydrogel was formed as microspheres as described previously in PCT Publication WO2019/152672, which is incorporated herein by reference.

A packed suspension of these hydrogel microspheres (B=NH$_2$) in acetonitrile (3.5 g containing 10.8 µmol of NH$_2$ by TNBS assay) was activated for linker-drug attachment by reaction with BCN-OSu (16.2 µmol) and triethylamine (43.1 µmol) for 4.5 h. Acetic anhydride (10.8 µmol) was added to cap any unreacted amine groups, and after 2 h the slurry was washed 5 times with 11 mL acetonitrile followed by 5 times with 11 mL of drug-loading solvent (100 mM citrate in 1:1 iPrOH:H$_2$O at pH 3.0). Final packed slurry was ~5.6 mL containing 7.3 µmol of cyclooctyne (B=[(1R,8S,9s)-bicyclo[6.1.0]non-4-yn-9-ylmethoxycarbonyl]amino).

A mixture of the activated hydrogel microspheres and the azide-linker-insulin lispro in drug-loading solvent was mixed gently for 24 h, then the suspension was washed repeatedly with reaction buffer to remove any unreacted azido-linker-insulin lispro and reaction byproducts. The final microsphere preparation comprised 1.5 µmol/mL insulin lispro, which was released with $t_{1/2}$=350 h at pH 7.4, 37° C.

Example 18

Hydrogel Comprising Releasable Exenatide

The degradable hydrogel of Example 14 wherein $P^1$ and $P^2$ were both 10-kDa 4-armed poly(ethylene glycol)s, Z*=triazole, n=1, $R^1$=(N,N-dimethylamino)SO$_2$, $R^2$=H, each $R^4$=CH$_3$, and W=(CH$_2$)$_x$—CH[(CH$_2$)$_y$B]—(CH$_2$)$_z$C wherein x=4, y=0, z=0, B=NH$_2$, and C*=carboxamide was activated by reaction with cyclooctynyl succinimidyl carbonate (5HCO-OSu), then the azido-linker-exenatide [N28Q] of Example 5 was attached. A packed amino microsphere slurry (1.2 mL) in MeCN containing 10.3 µmol amine was combined with neat triethylamine (41.1 µmol) and 5HCO-NHS (15.4 µmol). The reaction was mixed end-over-end for 18 hr and a qualitative TNBS test confirmed loading of the amines (described in the general methods). Acetic anhydride was added (1 eq, 10.3 µmol) to cap any remaining free amines and after a 2 hr reaction the slurry was washed 5 times with 6 mL acetonitrile. Final packed slurry was 1.4 mL containing 10.3 µmol 5HCO. Two tared 10 mL syringes were filled with ~1 g 5HCO-microsphere slurry in MeCN, containing ~9 µmol 5HCO. The slurries were washed 4× with 6.5 mL of the reaction solvent (100 mM citrate in 1:1 DMSO:$H_2O$ at pH 3.0). The $N_3$-peptide was added to the packed slurry at 1.2 equivalents to the 5HCO (11 µmol $N_3$) and incubated at 37 C for 18 hours with agitation.

The loaded microspheres were washed 5 times with 6.5 mL of the reaction solvent ($OD_{280}$ of the final wash was below detection) followed by 3 washes with isotonic acetate buffer (10 mM Na acetate, 143 mM NaCl, 0.05% polysorbate 20 (w/v) pH 5.0 and 2× with isotonic acetate buffer containing 0.8% Na carboxymethyl cellulose. The payload concentration and fraction loaded was determined by solubilizing ~50 µL of the packed slurry (~50 mg) in 9 volumes (~450 µL) of 50 mM NaOH for one hour at ambient temperature. The payload content was determined by absorbance at 280 nm for [$Gln_{28}$]exenatide (E=5500 $M^{-1}$ $cm^{-1}$). A PEG assay was run on the same NaOH solubilized samples to measure the PEG concentration for each construct and determine the fraction loading by comparison to the peptide concentration.

Samples of the loaded microspheres (~50 mg) were placed in 1.5 mL screw top microcentrifuge tubes and the release kinetics/delegation reaction was started by addition of 19 volumes (0.95 mL) of 100 mM Na Borate buffer pH 9.4 at 37 C. In order to capture as many timepoints as possible, two reactions for each conjugate were started 18 hours apart. The reactions at 37° C. were incubated in a water bath with shaking. At t=0 and various timepoints, the microsphere slurries were pelleted at 20,000×g, the visual presence or absence of a microsphere pellet was noted, 20 µL of the reaction supernatant was removed and quenched by addition to 4 µL of 4M acetic acid and the samples were stored at −20 C. The concentration of exenatide[N28Q] in the reaction supernatant was determined by absorbance at 280 nm on a Nanodrop UV-Vis. The state of the microspheres was also noted visually at each timepoint (solid/present or solubilized/gone). The $A_{280}$ of the supernatant timepoints were plotted and fit to a single exponential to determine the release rate for each peptide. A PEG assay was run on the supernatant samples to measure the soluble PEG concentration at each timepoint to generate a solubilization/reverse gelation curve. Assay of the microspheres showed a peptide content of 5.19 µmol/mL, corresponding to 95% loading of available B sites. At pH 9.4, 37° C., these hydrogel microspheres released exenatide[N28Q] with $t_{1/2}$=17.5 h, and dissolved with a delegation time of 32 h.

A similar exenatide-releasing hydrogel is prepared by replacing the cyclooctynyl succinimidyl carbonate using in the activation step with BCN-OSu, as illustrated in Example 17.

Figure 7:
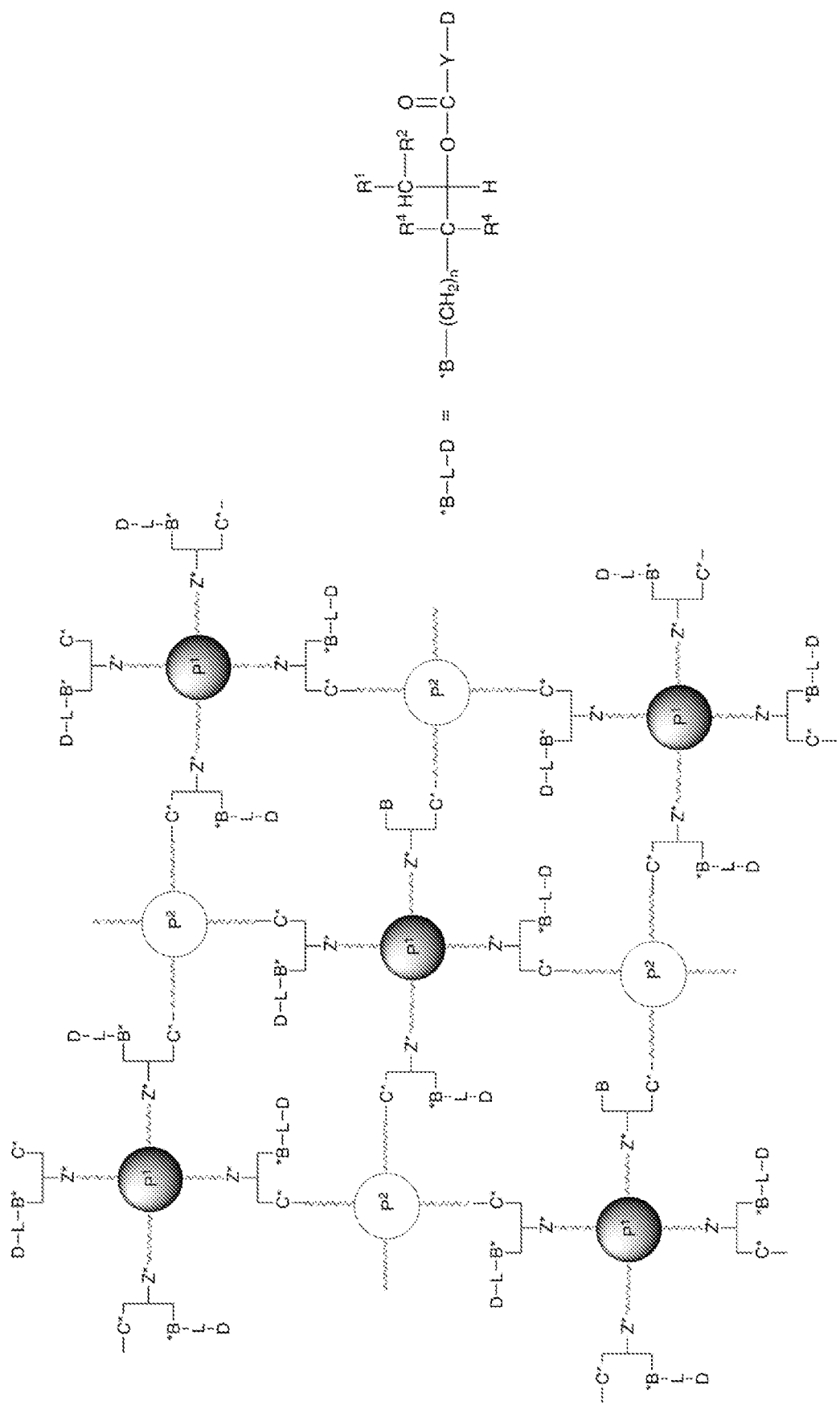
FIG. 7 shows an illustrative structure of a drug-releasing hydrogel comprising crosslinks of formula (IV). A linker-drug (L-D) of formula (II) is attached to the hydrogel via reactive group B.
Figure 8:
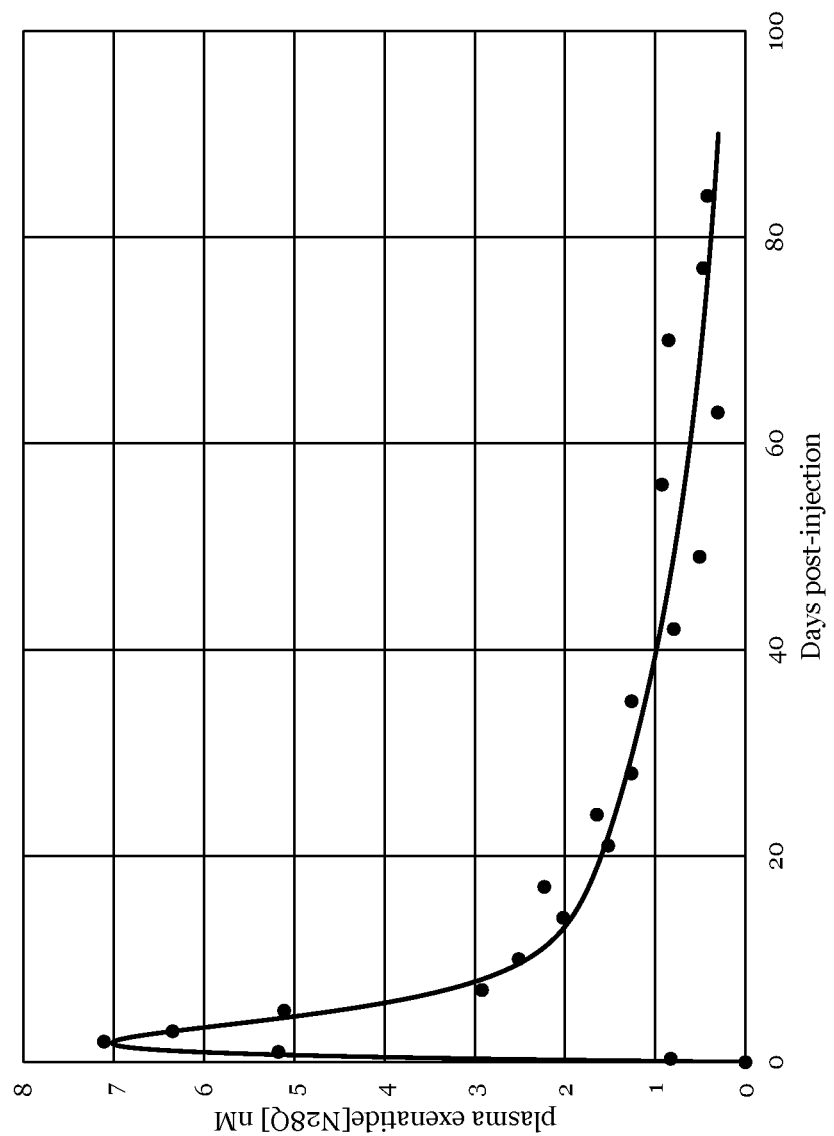
FIG. 8 shows the plasma concentration of exenatide [N28Q] released from the exenatide-releasing hydrogel microsphere conjugate of Example 18. Rats (n=3) were injected s.c. with a suspension of the conjugate comprising 9.2 μmol/kg of exenatide[N28Q] at day 0. Plasma samples were obtained and analyzed by LC/MS. The conjugate provided continuous exposure to exenatide[N28Q] for at least 84 days post-injection, showing a release $t_{1/2}$ of 750 hours (31 days).
Figure 9:
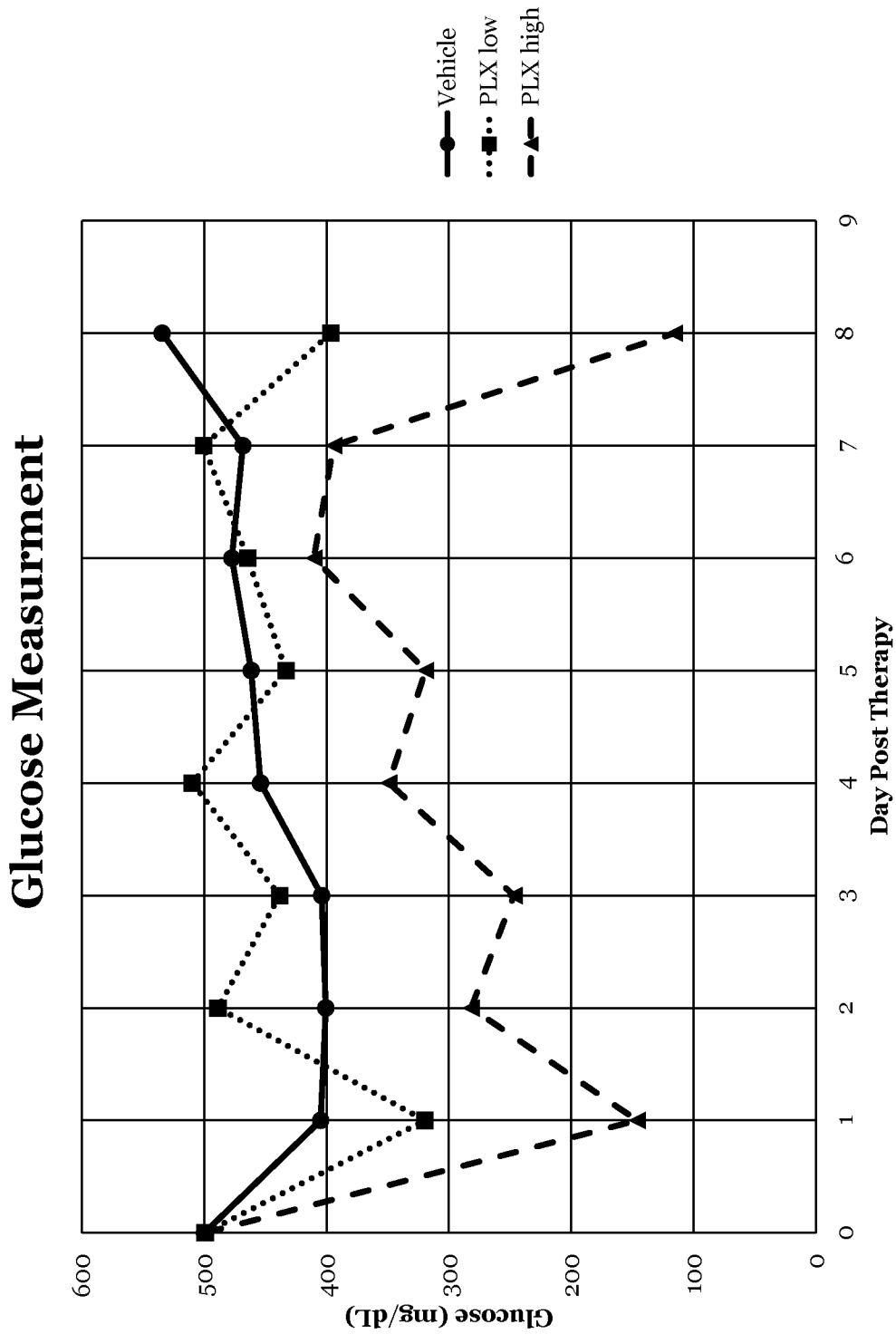
FIG. 9 shows blood glucose measured in STZ-induced diabetic mice treated with the insulin lispro-releasing hydrogel microsphere conjugate of Example 17. Mice were treated with streptozotocin to induce diabetes, then injected s.c. with a suspension of the conjugate comprising either 1.2 μmol/kg (low dose, squares) or 4.8 μmol/kg (high dose, triangles) of insulin lispro on days 0 and 7. Vehicle control (circles) consisted of non-peptide bearing microspheres. Blood samples were drawn and analyzed for blood glucose. The low dose suppressed blood glucose for 1 day, while the high dose suppressed blood glucose for 5 days post-injection. The effects were repeated upon the second dose.
Figure 10:
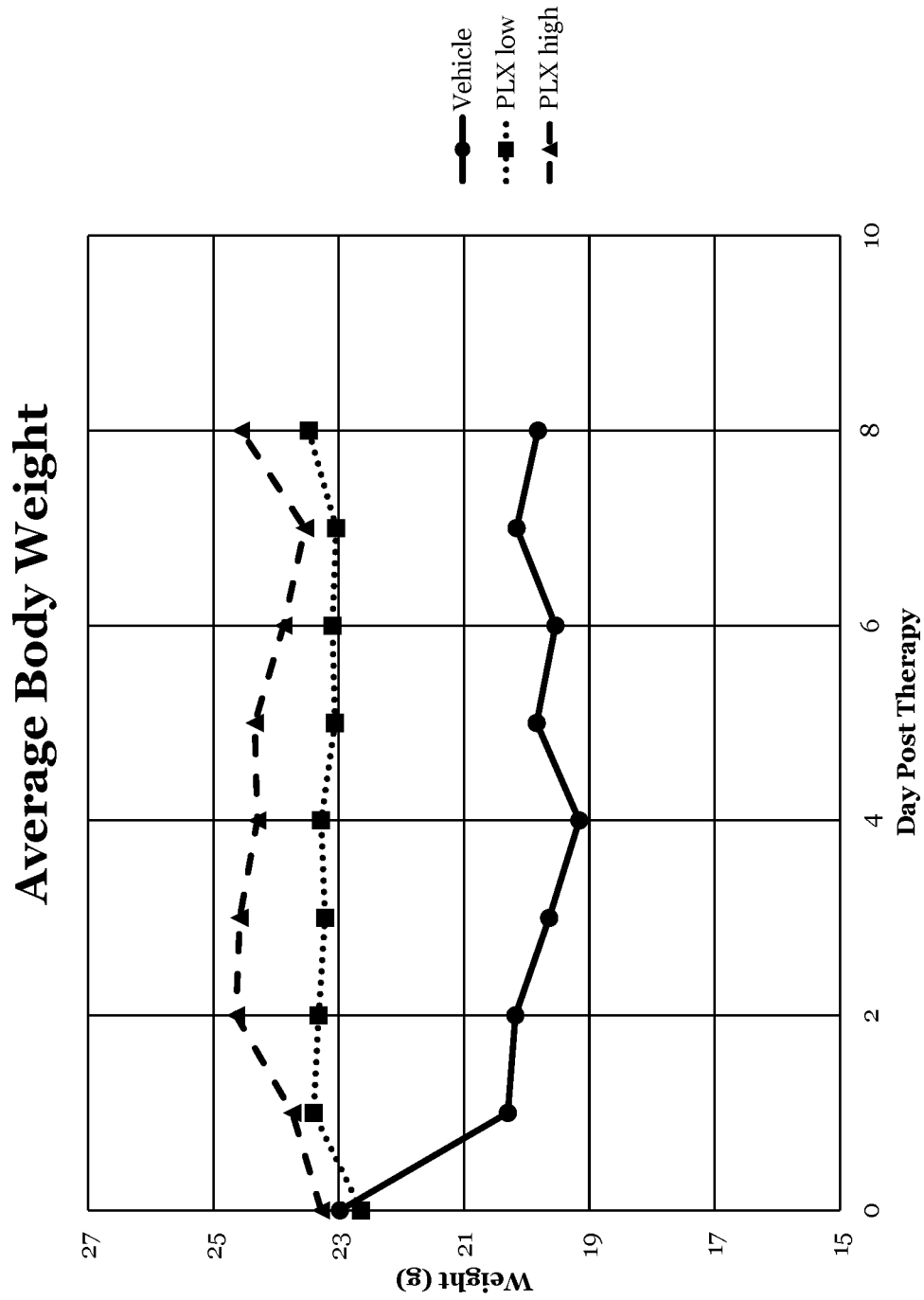
FIG. 10 shows body weight measured in STZ-induced diabetic mice treated with the insulin lispro-releasing hydrogel microsphere conjugate of Example 17. Mice were treated with streptozotocin to induce diabetes, then injected s.c. with a suspension of the conjugate comprising either 1.2 μmol/kg (low dose, squares) or 4.8 μmol/kg (high dose, triangles) of insulin lispro on days 0 and 7. Vehicle control (circles) consisted of non-peptide bearing microspheres. Both low and high doses of the conjugate maintained animal body weight, while the vehicle control lost 17% over 6 days.

These exenatide-releasing hydrogel microspheres have the general formula shown in FIG. 7, wherein $P^1$ and $P^2$ are each 4-armed poly(ethylene glycol)s, Z* is triazole, C* is carboxamide, B* is triazole, and L-D is the residue of a linker-drug of formula (II).

Example 19

Preparation of Linker-Oligonucleotides

Conjugates of a phosphorothioate CpG oligonucleotide (SEQ ID NO: 6,

T*C*G*A*A*C*G*T*T*C*G*A*A*C*G*T*T*C*G*A*A*C*G*T*T*C*G*A*A*T)

TLR9 receptor agonist were prepared as follows.

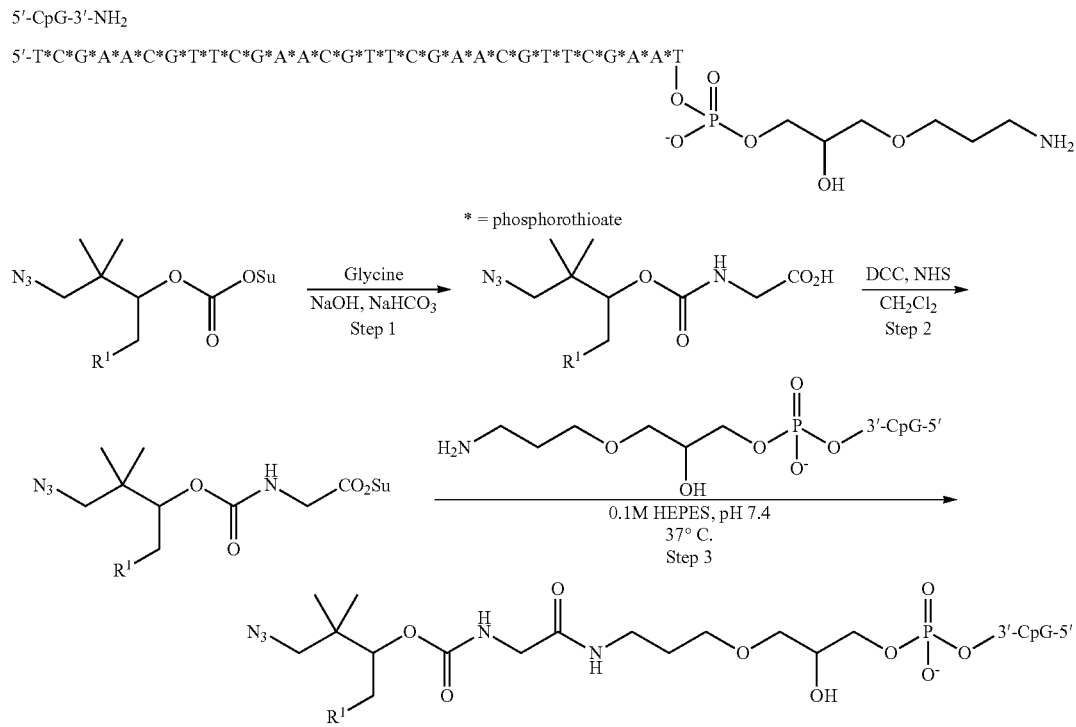

Step 1. N-[4-Azido-3,3-dimethyl-1-(4-chlorophenyl)sulfonyl-2-butyloxycarbonyl]-Gly-OH. A solution of glycine (18 mg, 0.24 mmol) in 0.56 mL of $H_2O$ was successively treated with 1 M aq NaOH (0.24 mL, 0.24 mmol), 1 M aq NaHCO$_3$ (0.20 mL, 0.20 mmol), and a solution of 4-azido-3,3-dimethyl-1-(4-chlorophenyl)sulfonyl-2-butyl succinimidyl carbonate (92 mg, 0.20 mmol, 0.1 M final concentration) in 1.0 mL of MeCN. After stirring for 45 min at ambient temperature, the reaction was judged to be complete by C18 HPLC (ELSD). The reaction was quenched with 5 mL of 1 M aq KHSO$_4$ then partitioned between 20 mL of 1:1 EtOAc:H$_2$O. The aqueous phase was extracted with 5 mL of EtOAc. The combined organic phase was washed with H$_2$O and brine (10 mL each) then dried over MgSO$_4$, filtered, and concentrated by rotary evaporation to provide the crude title compound (85 mg, 0.20 mmol, quantitative crude yield) as a cloudy film. C18 HPLC, purity was determined by ELSD: 98.6% (RV=9.42 mL). nLC-MS (m/z): calc for $^{35}$Cl, 417.1; obsd, 417.0 [M–H]$^-$; calc for $^{37}$Cl, 419.1; obsd, 419.1 [M–H]$^-$.

Step 2. N-[4-Azido-3,3-dimethyl-1-(4-chlorophenyl)sulfonyl-2-butyloxycarbonyl]-Gly-OSu. Dicyclohexylcarbodiimide (60% in xylenes, 2.6 M, 100 µL, 0.26 mmol) was added to a solution of N-[4-azido-3,3-dimethyl-1-(4-chlorophenyl)sulfonyl-2-butyloxycarbonyl]-Gly-OH (85 mg, 0.20 mmol, 0.1 M final concentration) and N-hydroxysuccinimide (30 mg, 0.26 mmol) in 1.9 mL of CH$_2$Cl$_2$. The reaction suspension was stirred at ambient temperature and monitored by C18 HPLC (ELSD). After 1 h, the reaction mixture was filtered through a cotton plug, and the filtrate was loaded onto a SiliaSep 4 g column. Product was eluted with a step-wise gradient of acetone in hexane (0%, 20%, 30%, 40%, 50%, 60%, 70%; 25 mL each). Clean product-containing fractions were combined and concentrated to provide the title compound (74 mg, 0.14 mmol, 70% yield) as a cloudy film. The product was then dissolved in 1.4 mL of MeCN and stored at −20° C. C18 HPLC, purity was determined by ELSD: 92.7% (RV=10.00 mL). Predominant impurity was hydrolysis product (7.3% @9.42 mL RV), possibly generated during HPLC chromatography.

Step 3. 3'-{N-[4-Azido-3,3-dimethyl-1-(4-chlorophenyl)sulfonyl-2-butyloxycarbonyl]-Gly-aminoalkyl}-CpG-5'. In a 15 mL Falcon tube, a 0.78 mM solution of CpG-3'-NH$_2$ (900 µL, 0.70 µmol, 0.5 mM final concentration) in 0.11 M HEPES pH 7.65 at 22° C. was diluted with 340 µL of 0.11 M HEPES (100 mM HEPES final, pH 7.4 at 37° C.). The solution was warmed in a 37° C. water bath for 30 min then treated with a 100 mM solution of N-[4-azido-3,3-dimethyl-1-(4-chlorophenyl)sulfonyl-2-butyloxycarbonyl]-Gly-OSu (140 µL, 14 mol, 10 mM final concentration) in DMF. The reaction was kept at 37° C. and periodically monitored by C18 HPLC. The starting material was converted to a single product peak in ~90% within 30 min. The reaction was diluted to 10 mL with Milli-Q water, and 2.5 mL of the solution was loaded onto each of four NAP-25 columns. The oligonucleotide was eluted from each column with 3.5 mL of Milli-Q water, per the manufacturer's protocol, and the eluates were combined to provide a 45 µM solution of total oligonucleotide (14.0 mL, 0.63 µmol total oligo; 91% linker-oligo by C18 HPLC) as judged by A260$_{H2O}$ [conc=0.65/(290300)*100/5]. The oligo solution was then concentrated to 1.4 mL using two Amicon Ultra-4, 10 kDa spin filters to provide a solution containing 0.44 mM total oligonucleotide (1.4 mL, 0.62 µmol total oligo) as judged by A260$_{H2O}$ [conc=0.64/(290300)*1000/5]. C$_{18}$ HPLC purity was determined at 260 nm: 90.9% (RV=5.98 mL). M$_a$, 10284 (calc); obsd, 10282 Da (ESI).

The corresponding linker-oligonucleotides wherein R$^1$=methylsulfonyl and R$^1$=phenylsulfonyl was prepared similarly.

Example 20

Preparation of Conjugated Linker-Oligonucleotides

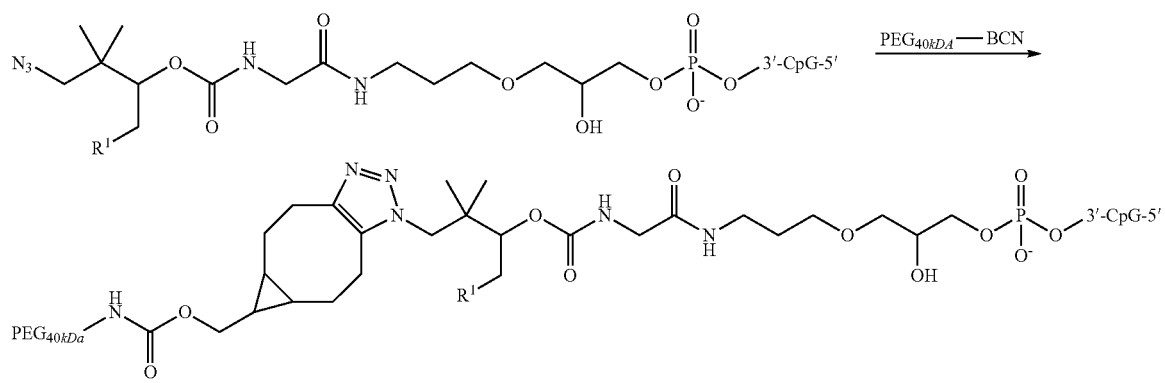

3'-[4-Branched-PEG$_{40kDa}$-BCN/N$_3$-(GDM 4-ClPhSO$_2$)-Gly-aminoalkyl]-CpG-5', 134BH32. In a 1.5 mL screw-cap Eppendorf tube, a solution of 3'-{N-[4-azido-3,3-dimethyl-1-(4-chlorophenyl)-sulfonyl-2-butyloxycarbonyl]-Gly-aminoalkyl}-CpG-5' (0.44 mM total oligo, 1.00 mL, 0.44 µmol total oligo) was diluted with 121 µL of 0.3 M MES buffer pH 6.0 (30 mM final buffer concentration). Next a 5 mM solution of 4-branched-PEG$_{40kDa}$-BCN (88 µL, 0.44 mol, 0.36 mM final concentration) in MeCN was added. The reaction was kept at ambient temperature and monitored by C18 HPLC. The starting material was converted to a single slower-eluting product peak. After 18 h, the reaction mixture contained ~60% product. The reaction tube was placed in a 32° C. heating block and agitated for 24 h, after which time the reaction mixture contained ~67% product. The mixture was loaded onto a Phenomenex Jupiter C18 prep column (150×21.2 mm), and product was eluted with 20%-95% MeCN in 50 mM Et$_3$N·HOAc, pH 7.0 over 20 min (8 mL/min). Clean, product-containing fractions were combined, and MeCN was removed by rotary evaporation to provide an aqueous solution containing 14 µM total oligo (15 mL, 0.21 µmol) as judged by A260$_{H2O}$ [conc=0.80/290300)/0.2 cm path]. The aqueous solution was further concentrated using two Amicon Ultra-15, 10 kDa spin filters to provide a solution containing 0.18 mM total oligonucleotide (1.4 mL, 0.25 mol, 71% yield) as judged by A260$_{H2O}$

[conc=0.26/(290300)*1000/5]. $C_{18}$ HPLC purity was determined at 260 nm: 97.2% (RV=8.26 mL).

Example 21

Kinetics of Oligonucleotide Release from Conjugates

In duplicate septum-capped 1.5 mL glass HPLC vials, 800 µL of 125 mM borate buffer (pH 9.0 @37° C.), and 182 µL of $H_2O$ were warmed in a 37° C. autosampler for ≥30 min. An aqueous solution of the conjugate of Example 19 wherein $R^1$=(4-chlorophenyl)sulfonyl (110 M total oligo, 18 µL, 2 µM total oligo final concentration) was added to each, and the cleavage reactions were periodically monitored by C18 HPLC. Product formation, CpG-3'-$NH_2$ HPLC peak area (260 nm) as a fraction of total 260 nm area, was plotted against time, giving an average $t_{1/2}$=1.2 h, which extrapolates to 48 h at pH 7.4.

All references disclosed herein are incorporated by reference in their entireties.

---

What is claimed is:

1. A linker of formula (I), $$Z-(CH_2)_n-\underset{\underset{R^4}{|}}{\overset{\overset{R^4}{|}}{C}}-\underset{\underset{H}{|}}{\overset{\overset{HC-R^2}{|}}{C}}-O-\overset{O}{\underset{}{\overset{\|}{C}}}-X, \quad (I)$$

wherein:
n is an integer from 0 to 6;
R$^1$ is —CN or —SO$_2$R$^3$, wherein R$^3$ is optionally substituted alkyl, optionally substituted aryl, or —N(R$^8$)$_2$, wherein each R$^8$ is independently optionally substituted alkyl, or both R$^8$ groups are taken together with the nitrogen to which they are attached to form an optionally substituted heterocyclic ring;
R$^2$ is H;
each R$^4$ is independently C$_1$-C$_3$ alkyl or the two R$^4$ are taken together with the carbon atom to which they attach to form a 3-6 member ring;
X is halogen, N-succinimidyloxy, nitrophenoxy, pentahalophenoxy, imidazolyl, triazolyl, tetrazolyl, or N(R$^6$)CH$_2$Cl, wherein R$^6$ is optionally substituted C$_1$-C$_6$ alkyl, optionally substituted aryl, or optionally substituted heteroaryl; and
Z is N$_3$, —NHC(O)C(OEt)$_2$CH$_3$, NH-pyruvoyl, maleimidyl, 1,2,4,6-tetrazinyl, trans-cyclooctenyl, bicyclononynyl, or cyclooctynyl.

2. The linker of claim 1, wherein Z is N$_3$, maleimidyl, 1,2,4,6-tetrazinyl, trans-cyclooctenyl, bicyclononynyl, or cyclooctynyl.

3. The linker of claim 1, wherein each R$^4$ is independently C$_1$-C$_3$ alkyl.

4. The linker of claim 1, where both R$^4$ are methyl.

5. The linker of claim 1, wherein R$^1$ is —CN.

6. The linker of claim 1, wherein and R$^1$ is SO$_2$R$^3$.

7. The linker of claim 6, where R$^3$ is methyl, isopropyl, phenyl, p-chlorophenyl, p-tolyl, dimethylamino, ethylmethylamino, 4-methylpiperidinyl, 4-morpholino, or bis(2-methoxyethyl)amino.

8. The linker of claim 1, wherein n is 1.

9. The linker of claim 1, wherein Z is N3.

10. The linker of claim 1, wherein Z is —NHC(O)C(OEt)$_2$CH$_3$.

11. The linker of claim 1, wherein Z is NH-pyruvoyl.

* * * * *